US011793783B2

(12) United States Patent
Ray, II

(10) Patent No.: US 11,793,783 B2
(45) Date of Patent: *Oct. 24, 2023

(54) COMPOSITIONS AND METHODS FOR TREATING AN INFECTION

(71) Applicant: CMPD Licensing, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/938,228

(22) Filed: Jul. 24, 2020

(65) Prior Publication Data

US 2020/0397742 A1 Dec. 24, 2020

Related U.S. Application Data

(63) Continuation-in-part of application No. 16/702,085, filed on Dec. 3, 2019, now Pat. No. 11,173,163, which is a continuation-in-part of application No. 16/270,335, filed on Feb. 7, 2019, which is a continuation-in-part of application No. 15/976,579, filed on May 10, 2018, now Pat. No. 11,278,590, and a continuation-in-part of application No. 15/881,009, filed on Jan. 26, 2018, now Pat. No. 10,898,491, and a continuation-in-part of application No. 15/668,184, filed on Aug. 3, 2017, and a continuation-in-part of application No. 15/625,989, filed on Jun. 16, 2017, now abandoned, and a continuation-in-part of application No. 15/597,936, filed on May 17, 2017, now Pat. No. 10,105,342, and a continuation-in-part of application No. 15/440,800, filed on Feb. 23, 2017, now abandoned, and a continuation-in-part of application No. 15/440,800, filed on Feb. 23, 2017, now abandoned, and a continuation-in-part of application No. 14/990,168, filed on Jan. 7, 2016, now Pat. No. 10,898,455, and a continuation-in-part of application No. 14/975,172, filed on Dec. 18, 2015, now Pat. No. 9,707,229, and a continuation-in-part of application No. 14/975,172, filed on Dec. 18, 2015, now Pat. No. 9,707,229, and a continuation-in-part of application No. 14/819,342, filed on Aug. 5, 2015, now Pat. No. 10,973,804.

(60) Provisional application No. 62/370,571, filed on Aug. 3, 2016, provisional application No. 62/298,994, filed on Feb. 23, 2016, provisional application No. 62/298,991, filed on Feb. 23, 2016.

(51) Int. Cl.
| | |
|---|---|
| *A61K 31/351* | (2006.01) |
| *A61K 31/506* | (2006.01) |
| *A61K 9/00* | (2006.01) |
| *A61K 9/06* | (2006.01) |
| *A61P 31/10* | (2006.01) |
| *A61K 31/7036* | (2006.01) |
| *A61K 31/65* | (2006.01) |
| *A61P 31/04* | (2006.01) |

(52) U.S. Cl.
CPC ............ *A61K 31/351* (2013.01); *A61K 9/006* (2013.01); *A61K 9/0014* (2013.01); *A61K 9/0031* (2013.01); *A61K 9/0034* (2013.01); *A61K 9/0043* (2013.01); *A61K 9/0046* (2013.01); *A61K 9/06* (2013.01); *A61K 31/506* (2013.01); *A61K 31/65* (2013.01); *A61K 31/7036* (2013.01); *A61P 31/04* (2018.01); *A61P 31/10* (2018.01)

(58) Field of Classification Search
CPC .... A61K 31/351; A61K 9/006; A61K 9/0043; A61K 9/0046; A61K 9/0031; A61K 9/0014
See application file for complete search history.

(56) References Cited

U.S. PATENT DOCUMENTS

| | | |
|---|---|---|
| 2,989,965 A | 6/1961 | Rod |
| 4,003,884 A | 1/1977 | Konig |
| 4,296,104 A | 10/1981 | Herschler |
| 4,382,886 A | 5/1983 | Sosnowski |
| 4,454,140 A | 6/1984 | Goldberg |
| 4,711,906 A | 2/1987 | von Stetten |
| 4,923,862 A | 5/1990 | Hirota |
| 5,324,746 A | 6/1994 | McKee |
| 5,536,743 A | 7/1996 | Borgman |
| 5,585,379 A | 12/1996 | Sintov |

(Continued)

FOREIGN PATENT DOCUMENTS

| | | |
|---|---|---|
| CN | 101347436 | 1/2009 |
| CN | 104922130 | 9/2015 |

(Continued)

OTHER PUBLICATIONS

Kumar et al. (Antifungal Agents: New approach for Novel Delivery Systems, J. Pharmaceutical Sciences and Research, 2014, vol. 6, Issue 5, pp. 229-235), (Year: 2014).*

(Continued)

*Primary Examiner* — Shengjun Wang
(74) *Attorney, Agent, or Firm* — AKERMAN LLP

(57) ABSTRACT

The present application relates to compounded compositions, methods of making compounded compositions, and methods of using compounded compositions. For example, disclosed herein are compounded compositions and methods of making compounded compositions comprising one or more antimicrobial agents such as mupirocin.

28 Claims, No Drawings

(56) References Cited

U.S. PATENT DOCUMENTS

| | | |
|---|---|---|
| 5,635,540 A | 6/1997 | Edlich |
| 5,710,280 A | 1/1998 | Shih |
| 5,776,926 A | 7/1998 | Bolz |
| 5,813,416 A | 9/1998 | Rudolph |
| 5,849,334 A | 12/1998 | Rivlin |
| 6,056,955 A | 5/2000 | Fischetti |
| 6,156,792 A | 12/2000 | Hatton |
| 6,159,955 A | 12/2000 | Asculai |
| 6,197,830 B1 | 3/2001 | Frome |
| 6,340,698 B1 | 1/2002 | Sherman |
| 6,365,635 B1 | 4/2002 | Nomura |
| 6,598,603 B1 | 7/2003 | Andersson |
| 6,656,928 B1 | 12/2003 | McCadden |
| 6,765,001 B2 | 7/2004 | Gans |
| 6,796,975 B2 | 9/2004 | Sims |
| 7,074,392 B1 | 7/2006 | Friedman |
| 7,220,431 B2 | 5/2007 | Sawchuk |
| 7,517,852 B2 | 4/2009 | Walsh |
| 7,803,357 B2 | 9/2010 | Cappello |
| 7,871,598 B1 | 1/2011 | Dellamary |
| 8,327,610 B1 | 12/2012 | Ray, II |
| 8,464,498 B1 | 6/2013 | Ray, II |
| 8,663,663 B1 | 3/2014 | Ray, II |
| 8,895,036 B1 | 11/2014 | Ray, II |
| 9,078,853 B2 * | 7/2015 | Ray, II ............... A61K 9/0046 |
| 9,155,915 B2 | 10/2015 | Kunin |
| 9,186,319 B2 | 11/2015 | Ray, II |
| 9,271,989 B2 | 3/2016 | Ray, II |
| 9,370,500 B2 | 6/2016 | Campbell |
| 9,468,599 B2 | 10/2016 | Ray, II |
| 9,468,601 B2 | 10/2016 | Ray, II |
| 9,592,241 B2 | 3/2017 | Ray, II |
| 9,707,229 B2 * | 7/2017 | Ray, II ................. A61K 47/26 |
| 9,717,748 B2 * | 8/2017 | Ray, II ............. A61K 31/7048 |
| 9,724,294 B2 | 8/2017 | Ray, II |
| 9,724,315 B2 | 8/2017 | Ray, II |
| 9,925,141 B2 | 3/2018 | Ray, II |
| 9,962,391 B2 | 5/2018 | Ray, II |
| 9,999,604 B2 | 6/2018 | Ray, II |
| 10,064,949 B2 | 9/2018 | Ray, II |
| 10,105,342 B2 * | 10/2018 | Ray, II ............... A61K 31/506 |
| 10,105,381 B2 * | 10/2018 | Ray, II ............... A61K 45/06 |
| 10,231,924 B2 | 3/2019 | Ray, II |
| 10,434,115 B2 * | 10/2019 | Ray, II ............... A61K 31/351 |
| 10,525,025 B2 | 1/2020 | Ray, II |
| 10,610,503 B2 | 4/2020 | Ray, II |
| 10,617,703 B2 | 4/2020 | Ray, II |
| 10,660,962 B2 | 5/2020 | Ray, II |
| 10,792,296 B2 | 10/2020 | Ray, II |
| 10,813,897 B2 | 10/2020 | Ray, II |
| 10,813,908 B2 * | 10/2020 | Ray, II ................... A61K 9/08 |
| 10,898,455 B2 | 1/2021 | Ray, II |
| 10,898,491 B2 | 1/2021 | Ray, II |
| 10,966,946 B2 | 4/2021 | Ray, II |
| 10,973,804 B2 | 4/2021 | Ray, II |
| 11,173,163 B2 | 11/2021 | Ray, II |
| 11,207,336 B2 | 12/2021 | Ray, II |
| 11,213,500 B2 | 1/2022 | Ray, II |
| 11,213,501 B2 | 1/2022 | Ray, II |
| 11,278,508 B2 | 3/2022 | Ray, II |
| 11,278,590 B2 | 3/2022 | Ray, II |
| 11,311,564 B2 | 4/2022 | Ray, II |
| 11,324,694 B1 | 5/2022 | Ray, II |
| 11,446,236 B2 | 9/2022 | Ray, II |
| 2001/0046526 A1 | 11/2001 | Greenfelder |
| 2002/0061281 A1 | 5/2002 | Osbakken |
| 2003/0091519 A1 | 5/2003 | Zatz |
| 2003/0143162 A1 | 7/2003 | Speirs et al. |
| 2003/0148949 A1 | 8/2003 | Podolsky |
| 2003/0226201 A1 | 12/2003 | Leung |
| 2003/0235541 A1 | 12/2003 | Maibach |
| 2004/0009126 A1 | 1/2004 | Pilkiewicz |
| 2004/0033963 A1 | 2/2004 | Yu |
| 2004/0087630 A1 | 5/2004 | Allison |
| 2004/0151765 A1 | 8/2004 | Ritchie |
| 2004/0191329 A1 | 9/2004 | Burrell |
| 2005/0043251 A1 | 2/2005 | Lane |
| 2005/0137164 A1 | 6/2005 | Arkin |
| 2005/0255048 A1 | 11/2005 | Hirsh |
| 2006/0246098 A1 | 11/2006 | Rao |
| 2006/0272089 A1 | 12/2006 | Berger |
| 2007/0161543 A1 | 7/2007 | Yu |
| 2007/0212340 A1 | 9/2007 | Fischetti |
| 2007/0293460 A1 | 12/2007 | Ray, II |
| 2008/0045564 A1 | 2/2008 | Roberts |
| 2008/0181962 A1 | 7/2008 | Brzeczko |
| 2008/0274165 A1 | 11/2008 | Van Dyke |
| 2008/0299060 A1 | 12/2008 | Bruno |
| 2009/0016990 A1 | 1/2009 | Alberte |
| 2009/0048347 A1 | 2/2009 | Cohen |
| 2009/0105668 A1 | 4/2009 | Monroe |
| 2009/0123537 A1 | 5/2009 | Debrouse |
| 2009/0298803 A1 | 12/2009 | Sen |
| 2009/0312724 A1 | 12/2009 | Pipkin et al. |
| 2010/0036000 A1 | 2/2010 | Lichter |
| 2010/0081669 A1 | 4/2010 | Yang |
| 2010/0111879 A1 | 5/2010 | Tamarkin |
| 2010/0152147 A1 | 6/2010 | Fuge et al. |
| 2010/0168233 A1 | 7/2010 | Jayes |
| 2010/0183519 A1 | 7/2010 | Katz |
| 2010/0215591 A1 | 8/2010 | Stone |
| 2010/0226948 A1 | 9/2010 | Jitpraphai |
| 2011/0052704 A1 | 3/2011 | Nazzal |
| 2011/0081384 A1 * | 4/2011 | Archambeau ........... A61L 15/44 977/915 |
| 2011/0105448 A1 | 5/2011 | Dhuppad |
| 2011/0105996 A1 | 5/2011 | Mustoe |
| 2011/0150992 A1 | 6/2011 | Arnold |
| 2011/0229536 A1 | 9/2011 | Kvitnitsky |
| 2011/0245786 A1 | 10/2011 | Hulse |
| 2011/0294763 A1 | 12/2011 | Dordunoo |
| 2012/0076734 A1 | 3/2012 | Olson |
| 2012/0149748 A1 | 6/2012 | Shanler |
| 2012/0157536 A1 | 6/2012 | Shah |
| 2012/0328671 A1 | 12/2012 | O'Neil et al. |
| 2013/0072563 A1 | 3/2013 | Ho |
| 2013/0085171 A1 | 4/2013 | Ray, II |
| 2013/0152505 A1 | 6/2013 | Ray, II |
| 2013/0165420 A1 | 6/2013 | Ray, II |
| 2013/0165429 A1 | 6/2013 | Ray, II |
| 2013/0165430 A1 | 6/2013 | Ray, II |
| 2013/0178801 A1 | 7/2013 | Branch |
| 2013/0184233 A1 | 7/2013 | Carter |
| 2013/0224151 A1 | 8/2013 | Pearson |
| 2014/0031314 A1 | 1/2014 | Morganti |
| 2014/0256826 A1 | 9/2014 | Lemire |
| 2014/0288621 A1 | 9/2014 | Efremkin |
| 2014/0348780 A1 | 11/2014 | Glasnapp |
| 2014/0371134 A1 | 12/2014 | Ray, II |
| 2014/0377357 A1 | 12/2014 | Banov |
| 2015/0025443 A1 | 1/2015 | Ray, II |
| 2015/0148305 A1 | 5/2015 | Ray, II |
| 2015/0182538 A1 | 7/2015 | Ray, II |
| 2015/0313836 A1 | 11/2015 | Ray, II |
| 2015/0320816 A1 | 11/2015 | Patel |
| 2015/0359740 A1 | 12/2015 | Ray, II |
| 2015/0359767 A1 | 12/2015 | Ray, II |
| 2015/0359768 A1 | 12/2015 | Ray, II |
| 2016/0022653 A1 | 1/2016 | Dooley |
| 2016/0128959 A1 | 5/2016 | Ray, II |
| 2016/0166505 A1 | 6/2016 | Ray, II |
| 2016/0220593 A1 | 8/2016 | Anastassov |
| 2016/0279057 A1 | 9/2016 | Ray, II |
| 2017/0027865 A1 | 2/2017 | Ray, II |
| 2017/0035736 A1 | 2/2017 | Ray, II |
| 2017/0096418 A1 | 4/2017 | Patron |
| 2017/0136028 A1 | 5/2017 | Ray, II |
| 2017/0173002 A1 | 6/2017 | Ray, II |
| 2017/0173003 A1 | 6/2017 | Ray, II |
| 2017/0173062 A1 | 6/2017 | Ray, II |
| 2017/0173063 A1 | 6/2017 | Ray, II |
| 2017/0182167 A1 | 6/2017 | Ray, II |
| 2017/0196823 A1 | 7/2017 | Ray, III |
| 2017/0239277 A1 | 8/2017 | Ray, II |

(56) References Cited

U.S. PATENT DOCUMENTS

| | | |
|---|---|---|
| 2017/0246140 A1 | 8/2017 | Ray, II |
| 2017/0273897 A1 | 9/2017 | Ray, II |
| 2017/0273898 A1 | 9/2017 | Ray, II |
| 2017/0312276 A1 | 11/2017 | Ray, II |
| 2017/0326167 A1 | 11/2017 | Ray, II |
| 2017/0333464 A1 | 11/2017 | Ray, II |
| 2017/0333466 A1 | 11/2017 | Ray, II |
| 2017/0333467 A1 | 11/2017 | Ray, II |
| 2018/0036227 A1 | 2/2018 | Ray, II |
| 2018/0078492 A1 | 3/2018 | Ray, II |
| 2018/0133178 A1 | 5/2018 | Ray, II |
| 2018/0147211 A1 | 5/2018 | Ray, II |
| 2018/0147212 A1 | 5/2018 | Ray, II |
| 2018/0250248 A1 | 9/2018 | Ray, II |
| 2018/0256675 A1 | 9/2018 | Ray, II |
| 2018/0296515 A1 | 10/2018 | Ray, II |
| 2018/0360740 A1 | 12/2018 | Ray, II |
| 2019/0054061 A1 | 2/2019 | Ray, II |
| 2019/0054107 A1 | 2/2019 | Ray, II |
| 2019/0060464 A1 | 2/2019 | Ray, II |
| 2019/0105269 A1 | 4/2019 | Ray, II |
| 2019/0167527 A1 | 6/2019 | Ray, II |
| 2019/0175636 A1 | 6/2019 | Ray, II |
| 2019/0209461 A1 | 7/2019 | Ray, II |
| 2019/0231723 A1 | 8/2019 | Ray, II |
| 2019/0247300 A1 | 8/2019 | Ray, II |
| 2019/0255086 A1 | 8/2019 | Ray, II |
| 2020/0030354 A1 | 1/2020 | Ray, II |
| 2020/0101011 A1 | 4/2020 | Ray, II |
| 2020/0101082 A1 | 4/2020 | Ray, II |
| 2020/0113899 A1 | 4/2020 | Chase |
| 2020/0121696 A1 | 4/2020 | Ray, II |
| 2020/0121795 A1 | 4/2020 | Ray, II |
| 2020/0138757 A1 | 5/2020 | Ray, II |
| 2020/0179409 A1 | 6/2020 | Ray, II |
| 2020/0237795 A1 | 7/2020 | Ray, II |
| 2020/0261387 A1 | 8/2020 | Ray, II |
| 2020/0323808 A1 | 10/2020 | Ray, II |
| 2020/0352953 A1 | 11/2020 | Ray, II |
| 2020/0375849 A1 | 12/2020 | Ray, II |
| 2020/0397742 A1 | 12/2020 | Ray, II |
| 2021/0023114 A1 | 1/2021 | Ray, II |
| 2021/0038548 A1 | 2/2021 | Ray, II |
| 2021/0106553 A1 | 4/2021 | Ray, II |
| 2021/0205215 A1 | 7/2021 | Ray, II |
| 2021/0220307 A1 | 7/2021 | Ray, II |
| 2021/0386748 A1 | 12/2021 | Ray, II |
| 2022/0047590 A1 | 2/2022 | Ray, II |
| 2022/0047627 A1 | 2/2022 | Ray, II |
| 2022/0072007 A1 | 3/2022 | Ray, II |
| 2022/0110859 A1 | 4/2022 | Ray, II |
| 2022/0117923 A1 | 4/2022 | Ray, II |
| 2022/0117988 A1 | 4/2022 | Ray, II |
| 2022/0211801 A1 | 7/2022 | Ray, II |
| 2022/0249485 A1 | 8/2022 | Ray, II |
| 2022/0265694 A1 | 8/2022 | Ray, II |
| 2022/0304894 A1 | 9/2022 | Ray, II |

FOREIGN PATENT DOCUMENTS

| | | | | |
|---|---|---|---|---|
| CN | 105012960 | 11/2015 | | |
| EP | 1174133 | 1/2002 | | |
| EP | 1174133 A1 * | 1/2002 | ........... | A61K 31/351 |
| EP | 1762226 | 3/2007 | | |
| ES | 2245611 | 3/2007 | | |
| IN | 2014MU3504 | 5/2016 | | |
| JP | H-0774144 | 8/1995 | | |
| RU | 2317810 | 2/2008 | | |
| WO | 2004037197 | 5/2004 | | |
| WO | 2006060027 | 6/2006 | | |
| WO | 2007098868 | 9/2007 | | |
| WO | 2013063354 | 5/2013 | | |
| WO | 2014026707 | 2/2014 | | |
| WO | 2014167554 | 10/2014 | | |
| WO | 201405159 | 12/2014 | | |

OTHER PUBLICATIONS

Howes ("Topical use of Streptomycin in Wounds," The American Journal of Medicine, 1947, vol. 2, Issue 5, pp. 449-456) (Year: 1947).*

Farstvedt et al. ("Update on topical wound Medications," Clinical Techniques in Equine Practice, 2014, vol. 3, pp. 164-172) (Year: 2014).*

Drug Bank online "Streptomycin" https://go.drugbank.com/drugs/DB01082 (Year: 2022).*

Drug Bank online, "Voriconazole" https://go.drugbank.com/drugs/DB00582 (Year: 2022).*

Bank online, Doxycycline https://go.drugbank.com/drugs/DB00254 (Year: 2022).*

Drug Bank online, Ketoconazole https://go.drugbank.com/drugs/DB01026. (Year: 2022).*

PCCA Loxaseerse Studies (2013 and 2014, pp. 1-12).

PCCA publication No. 30-4701 (2013), pp. 1-2.

PCCA, PCCA LoxaSpere, Oct. 2013.

Freels, How to Make an Antifungal Foot Soak for Treatment of Foot Fungus, Lexington Podiatry (2011), 1-2.

PCCA, New, Exclusive PCCA Base, XyliFosTM: Boost the LoxaSperse. Power in Nasal Nebulization and Decrease your Cost, http://www.pccarx.com/what-is-com pounding/com pourriding. Articles/item/273-new-exclusi ve-pcca Base-xyl ifos, Au.. 2015, pp. 1-2.

PCCA Science, the Antimicrobial Activity of Itraconazole and LoxaSperse Tm Against Biofilms of C. albicans, 2013, www.pccarx.com, pp. 1-2.

LoxaSperse (Characterization of the Physical and Microbiological Properties of LoxaSperse, Pcca Science, Aug. 2014).

May et al., Management of allergic rhinitis: a review for the community pharmacist. Clinical Therapeutics, vol. 39(12), p. 2410-2419, (Year: 2017).

MedlinePlus Drug Information, Methylprednisolone, last revised Sep. 15, 2017.

Yuzkat et al., Effects of theophylline with methylprednisolone combination therapy on biomechanics and histopathology in diaphragm muscles of rats. Inflammation, vol. 39(5), pp. 1635-1641, (Year: 2016).

Colak et al., Sugammadex-Induced Hypersensitivity Reaction in a Pediatric Patient. Turk J. Anaesthesiol. Reanim, vol. 46, pp. 66-68, Feb. (Year: 2018).

Prescribing Information for Levofloxacin Oral Solution 25 mg/mL, Hi-Tech Pharmaceutical Col, Inc. (Rev. 286: Aug. 4, 2012). (Year: 2012).

Kumar et al., Topical anesthesia, 2015, J Anesthesiol Clin Pharmacol, 31(4),.

Kumar et al., Clonidine for management of chronic pain: A brief review of The current evidences, 2014, Saudi J Anesth., 8(1), pp. 92-96 (Year: 2014).

Tandel, A. et al., Transungual Permeation of the Voriconazole Nail Lacquer. Against Trichophyton Rubrum, 2012, Journal of Drug Delivery & Therapeutics, vol. 2, Issue 1, pp. 25-33. (Year: 2012).

Rocephin (ceftriaxone injection)Product Sheet, Galaxy Container, 2004, Roche Pharmaceuticals, 2 pages. (Year: 2004).

Bae et al., Green Nail Syndrome Treated with the Applicationn of Tobramycin Eye Drop, 2014, Ann Dermatology, vol. 26, No. 4, pp. 514-516. (Year: 2014).

Angamuthu et al., Controlled-release injectable containing Terbinafine/PLGA microspheres for Onychomycosis Treatment, 2014, Journal of Pharmaceutical Sciences, vol. 103, pp. 1178-1183. (Year: 2014).

Mutizwa et al., Treatment of facial angiofibromas with topical application of oral rapamycin solution (1 mg mL)1) in two patients with tuberous sclerosis, British Association of Dermatologists 2011 165, DOI: 10.1111/j.13652133.2011.10476.x (Year: 2011).

Streptomycin packaging page retrieved from the web Aug. 25, 2020 (Year: 2020).

Urea Cream. Formulation Record. [online]. Pharmlabs UNC, 2003 [retrieved on Sep. 24, 2020]. Retrieved from the Internet: <URL: https://pharmnlabs.unc.edu/labs/fornnulation records/urea cream fornn.pdf>. (Year: 2003).

(56) References Cited

OTHER PUBLICATIONS

Urea Powder, Technical Grade. [online]. Rose Mill Chemicals and Lubricants, 2009, [retrieved on Sep. 24, 2020]. Retrieved from the Internet: <URL:https://rosennill.conn/wp-content/uploads/2018/02/ureapowder.pdf>. (Year: 2009).

Jacoby, R.H., a New Urea/Hydrocortisone Powder-Cream Compared with other Topical Corticosteroid Preparations: a Six-Center Study, 1974, Current Medical Research and Opinion, vol. 2, No. 8, pp. 474-481. (Year: 1974).

Clobetasol Propionate Cream, USP 0.05% and Clobetasol Propionate Ointment, USP 0.05%. Information Sheet [online]. DailyMed.nlm.nih.gov, 2012, [retrieved on Mar. 11, 2020]. Retrieved from the Internet<URL:https://dailynned.nInn.nih.gov/dailynned/fda/fdaDrugXsl.cfnn?setid=b6575dd5Afa3-433b-860f-6d61cf8796a1> (Year: 2012).

Akorn Pharmaceuticals (EMLA cream product page) (Year: 2008).

Pain Management Compounding (Published online 2010) (Year: 2010).

Taro Pharmaceuticals USA, Inc. (Lidocaine Ointment, https://dailynned.nInn.nih.gov/dailynned/fda/fdaDrugXsl.cfnn?setid—ae758020A508-4a2e-8164-e6c324e826a3&type=display, obtained from the internet Jul. 13, 2018, last revised Apr. 2015) (Year: 2015).

LidoVir fact sheet (LidoVir Ointment Compunding Kit, 2012) (Year: 2012).

Zovirax® (Prescribing Information, https://www.accessdata.fda.gov/drugsatfdadocs/1abe1/2005/018828s030%2C 020089s019%2C019909s020Ibl.pdf, obtained from the internet Aug. 29, 20219, GlaxoSmithKline,Jun. 2005) (Year: 2005).

V Pavan-Langston (Ophthalmology, 2008, 115, S13-S20) (Year: 2008).

Sutherland et al. Antimicrobial Agents and Chemotherapy (1985), vol. 27, pp. 495-498.

Allen U.S. Pharm. (2011), vol. 36(6), pp. 44-45.

Lewandowski et al. Military Medicine (20130, vol. 178, pp. e503-e507.

Jaloob et al. "Effect of some antibiotics on aerobic pathogenic bacteria causing otitis and urinary tract infection in Al-Manathera city in Iraq: A comparative in vitro study," QMJ, 2012, vol. 8, No. 13, pp. 156-168. (Year: 2012).

Chiriac et al., Chloronychia: "Green nail syndrome caused by Pseudomonas aeruginosa in elderly persons," Clinical Interventions in Aging, Jan. 2015, vol. 10, pp. 265-267. (Year: 2015).

BeyondDisease.com, "Does Bleach Kill Toenail Fungus? How to Use it?," 5 pages, available at http://www.beyonddisease.com/bleach-for-nail-fungus (published on Jun. 30, 2015).

Lee Silsby, "Loxasperse TM Formulations," 3 pages, webpage capture of http://leesilsby.com/loxasperseformulations on Oct. 17, 2014.

Bhapkar et al. IOSR Journal of Pharmacy (2013), vol. 3, pp. 24-48.

Bactroban® Ointment (mupirocin ointment, 2%) Prescribing Information, GlaxoSmithKlinc, Revised May 2014 (17 pages).

Aticlate® (Doxycycline Hyclate Tablets), Final Labeling Text, Aqua Pharmaceuticals, Revised Jul. 2014 (18 pages).

Ketoconazole Human Prescription Drug Label; Physician's Desk Reference, Ver. 1—Published Feb. 2007 (5 pages).

Tobramycin Human Prescription Drug Label; Physician's Desk Reference, Ver. 1—Published May 2014 (9 pages).

Ciprofloxacin Human Prescription Drug Label; Physician's Desk Reference, Ver. 1—Published Feb. 2010 (19 pages)) (hereinafter Ciprofloxacin PDR).

Coly-Mycin M Parenteral (Colistimethate for Injection, USP), Oct. 2006, Monarch Pharmaceuticals, NDA 50-108/S-026, 7 pages. (Year: 2006).

Doncker, P., Management of fungal skin infections with 15 days itraconazole treatment: a worldwide review, 1990, Br. J. Clin Pract Suppl. vol. 71, Abstract, 1 page. (Year: 1990).

Voriconazole, Medication Fact Sheet, 2009, Pfizer Canada, Inc., 2 pages. (Year: 2009).

Khot et al (British Journal of Dermatology, 2015, 173, 288-314) (Year: 2015).

Haynes et al., Occurrence of Pharmaceutically Acceptable Anions and Cations in the Cambridge Structural Database. Journal of Pharmaceutical Sciences, 2005, 94, 2111-2120.

Krochmal, L., Topical corticosteroid compounds: Effects on physiochemical stability and skin penetration rate, Nov. 1989, Journal of the American Academy of Dermatology, vol. 21, No. 5, Part 1, pp. 979-984. (Year: 1989).

Kanai et al., "Efficacy of a Metered-dose 8% Lidocaine Pump Spray for Patients with Post-herpetic Neuralgia," Pain Med. 10(5), 902-09 (2009).

4% Xylocaine®-MPF (lidocaine HCI) Sterile Solution prescribing information, APP Pharmaceuticals, LLC (Feb. 2010).

Lidex Drug Information Sheet. Product Sheet [online], Rxlist, 2014 [retrieved on Dec. 9, 2018], Retrieved from the Internet<https://web.archive.org/web/20140708143835/https://www.rxlist.corn/lidex-drug.htrn>, pp. 1-3. (Year: 2014).

U.S. Pharmacist, Anosmia, US Pharm.vol. 36(1), 17-18 (Year: 2011).

Mott et al., Topical corticosteroid treatment of anosmia associated with nasal and sinus disease. Arch. Otolaryngol. Head Neck Surg., col. 123(4), Abstract (Year: 1997).

The Asthma Center, Smell loss promising New Treatment, Mar. 29, (Year: 2017).

Wang et al., Comparison of inhaled corticosteroid combined with theophylline and double-dose inhaled corticosteroid in moderate to severe asthma. Respirology, Mar. 31 (Year: 2005).

Cafasso, What is Anosmia? Updated Aug. 29 (Year: 2019).

TGM EDS, Rhinitis: diagnosis and treatment (http://www.tgmeds.org.uk/rhinitis-diagnosis-and-treatment. html) (Year: 2005).

Kook, Increased expression of bitter taste receptors in human allergic nasal mucosa and their contribution to the shrinkage of human nasal mucosa, Clinical & Experimental Allergy, 46, 584-601 (Year: 2016).

Munch, a Comparative Study of Dexchlorpheniramine Maleate Sustained Release Tablets and Budesonide Nasal Spray in Seasonal Allergic Rhinitis, Allery 1983, 38, 517-524 (Year: 1983).

El-Gendy, Development of Budesonide NanoCluster Dry Powder Aerosols: Formulation and Stability, Published online May 22, 2012 in Wiley Online Library (wileyonlinelibrary.com). DOI 10.1002 I jps.23176 (Year: 2012).

Akpabio, E.I., Formulation and Evaluation of Drug Delivery Systems for the Administration of Ciprofloxacin Hydrochloride to the Female Genital Tract, 2012, Department of Pharmaceutical Technology and Industrial Pharmacy, University of Nigeria Nsukka, 149 pages. (Year: 2012).

Ermis, S.S. et al., Effect of Topical Dexamethasone and Ciprofloxacin on Bacterial Flora of Healthy Conjunctiva, 2004, Eye, vol. 18, pp. 249-252. (Year: 2004).

Morpeth, J.F. et al, A comparison of cortisporin and ciprofloxacin otic drops as prophylaxis against post-tympanostomy otorrhea, 2001, International Journal of Pediatric Otorhinolaryngology, vol. 61, pp. 99-104. (Year: 2001).

Moen, M.D., Topical Diclofenac Solution, 2009, Drugs, vol. 69, Issue 18, pp. 2621-2632. (Year: 2009).

Pai, S., Effect of Calcium Hydroxide and Triple Antibiotic Paste as Intracanal Medicaments on the Incidence of Inter-Appointment flair up in Diabetic Patients: an in vivo study, 2014, J. Of Conserv. Dent., vol. 17, Issue 3, retrieved from <https://www.ncbi.nInn.nih.gov/pnnc/articles/PMC4056388/>, 10 pp.

Hydrochloroquine, 2013, Michigan Collaborative Standardization of Compounded Oral Liquids, Michigan Pharmacists Association, College of Pharmacy University of Michigan, p. 1. (Year: 2013).

Kowalski et al., "Topical levofloxacin 1.5% overcomes in vitro resistance in rabbit keratitis models," Acta Ophthalmol. Jun. 2010; 88 (4): e120-e1251; cited as pp. 1-14. (Year: 2010).

IQUIX® PDR, Vistakon Pharmaceuticals; 6 pages. (Revised Mar. 2010). (Year: 2010).

Fluocinolone Acetonide Topical Solution USP 0.01% Product Information Sheet. Product Sheet [online] NIH, 2007 [retrieved on 2020-06-19], Retrieved from the Internet:< https://dailyrned.nIrmnih.gov/dailyrned/fda/fdaDrugXsl.cfrOsetid=372a6a06-c9de-48d5Ad02-c4004038f85e&type=display>, 5 pages. (Year: 2007).

Balzarini et al. Lancet (2007), vol. 369, pp. 787-797.

(56) References Cited

OTHER PUBLICATIONS

Herold et al. (Toxicology and Applied Pharmacology (2008), vol. 65, pp. 329-335) (Year: 2008).
Tu et al., "Topical Linezolid 0.2% for the Treatment of Vancomycin-Resistant or Vancomycin-Intolerant Gram-Positive Bacterial Keratitis," American Journal of Ophthalmology, Jun. 2013; 55(6): pp. 1095-1098.e1. (Year: 2013).
Zyvox® PDR, Pharmacia and Upjohn Company; 35 pp. (Revised Feb. 2012). (Year: 2012).
Purvis, T., Simultaneous High Performance Liquid Chromatography Assay of Pentoxifylline, Mupirocin, Itraconazole, and Fluticasone Propionate in Humco Lavare Wound Base, 2015, Chromatography, 2, pp. 642-654.
Humco, https://www.humco.com/pharmaceuticals/lavare/, accessed Oct. 1, 2017.
Best Practice Journal, Cold season in primary care: Advice is the best medicine. vol. 52, pp. 26-33 (Year: 2013).
Yousefichaij an et al., The effect of zinc sulfate on duration of common cold symptoms in children. J. Biology and Today's World, vol. 6(10), pp. 186-190 (Year: 2017).
Litak, Jason, Should you put some zinc in that stuffy nose? Nutrition Noteworthy, vol. 7(1) (Year: 2005).
Fashner et al., Treatment of the common cold in children and adults. American Family Physician, vol. 86(2), pp. 153-159 (Year: 2012).
Thorsson, Systemic availability of budesonide after nasal administration of three different formulations: pressurized aerosol, aqueous pump spray, and powder, Ltd Br J Clin Pharmacol, 1999, 47, pp. 619-624. (Year: 1999).
MedInvent, "The NasoNeb Nasal Nebulizer", Nov. 15, 2013.

\* cited by examiner

COMPOSITIONS AND METHODS FOR TREATING AN INFECTION

CROSS-REFERENCE TO RELATED APPLICATIONS

This patent application is a continuation in-part application of co-pending U.S. patent application Ser. No. 16/702,085, filed Dec. 3, 2019, which is a continuation in-part of U.S. patent application Ser. No. 15/881,009, filed Jan. 26, 2018 and U.S. patent application Ser. No. 16/270,335, filed Feb. 7, 2019, each of which is hereby incorporated by reference in its entirety. U.S. patent application Ser. No. 15/881,009 is a continuation in-part of U.S. patent application Ser. No. 15/625,989, filed Jun. 16, 2017, which is a continuation-in-part of U.S. patent application Ser. No. 14/975,172 (now U.S. Pat. No. 9,707,229), filed Dec. 18, 2015, and U.S. patent application Ser. No. 15/440,800, filed Feb. 23, 2017. U.S. patent application Ser. No. 16/270,335 is a continuation-in-part of U.S. patent application Ser. No. 15/976,579, filed May 10, 2018, which is a continuation-in-part of U.S. patent application Ser. No. 14/990,168, filed Jan. 7, 2016, U.S. patent application Ser. No. 15/597,936, filed May 17, 2017, and U.S. patent application Ser. No. 15/668,184, filed Aug. 3, 2017. U.S. patent application Ser. No. 15/597,936 is a continuation-in-part application of U.S. patent application Ser. No. 15/440,800, filed Feb. 23, 2017, U.S. patent application Ser. No. 14/975,172, (now U.S. Pat. No. 9,707,229) filed Dec. 18, 2015, and U.S. patent application Ser. No. 14/819,342, filed Aug. 5, 2015. U.S. patent application Ser. No. 15/440,800 claims the benefit of U.S. Provisional Patent Application No. 62/298,991, filed Feb. 23, 2016, and U.S. Provisional Patent Application No. 62/289,994, filed Feb. 23, 2016. U.S. patent application Ser. No. 15/668,184 claims the benefit of U.S. Provisional Patent Application No. 62/370,571, filed on Aug. 3, 2016. Each of the provisional and nonprovisional patent applications listed above is hereby incorporated by reference in its entirety.

BACKGROUND

The body normally serves as host for a variety of bacteria and fungi. Most of the time, the balance between the body as host and the microorganisms is maintained. However, there are times when the physiological, biochemical, and/or environmental conditions permit the microorganisms to tip that balance, thereby causing an infection.

Despite advances in the understanding of the pathology of bacterial infections and fungal infections, there is still a need for compositions and methods that efficiently treat or prevent the progression and reoccurrence of bacterial infections and fungal infections that affect the skin, the respiratory system, or the feet.

SUMMARY

In one aspect, a method of treating one or both of a bacterial infection or fungal infection of a subject includes preparing a treatment solution comprising mupirocin, such as mupirocin 2% cream or ointment, at least one of an antifungal agent or an additional antibacterial agent, and an aqueous diluent, and topically administering the treatment solution to the subject. Topically administering the treatment solution may include contacting a surface of a tissue of the subject to be treated with the treatment solution.

In one embodiment, the tissue surface includes a nasal cavity of the subject, and the treatment solution is administered by contacting infected mucosal tissue of the nasal cavity via irrigation, spray, or nasal nebulization. In another embodiment, the tissue surface includes a vagina or anus of the subject, and the treatment solution is administered intravaginalally or rectally by contacting infected mucosal tissue of the vagina or anus with the treatment solution. In still another embodiment, the tissue surface includes a mouth of the subject, and the treatment solution is administered buccally by contacting infected mucosal tissue of the mouth with the treatment solution. In yet another embodiment, the tissue surface includes skin of the subject, and the treatment solution is sprayed onto the infected skin surface or the infected skin surface is irrigated with or submerged in the treatment solution. In another embodiment, the tissue surface includes an ear of the subject, and the treatment solution is administered intra-aurally.

In various embodiments, the at least one antifungal agent or additional antibacterial agent includes an antibacterial agent selected from doxycycline, bacitracin, colistimethate, piperacillin-tazobactam, polymyxin B, tobramycin, or streptomycin. In one example, the antibacterial agent includes one or more of bacitracin for injection, colistimethate sodium for injection, pentasodium colistin methanesulfonate for injection, piperacillin-tazobactam for injection, polymyxin B for injection, tobramycin sulfate for injection, or streptomycin sulfate for injection.

In one embodiment, the at least one antifungal agent or additional antibacterial agent includes an antifungal agent selected from voriconazole or amphotericin B. In one example, the antifungal agent includes one or more of voriconazole for injection or amphotericin B for injection.

In one embodiment, the at least one antifungal agent or additional antibacterial agent includes doxycycline, bacitracin, colistimethate, piperacillin-tazobactam, polymyxin B, voriconazole, streptomycin, tobramycin, or amphotericin B. In one example, the at least one antifungal agent or additional antibacterial agent includes bacitracin for injection, colistimethate sodium for injection, pentasodium colistin methanesulfonate for injection, piperacillin-tazobactam for injection, polymyxin B for injection, voriconazole for injection, streptomycin sulfate for injection, tobramycin sulfate for injection, or amphotericin B for injection.

In one embodiment, the at least one antifungal agent or additional antibacterial agent includes doxycycline, streptomycin, and ketoconazole. In one example, preparing the treatment solution includes adding the doxycycline, streptomycin, and ketoconazole to the aqueous diluent. The doxycycline, streptomycin, and ketoconazole may include crushed doxycycline hyclate tablet, crushed ketoconazole tablet, and streptomycin sulfate for injection.

In an embodiment, the at least one antifungal agent or additional antibacterial agent includes voriconazole and one of (i) streptomycin, (ii) streptomycin and doxycycline, or (iii) doxycycline and tobramycin. In one embodiment, the aqueous diluent includes sodium hypochlorite or Dakin's solution.

In various embodiments, preparing the treatment solution includes adding a compounded composition to the aqueous diluent, and the compounded composition includes mupirocin 2% cream or ointment and at least a portion of the at least one antifungal agent or additional antibacterial agent. In one example, the compounded composition includes a compounded cream or ointment including mupirocin 2% cream or ointment in an amount at least 60% w/w of the compounded cream or ointment and an antimicrobial for injection powder in an amount from about 1% to about 20% w/w of the compounded cream or ointment, wherein the antimicrobial for injection includes one or more of bacitracin for injection, colistimethate sodium for injection, pentasodium colistin methanesulfonate for injection, piperacillin-tazobactam for injection, polymyxin B for injection, streptomycin sulfate for injection, voriconazole for injection, tobramycin sulfate for injection, or amphotericin B for injection. In some examples, the antimicrobial for injection may include voriconazole for injection.

Preparing the treatment solution, for example, may include compounding the compounded cream or ointment comprising combining mupirocin 2% cream or ointment in an amount about 86% w/w of the compounded cream or ointment and voriconazole for injection in an amount about 0.8% w/w of the compounded cream or ointment. In a further example, the antimicrobial for injection further includes streptomycin sulfate for injection. Preparing the treatment solution may further include compounding the compounded cream or ointment comprising combining mupirocin 2% cream or ointment in an amount about 80% w/w of the compounded cream or ointment, voriconazole for injection in an amount about 0.8% w/w of the compounded cream or ointment, and streptomycin sulfate for injection in an amount about 5.528% w/w of the compounded cream or ointment. In one example, preparing the treatment solution further includes compounding the compounded cream or ointment comprising combining crushed doxycycline hyclate tablet powder.

In additional examples, preparing the treatment solution includes compounding a compounded cream or ointment comprising combining mupirocin 2% cream or ointment in an amount about 77.6% w/w of the compounded cream or ointment, voriconazole for injection in an amount about 0.8% w/w of the compounded cream or ointment, streptomycin sulfate for injection in an amount about 5.528% w/w of the compounded cream or ointment, and a sufficient amount of crushed doxycycline hyclate tablet powder to obtain about 1% w/w doxycycline in the compounded cream or ointment.

In one example, the antimicrobial for injection includes tobramycin for injection and the compounded cream or ointment further includes crushed doxycycline hyclate tablet powder. In a further example, preparing the treatment solution further includes compounding the compounded cream or ointment, including combining mupirocin 2% cream or ointment in an amount about 81.3% w/w of the compounded cream or ointment, voriconazole for injection in an amount about 0.8% w/w of the compounded cream or ointment, tobramycin sulfate for injection in an amount about 1.8% w/w of the compounded cream or ointment, and a sufficient amount of crushed doxycycline hyclate tablet powder to obtain about 1% w/w doxycycline in the compounded cream or ointment.

In another example, the antimicrobial for injection includes streptomycin sulfate for injection, and the compounded cream or ointment further includes crushed doxycycline hyclate tablet powder and crushed ketoconazole tablet powder. In a further example, preparing the treatment solution further includes compounding the compounded cream or ointment, including combining mupirocin 2% cream or ointment in an amount about 85.7% w/w of the compounded cream or ointment, streptomycin sulfate for injection in an amount about 5.528% w/w of the compounded cream or ointment, a sufficient amount of crushed doxycycline hyclate tablet powder to obtain about 2% w/w doxycycline in the compounded cream or ointment, and a sufficient amount of crushed ketoconazole tablet powder to obtain about 2.5% w/w ketoconazole in the compounded cream or ointment.

DETAILED DESCRIPTION

The present disclosure describes compounded compositions for topical administration. A compounded composition according to the present disclosure may include a compounded composition formulated for topical administration to an external surface of a mammal, such as a human. In some embodiments, the compounded composition may be formulated to treat infections or suspected infections of tissues and may be topically administered to surface tissues comprising or adjacent tissues thereof, which may include nails, wounded tissue, mucosal surfaces of the vagina or anus, skin such as on hands, feet, scalp, torso, arms, legs, or other surface. Embodiments of the composition may also be formulated to be applied to nails, a vaginal orifice, or anal orifice. Such a composition may be referred to herein as a compounded composition.

The compounded composition may generally include an antimicrobial agent comprising one or more pharmaceuticals drugs. Some embodiments may include combinations of active agents described herein without the antimicrobial agent. The compounded composition may include a carrier comprising one or more carrier components. Unless stated otherwise, carrier is intended to include carrier component such that use of the term carrier may refer to a component of the carrier and is not restrictive in that other carrier components may be included and the carrier component referred to as the carrier need not form a complete carrier. Indeed, a carrier may include a thickening agent added to a commercially available medicated carrier solution, lotion, or cream, alone or together with other carriers, to formulate a carrier with respect to the compounded composition. Carrier may also be used interchangeably with the term base. The carrier may be liquid, semi-liquid, or solid. For example, the carrier may include an aqueous, organic, or inorganic solution, which may include a dispersion or suspension, cream, gel, ointment, lotion, emulsion, powder, or paste. The compounded composition may be formulated to treat microbial infections, such as infections of the skin, nails, mucosal surfaces, and potentially internalized infections, e.g., via transdermal administration of antimicrobial agents.

Embodiments of the compounded composition may include an antimicrobial agent selected from an antibacterial agent, antifungal agent, or both. In one embodiment, the antibacterial agent may include an antiviral agent. As introduced above, the compounded composition may comprise the antimicrobial agent alone or in combination with one or more additional active agents selected from antibacterial agent, antifungal agent, an anti-inflammatory agent, a steroid, an anti-allergic agent, an antimicrobial agent, an antidepressant agent, a stimulant agent, a disinfectant agent, an anticonvulsant agent, a local anesthetic agent, or combinations thereof. In one embodiment, the compounded composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In some embodiments, the compounded composition may comprise the antimicrobial agent including an antifungal agent, antibacterial agent, or both alone or in combination with a steroid agent, antiviral agent, NSAID agent, antidepressant agent, anticonvulsant agent, analgesic agent, opiate or opioid agonist agent, keratolytic agent, or combination thereof.

It is to be appreciated that recitations herein of a particular active pharmaceuticals include pharmaceutically acceptable salts thereof whether or not specifically recited as such. Similarly, recitation of a particular active pharmaceutical salt may also include other pharmaceutically acceptable salts thereof whether or not specifically recited as such.

In various embodiments, the antimicrobial agent comprises an antifungal agent, alone or in combination with an antibacterial agents, wherein the an antifungal agent includes one or more antifungal pharmaceutical drugs selected from one or more categories of antifungal agent including azoles (imidazoles), antimetabolites, allylamines, morpholine, glucan synthesis inhibitors (echinocandins), polyenes, benoxaaborale; other antifungal/onychomycosis agents, and new classes of antifungal/onychomycosis agents. For example, the antifungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or a combination thereof. In some embodiments, the antibacterial agent is selected from one or more azoles. In one example, the antifungal agent is selected from itraconazole, voriconazole, or combination thereof. In various embodiments, the antimicrobial agent comprises an antifungal agent selected from one or more antifungals comprising fluconazole, itraconazole, voriconazole, amphotericin, nystatin, clotrimazole, econazole, or ketoconazole.

In various embodiments, the compounded composition may comprise between approximately 0.01% and approximately 20% by weight antifungal agent, such as between approximately 0.01% and approximately 5%, approximately 0.01% and approximately 3%, approximately 0.01% and approximately 1%, approximately 0.01% and approximately 0.25%, approximately 0.01% and approximately 0.15%, approximately 0.05% and approximately 0.15%, between 0.1% and 10%, approximately 0.1% and approximately 0.5%, approximately 0.1% and approximately 0.2%, approximately 0.2% and approximately 0.8%, approximately 0.2% and approximately 0.6%, approximately 0.2% and approximately 0.4%, approximately 0.3% and approximately 1%, approximately 0.3% and approximately 0.8%, approximately 0.3% and approximately 0.6%, approximately 0.4% and approximately 1%, approximately 0.5% and approximately 1%, approximately 0.5% and approximately 8%, approximately 0.6% and approximately 1%, approximately 0.6% and approximately 0.8%, approximately 0.8% and approximately 1%, approximately 1% and approximately 3%, approximately 1% and approximately 10%, approximately 1% and approximately 8%, approximately 1% and approximately 5%, approximately 1% and approximately 3%, approximately 3% and approximately 10%, approximately 3% and approximately 8%, approximately 3% and approximately 5%, between 5% and 10%, approximately 5% and approximately 8%, approximately 6% and approximately 10%, approximately 6% and approximately 8%, approximately 7% and approximately 10%, approximately 8% and approximately 10%, approximately 10% and approximately 20%, approximately 10% and approximately 15%, approximately 10% and approximately 12%, approximately 12% and approximately 15%, or between approximately 15% and approximately 20% antifungal agent by weight. In some embodiments, the amount of antifungal agent by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the compounded composition.

In various embodiments, the compounded composition comprises an antimicrobial agent including an antifungal agent alone or in combination with an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a local anesthetic agent, or combination thereof, which may include one or more active pharmaceutical drugs of selected components or agents. In one embodiment, the compounded composition includes one or more additional active agents selected from one or more anticonvulsants, nerve depressants, muscle relaxants, NMDA (N-Methyl-D-aspartate) receptor antagonists, opiate or opioid agonists, antidepressants, and/or other actives. In some embodiments, the compounded composition comprises an antifungal agent alone or in combination with an antibacterial agent, antiviral agent, steroid agent, NSAID agent, antidepressant agent, anticonvulsant agent, analgesic agent, opioid agent, keratolytic agent, or combination thereof, which may include one or more active pharmaceutical drugs of selected agents or agents. In an above or another embodiment, the antimicrobial agent may further comprise an antibacterial agent comprising one or more antibacterial pharmaceutical drugs, such as those identified herein.

The antimicrobial agent may comprise an antibacterial agent alone or in combination with an antifungal agent. In some embodiments, the antibacterial agent comprises one or more enicillins, cephalosporins, fluoroquinolones, aminoglycosides, monobactams, carbapenems, macrolides, other antibacterial, or combination thereof. For example, the antibacterial agent may include one or more antibacterial pharmaceutical drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, methicillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilamide, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the antibacterial agent is selected from mupirocin, gentamycin, tobramycin, or combinations thereof. In one embodiment, the antibacterial agent includes an aminoglycoside.

In various embodiments, the one or more antimicrobial agents comprises an antibacterial agent selected from one or more antibacterials comprising vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/trimethoprim. In one example, the compounded composition comprises linezolid, levofloxacin, ciprofloxacin, or combination thereof.

In an example, the antimicrobial agent includes a commercially available mupirocin, such as Mupirocin Ointment; Mupirocin Cream; or bulk powder. Mupirocin Ointment may be a mupirocin 2.0% ointment wherein each gram of ointment contains 20 mg mupirocin in a bland water miscible ointment base (polyethylene glycol ointment, NF) comprising polyethylene glycol 400 and polyethylene glycol 3350. Mupirocin Cream may include mupirocin 2.0% cream USP containing 2.15% w/w mupirocin calcium USP (equivalent to 2% mupirocin free acid) in an oil- and water-based emulsion supplied in 15-gram and 30-gram tubes.

In various embodiments, the compounded composition may comprise between approximately 0.01% and approximately 20% by weight antibacterial agent, such as between approximately 0.01% and approximately 5%, approximately 0.01% and approximately 3%, approximately 0.01% and approximately 1%, approximately 0.01% and approximately 0.25%, approximately 0.01% and approximately 0.15%, approximately 0.05% and approximately 0.15%, between 0.1% and 10%, approximately 0.1% and approximately 0.5%, approximately 0.1% and approximately 0.2% approximately 0.2% and approximately 0.8%, approximately 0.2% and approximately 0.6%, approximately 0.2% and approximately 0.4%, approximately 0.3% and approximately 1%, approximately 0.3% and approximately 0.8%, approximately 0.3% and approximately 0.6%, approximately 0.4% and approximately 1%, approximately 0.5% and approximately 1%, approximately 0.5% and approximately 8%, approximately 0.6% and approximately 1%, approximately 0.6% and approximately 0.8%, approximately 0.8% and approximately 1%, approximately 1% and approximately 3%, approximately 1% and approximately 10%, approximately 1% and approximately 8%, approximately 1% and approximately 5%, approximately 1% and approximately 3%, approximately 3% and approximately 10%, approximately 3% and approximately 8%, approximately 3% and approximately 5%, between 5% and 10%, approximately 5% and approximately 8%, approximately 6% and approximately 10%, approximately 6% and approximately 8%, approximately 7% and approximately 10%, approximately 8% and approximately 10%, approximately 10% and approximately 20%, approximately 10% and approximately 15%, approximately 10% and approximately 12%, approximately 12% and approximately 15%, or between approximately 15% and approximately 20% antibacterial agent by weight. In some embodiments, the amount of antibacterial agent by weight may be approximately 0.01%, approximately 0.05%, approximately 0.1%, approximately 0.5%, approximately 1%, approximately 1.5%, approximately 2%, approximately 2.5%, approximately 3%, approximately 3.5%, approximately 4%, approximately 4.5%, approximately 5%, approximately 5.5%, approximately 6%, approximately 6.5%, approximately 7%, approximately 7.5%, approximately 8%, approximately 8.5%, approximately 9%, approximately 9.5%, approximately 10%, approximately 11%, approximately 12%, approximately 13%, approximately 14%, approximately 15%, approximately 17%, approximately 19%, approximately 20%, or any other percentage between approximately 0.01% and 20% by weight of the compounded composition.

In some examples, a compounded composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, from approximately 3.0% w/w to approximately 7.0% w/w, or from approximately 4.0% w/w to approximately 7.0% w/w of an antifungal agent identified herein. For example, the compounded composition may comprise itraconazole, voriconazole, fluconazole, or combination thereof. In an example, the compounded composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, from approximately 3.0% w/w to approximately 7.0% w/w, or from approximately 4.0% w/w to approximately 7.0% w/w of a first antifungal agent identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a second antifungal agent identified herein.

In one example, a compounded composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antibacterial agent identified herein. In another example, the compounded composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a first antibacterial agent identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of a second antibacterial agent identified herein. For example, the compounded composition may comprise mupirocin and tobramycin, mupirocin and doxycycline, mupirocin and doxycycline hyclate, mupirocin and azithromycin, or mupirocin, doxycycline, and ketoconazole.

In one example, a compounded composition comprises from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antifungal agent identified herein and from approximately 0.3% w/w to approximately 3% w/w, approximately 0.5% w/w to approximately 2.5% w/w, approximately 1.0% w/w to approximately 9.0% w/w, approximately 2.0% w/w to approximately 8.0% w/w, approximately 3.0% w/w to approximately 7.0% w/w, or from approximately 4.0% w/w to approximately 7.0% w/w of an antibacterial agent identified herein. For example, the antibacterial agent may comprise doxycycline, tobramycin, ciprofloxacin, mupirocin, or combination thereof and the antifungal agent may comprise ketoconazole, itraconazole, voriconazole, or combination thereof.

In some embodiments, the topical compounded composition may comprise one or more excipients or additives. In an aspect, excipients or additives include, but are not limited to, the following: solvents, surfactants, humectants, preservatives, flavorings, stabilizers (including antioxidants), binders, and colorants.

In various embodiments, the compounded composition comprises the antibacterial agent alone or in combination with one or more additional active agents selected from an antifungal agent, an antiviral agent, an anti-inflammatory agent, an non-steroidal anti-inflammatory (NSAID) agent, an anti-allergic agent, an antimicrobial agent, an anti-depressant agent, a stimulant agent, a disinfectant agent, an anticonvulsant agent, a local anesthetic agent, or combinations thereof, which may include one or more active pharmaceutical drugs of selected components or agents. In one embodiment, the compounded composition includes additional active agents selected from one or more anticonvulsants, nerve depressants, muscle relaxants, NMDA (N-Methyl-D-aspartate) receptor antagonists, opiate or opioid agonists, antidepressants, and/or other active agents. In some embodiments, the compounded composition may comprise the antibacterial agent alone or in combination with an antifungal agent, steroid agent, antiviral agent, NSAID agent, antidepressant agent, anticonvulsant agent, analgesic agent, opioid agent, keratolytic agent, or combination thereof, which may include one or more active pharmaceutical drugs of selected components or agents. In various embodiments, the compounded composition may comprise the antibacterial agent alone or in combination with one or more antifungal agents.

As introduced above, the compounded composition may comprise one or more additional active agents. It will be appreciated that compounded compositions herein may include or specifically exclude additional active agents. It will also be appreciated that compounded compositions may exclude an antimicrobial agent and rather include one or more of the additional active agents described herein.

In an aspect, an antifungal agent or antibacterial agent can comprise a cream or ointment or can comprise a dry powder. In an aspect, the dry powder can be obtained from crushed tablets comprising an antifungal agent or from a container comprising the antifungal agent as a dry powder. In an aspect, an antifungal agent can be pure or substantially pure and can be obtained from a bulk source. In an aspect, an antifungal agent can be commercially available as, for example, a tablet, a cream, an ointment, or a powder.

A. Compounded Compositions for Treating an Infection

1. A First Antibacterial Agent and a Second Antibacterial Agent

Disclosed herein is a compounded composition comprising a therapeutically effective amount of a first antibacterial agent and a therapeutically effective amount of a second antibacterial agent. A disclosed compounded composition can comprise a dry powder formulation or can comprise a cream or ointment.

In an aspect, a disclosed compounded composition can comprise from about 1.0% w/w to about 9.0% w/w, from about 2.0% w/w to about 8.0% w/w, from about 3.0% w/w to about 7.0% w/w, or from about 4.0% w/w to about 7.0% w/w of the first antibacterial agent. In an aspect, a disclosed compounded composition can comprise from about 1.0% w/w to about 9.0% w/w, from about 2.0% w/w to about 8.0% w/w, from about 3.0% w/w to about 7.0% w/w, or from about 4.0% w/w to about 7.0% w/w of the second antibacterial agent.

The antibacterial agent may include one or more antibacterials or pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin.

In an aspect, the first antibacterial agent can comprise mupirocin. In an aspect, the first antibacterial agent can comprise mupirocin. Disclosed herein is a compounded composition comprising a therapeutically effective amount of mupirocin and a therapeutically effective amount of an antibacterial agent. In an aspect, a disclosed compounded composition comprising mupirocin and an antibacterial agent can comprise a dry powder formulation or can comprise a cream or ointment.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.7% w/w, or about 1.8% w/w mupirocin. In an aspect, a disclosed compounded composition comprising mupirocin and an antibacterial agent can comprise from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the antibacterial agent. In an aspect, a disclosed compounded composition comprising mupirocin and an antibacterial agent can comprise about 2.5% w/w, about 5.0% w/w, about 6.0%, or about 7.5% w/w of the antibacterial agent (which is in addition to the amount of mupirocin). Greater or lesser amounts of mupirocin or doxycycline may be used, e.g., less than about 4%, about 3%, about 2%, or about 1% doxycycline.

In an aspect, the second antibacterial agent can comprise tobramycin or a pharmaceutically acceptable salt thereof. In an aspect, a disclosed compounded composition can comprise mupirocin and tobramycin. In an aspect, the mupirocin can comprise a cream or ointment (for example, a mupirocin 2.0% cream or ointment) and the tobramycin or a pharmaceutically acceptable salt thereof can comprise a dry powder. In an aspect, a disclosed compounded composition can comprise about 1.775% w/w mupirocin and about 7.5% w/w tobramycin or a pharmaceutically acceptable salt thereof.

In an aspect, the second antibacterial agent can comprise tobramycin sulfate. In an aspect, a disclosed compounded composition can comprise mupirocin and tobramycin sulfate. In an aspect, the mupirocin can comprise a cream or ointment (for example, a mupirocin 2.0% cream or ointment) and the tobramycin sulfate can comprise a dry powder.

In an aspect, the second antibacterial agent can comprise doxycycline or a pharmaceutically acceptable salt thereof. In an aspect, a disclosed compounded composition can comprise mupirocin and doxycycline or a pharmaceutically acceptable salt thereof. In an aspect, the mupirocin can comprise a cream or ointment (for example, a mupirocin 2.0% cream or ointment) and the doxycycline or a pharmaceutically acceptable salt thereof can comprise a dry powder. In an aspect, a disclosed compounded composition can comprise about 1.756% w/w mupirocin and about 5.0% w/w doxycycline or a pharmaceutically acceptable salt thereof.

In an aspect, the second antibacterial agent can comprise doxycycline hyclate. In an aspect, a disclosed compounded composition can comprise mupirocin and doxycycline hyclate. In an aspect, the mupirocin can comprise a cream or ointment (for example, a mupirocin 2.0% cream or ointment) and the doxycycline hyclate can comprise a dry powder.

In an aspect, the second antibacterial agent can comprise azithromycin. In an aspect, a disclosed compounded composition can comprise mupirocin and azithromycin. In an aspect, the mupirocin can comprise a cream or ointment (for example, a mupirocin 2.0% cream or ointment) and the azithromycin can comprise a dry powder. In an aspect, a disclosed compounded composition can comprise about 1.8% w/w mupirocin and about 5.0% w/w azithromycin.

In an aspect, the first antibacterial agent can comprise mupirocin and the second antibacterial agent can comprise one or more of bacitracin, colistimethate, piperacillin-tazobactam, polymyxin B, streptomycin or pharmaceutically acceptable salts thereof. The mupirocin can comprise a cream or ointment (for example, a mupirocin 2.0% cream or ointment) and the second antibacterial agent may comprise a dry powder. In one embodiment, the second antibacterial agent comprises bacitracin. In one example, the bacitracin agent comprises bacitracin for injection (USP). In another embodiment, the second antibacterial agent comprises colistimethate. In one example, the colistimethate comprises colistimethate for injection. In a further example, the colistimethate includes colistimethate for injection comprising colistimethate sodium or pentasodium colistin methanesulfonate. In another embodiment, the second antibacterial agent comprises piperacillin-tazobactam. In one example, the piperacillin-tazobactam comprises piperacillin-tazobactam for injection USP. In a further example, the piperacillin-tazobactam comprises piperacillin-tazobactam for injection USP selected from 2.25 gram, 3.375 gram, and 4.5 gram vials. In another embodiment, the second antibacterial agent comprises polymyxin B. In one example, the polymyxin B comprises Polymyxin B for Injection USP. In another embodiment, the second antibacterial agent comprises streptomycin. In one example, the streptomycin comprises streptomycin for injection USP. In a further example, the streptomycin comprises streptomycin sulfate for injection USP. In these or another embodiment, the second antibacterial agent comprises streptomycin and doxycycline.

In an aspect, a disclosed compounded composition can comprise a therapeutically effective amount of one or more additional antimicrobial agents. In an aspect, the additional antimicrobial agent can be an antibacterial agent. In an aspect, the additional antimicrobial agent can be an antifungal agent.

In an aspect, the antifungal agent can comprise ketoconazole. In an aspect, a disclosed compounded composition can comprise mupirocin, doxycycline or a pharmaceutically acceptable salt thereof), and ketoconazole. In an aspect, the mupirocin can comprise a cream or ointment (for example, a mupirocin 2% cream or ointment), the doxycycline or a pharmaceutically acceptable salt thereof can comprise a dry powder, and the ketoconazole can comprise a dry powder. In an aspect, a disclosed compounded composition can comprise about 1.6% w/w mupirocin, about 5.0% w/w doxycycline or a pharmaceutically acceptable salt thereof, and about 5.0% w/w ketoconazole.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

Disclosed herein is a compounded composition comprising a therapeutically effective amount of a first antibacterial agent, a therapeutically effective amount of a second antibacterial agent, and a therapeutically effective amount of an antifungal agent. In an aspect, a disclosed compounded composition can comprise mupirocin, doxycycline or a pharmaceutically acceptable salt thereof, and ketoconazole. In an aspect, the mupirocin can comprise a cream or ointment, the doxycycline can comprise a dry powder, and the ketoconazole can comprise a dry powder. In an aspect, a disclosed compounded composition can comprise about 1.6% w/w mupirocin, about 5.0% w/w doxycycline or a pharmaceutically acceptable salt thereof, and about 5.0% w/w ketoconazole.

2. Mupirocin and an Antibacterial Agent

Disclosed herein is a compounded composition comprising a therapeutically effective amount of mupirocin and a therapeutically effective amount of an antibacterial agent. In an aspect, a disclosed compounded composition comprising mupirocin and an antibacterial agent can comprise a dry powder formulation or can comprise a cream or ointment.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.756% w/w, or about 1.77% w/w, or about 1.775% w/w, or about 1.8% w/w mupirocin. In an aspect, a disclosed compounded composition comprising mupirocin and an antibacterial agent can comprise from about 1.0% w/w to about 9.0% w/w, from about 2.0% w/w to about 8.0% w/w, from about 3.0% w/w to about 7.0% w/w, from about 4.0% w/w to about 6.0% w/w, or about 5.0% w/w of the antibacterial agent. In an aspect, a disclosed compounded composition comprising mupirocin and an antibacterial agent can comprise about 2.5% w/w, about 5.0% w/w, or about 7.5% w/w of the antibacterial agent.

Disclosed herein is a compounded composition comprising a therapeutically effective amount of mupirocin and a therapeutically effective amount of an antibacterial agent (in addition to mupirocin) comprising one or more antibacterials. A disclosed compounded composition can comprise a dry powder formulation, a cream or ointment, or combinations thereof. For example, the antibacterial agent may comprise a dry powder compounded with mupirocin cream or mupirocin ointment, which include both mupirocin cream and mupirocin ointment. The dry powder formulation, cream, ointment, or combination thereof may be formulated for mixing with an aqueous diluent for irrigation, e.g., administration to infected skin in a footbath. In some embodiments, a compounded composition may include mupirocin cream or mupirocin ointment compounded with the second antibacterial agent comprising a dry powder to form a compounded cream or ointment, which may be applied directly to infected skin or may be further combined with an aqueous diluent for irrigation administration, e.g., in a footbath.

In various embodiments, mupirocin comprises a mupirocin cream or mupirocin ointment. The mupirocin cream may be a 2% mupirocin cream. The mupirocin ointment may be a 2% mupirocin ointment. In an aspect, the compounded composition may include from about 20% to about 98%, about 60% to about 90%, about 70% to about 88%, about 75% to about 88% mupirocin 2% cream or mupirocin 2% ointment w/w, alone or in combination.

The antibacterial agent may include one or more antibacterials or pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin.

In an aspect, the antibacterial agent can comprise tobramycin or a pharmaceutically acceptable salt thereof. In an aspect, a disclosed compounded composition can comprise mupirocin and tobramycin. In an aspect, the mupirocin can comprise a cream or ointment (for example, a mupirocin 2% cream or ointment) and the tobramycin or a pharmaceutically acceptable salt thereof can comprise a dry powder. In an aspect, a disclosed compounded composition can comprise about 1.775% w/w mupirocin and about 7.5% w/w tobramycin or a pharmaceutically acceptable salt thereof.

In an aspect, the antibacterial agent can comprise tobramycin sulfate. In an aspect, a disclosed compounded composition can comprise mupirocin and tobramycin sulfate. In an aspect, the mupirocin can comprise a cream or ointment (for example, a mupirocin 2% cream or ointment) and the tobramycin sulfate can comprise a dry powder. In various embodiments, the antibacterial agent can comprise one or more of bacitracin, colistimethate, piperacillin-tazobactam, polymyxin B, streptomycin or pharmaceutically acceptable salts thereof. The mupirocin can comprise a cream or ointment (for example, a mupirocin 2% cream or ointment) and the second antibacterial agent may comprise a dry powder. In one embodiment, the antibacterial agent comprises bacitracin. In one example, the bacitracin comprises Bacitracin for Injection (USP). In another embodiment, the antibacterial agent comprises colistimethate. In one example, the colistimethate comprises Colistimethate for Injection USP. In a further example, the colistimethate includes Colistimethate for Injection comprising colistimethate sodium or pentasodium colistin methanesulfonate. In another embodiment, the antibacterial agent comprises piperacillin-tazobactam. In one example, the piperacillin-tazobactam comprises Piperacillin-Tazobactam for Injection USP. In a further example, the piperacillin-tazobactam comprises Piperacillin-Tazobactam for Injection USP selected from 2.25 gram, 3.375 gram, and 4.5 gram vials. In another embodiment, the antibacterial agent comprises polymyxin B. In one example, the polymyxin B comprises Polymyxin B for Injection USP. In another embodiment, the antibacterial agent comprises streptomycin. In one example, the streptomycin comprises Streptomycin for Injection USP. In a further example, the streptomycin comprises Streptomycin Sulfate for Injection USP. In these or another embodiment, the antibacterial agent comprises streptomycin and doxycycline.

Disclosed herein is a compounded composition comprising a therapeutically effective amount of mupirocin and a therapeutically effective amount of streptomycin or a pharmaceutically acceptable salt thereof. A disclosed compounded composition comprising mupirocin and streptomycin or a salt thereof can comprise a dry powder formulation or can comprise a cream or ointment. In an aspect, a disclosed compounded composition comprising mupirocin and streptomycin or salt thereof can comprise from about 1.0% w/w to about 3.0% w/w, from about 1.2% w/w to about 2.5% w/w, from about 1.4% w/w to about 2.3% w/w, from about 1.4% w/w to about 2.2% w/w, from about 1.5% w/w to about 2.1% w/w, from about 1.6% w/w to about 2.0% w/w, from about 1.7% w/w to about 2.0% w/w, or from about 1.8% w/w to about 2.0% w/w mupirocin. In an aspect, a disclosed compounded composition comprising mupirocin and streptomycin or salt thereof can comprise from about 1.0% w/w to about 5.0% w/w, from about 1.0% w/w to about 3.0% w/w, or from about 1.5% w/w to about 2.5% w/w streptomycin or a pharmaceutically acceptable thereof. In an aspect, a disclosed compounded composition comprising mupirocin and streptomycin or salt thereof can comprise from about 1.8% w/w to about 2.0% w/w mupirocin and from about 3.0% w/w to about 4.0% w/w streptomycin or a pharmaceutically acceptable thereof. In an aspect, a disclosed compounded composition comprising mupirocin and streptomycin or salt thereof can comprise about 1.7% w/w mupirocin and about 4.0% w/w streptomycin or a pharmaceutically acceptable salt thereof.

Disclosed herein is a compounded composition comprising a therapeutically effective amount of mupirocin and an antibacterial agent comprising a therapeutically effective amount of doxycycline or a pharmaceutically acceptable salt thereof. The antibacterial agent may further include one or more additional antibacterials, such as those identified herein. A disclosed compounded composition comprising mupirocin and doxycycline or a salt thereof can comprise a dry powder formulation or can comprise a cream or ointment. In an aspect, a disclosed compounded composition comprising mupirocin and doxycycline or a salt thereof can comprise from about 1.0% w/w to about 3.0% w/w mupirocin. In an aspect, a disclosed compounded composition comprising mupirocin and doxycycline or a salt thereof can comprise about 1.7% w/w mupirocin. In an aspect, a disclosed compounded composition comprising mupirocin and doxycycline or a salt thereof can comprise from about 4.0% to about 6.0% w/w doxycycline or a pharmaceutically acceptable salt thereof. In an aspect, a disclosed compounded composition comprising mupirocin and doxycycline or a salt thereof can comprise about 5.0% w/w doxycycline or a pharmaceutically acceptable salt thereof. In an aspect, a disclosed compounded composition comprising mupirocin and doxycycline or a salt thereof can comprise about 1.7% w/w mupirocin and about 5.0% w/w doxycycline or a pharmaceutically acceptable salt thereof.

Disclosed herein is a compounded composition comprising a therapeutically effective amount of mupirocin and a therapeutically effective amount of tobramycin or a pharmaceutically acceptable salt thereof. A disclosed compounded composition comprising mupirocin and tobramycin or a salt thereof can comprise a dry powder formulation or can comprise a cream or ointment. In an aspect, a disclosed compounded composition comprising mupirocin and tobramycin or a salt thereof can comprise from about 1.0% w/w to about 3.0% w/w of mupirocin. In an aspect, a disclosed compounded composition comprising mupirocin and tobramycin or a salt thereof can comprise about 1.775% w/w of mupirocin. In an aspect, a disclosed compounded composition comprising mupirocin and tobramycin or a salt thereof can comprise from about 7.0% to about 9.0% w/w of tobramycin or a pharmaceutically acceptable salt thereof. In an aspect, a disclosed compounded composition comprising mupirocin and tobramycin or a salt thereof can comprise about 7.5% w/w of tobramycin or a pharmaceutically acceptable salt thereof. In an aspect, a disclosed compounded composition comprising mupirocin and tobramycin or a salt thereof can comprise about 1.775% w/w mupirocin and about 7.5% w/w tobramycin or a pharmaceutically acceptable salt thereof. In an aspect, a disclosed compounded composition comprising mupirocin and tobramycin or a pharmaceutically acceptable salt thereof can comprise ketoconazole or fluconazole.

Disclosed herein is a compounded composition comprising a therapeutically effective amount of mupirocin and a therapeutically effective amount of doxycycline or a pharmaceutically acceptable salt thereof. A disclosed compounded composition comprising mupirocin and doxycycline or a salt thereof can comprise a dry powder formulation or can comprise a cream or ointment. In an aspect, a disclosed compounded composition comprising mupirocin and doxycycline or a salt thereof can comprise from about 1.0% w/w to about 3.0% w/w mupirocin. In an aspect, a disclosed compounded composition comprising mupirocin and doxycycline or a salt thereof can comprise about 1.756% w/w mupirocin. In an aspect, a disclosed compounded composition comprising mupirocin and doxycycline or a salt thereof can comprise from about 4.0% to about 6.0% w/w doxycycline or a pharmaceutically acceptable salt thereof. In an aspect, a disclosed compounded composition comprising mupirocin and doxycycline or a salt thereof can comprise about 5.0% w/w doxycycline or a pharmaceutically acceptable salt thereof. In an aspect, a disclosed compounded composition comprising mupirocin and doxycycline or a salt thereof can comprise about 1.756% w/w mupirocin and about 5.0% w/w doxycycline or a pharmaceutically acceptable salt thereof.

In an aspect, a disclosed compounded composition comprising mupirocin and doxycycline or a salt thereof can comprise ketoconazole. In an aspect, a disclosed compounded composition can comprise about 1.6% w/w mupirocin, about 5.0% w/w doxycycline or a pharmaceutically acceptable salt thereof, and about 5.0% w/w ketoconazole. In an aspect, a disclosed compounded composition can comprise about 1.8% w/w mupirocin, about 2.5% w/w doxycycline or a pharmaceutically acceptable salt thereof, and about 2.5% w/w ketoconazole.

Disclosed herein is a compounded composition comprising a therapeutically effective amount of mupirocin and a therapeutically effective amount of azithromycin. A disclosed compounded composition comprising mupirocin and azithromycin can comprise a dry powder formulation or can comprise a cream or ointment. In an aspect, a disclosed compounded composition comprising mupirocin and azithromycin can comprise from about 1.0% w/w to about 3.0% w/w mupirocin. In an aspect, a disclosed compounded composition comprising mupirocin and azithromycin can comprise about 1.8% w/w mupirocin. In an aspect, a disclosed compounded composition comprising mupirocin and azithromycin can comprise from about 4.0% w/w to about 6.0% w/w azithromycin. In an aspect, a disclosed compounded composition comprising mupirocin and azithromycin can comprise about 5.0% w/w azithromycin. In an aspect, a disclosed compounded composition can comprise about 1.8% w/w mupirocin and about 5.0% w/w azithromycin.

Disclosed herein is a compounded composition comprising a therapeutically effective amount of mupirocin and a therapeutically effective amount of ciprofloxacin or a pharmaceutically acceptable salt thereof. A disclosed compounded composition comprising mupirocin and ciprofloxacin or a salt thereof can comprise a dry powder formulation or can comprise a cream or ointment. In an aspect, a disclosed compounded composition comprising mupirocin and ciprofloxacin or salt thereof can comprise from about 1.0% w/w to about 3.0% w/w, from about 1.2% w/w to about 2.5% w/w, from about 1.4% w/w to about 2.3% w/w, from about 1.4% w/w to about 2.2% w/w, from about 1.5% w/w to about 2.1% w/w, from about 1.6% w/w to about 2.0% w/w, from about 1.7% w/w to about 2.0% w/w, or from about 1.8% w/w to about 2.0% w/w mupirocin. In an aspect, a disclosed compounded composition comprising mupirocin and ciprofloxacin or salt thereof can comprise from about 1.0% w/w to about 5.0% w/w, from about 1.0% w/w to about 3.0% w/w, or from about 1.5% w/w to about 2.5% w/w ciprofloxacin or a pharmaceutically acceptable thereof. In an aspect, a disclosed compounded composition comprising mupirocin and ciprofloxacin or salt thereof can comprise from about 1.8% w/w to about 2.0% w/w mupirocin and from about 1.0% w/w to about 3.0% w/w ciprofloxacin or a pharmaceutically acceptable thereof. In an aspect, a disclosed compounded composition comprising mupirocin and ciprofloxacin or salt thereof can comprise about 1.95% w/w mupirocin and about 2.0% w/w ciprofloxacin or a pharmaceutically acceptable salt thereof.

Disclosed herein is a compounded composition comprising a therapeutically effective amount of mupirocin and a therapeutically effective amount of clindamycin or a pharmaceutically acceptable salt thereof. In an aspect, a disclosed compounded composition comprising mupirocin and clindamycin or a salt thereof can comprise a dry powder formulation or can comprise a cream or ointment. In an aspect, a disclosed compounded composition comprising mupirocin and clindamycin or a salt thereof can comprise from about 1.0% w/w to about 3.0% w/w mupirocin. In an aspect, a disclosed compounded composition comprising mupirocin and clindamycin or a salt thereof can comprise about 1.88% w/w mupirocin. In an aspect, a disclosed compounded composition can comprise from about 4.0% to about 6.0% w/w clindamycin or a pharmaceutically acceptable salt thereof. In an aspect, a disclosed compounded composition comprising mupirocin and clindamycin or a salt thereof can comprise about 5.0% w/w clindamycin or a pharmaceutically acceptable salt thereof. In an aspect, a disclosed compounded composition comprising mupirocin and clindamycin or a salt thereof can comprise about 1.88% w/w mupirocin and about 5.0% w/w clindamycin or a pharmaceutically acceptable salt thereof.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition can comprise a therapeutically effective amount of one or more additional antimicrobial agents. In an aspect, the additional antimicrobial agent can be an antibacterial agent. In an aspect, the additional antimicrobial agent can be an antifungal agent.

3. An Antibacterial Agent and an Antifungal Agent

Disclosed herein is a compounded composition comprising a therapeutically effective amount of an antibacterial agent and a therapeutically effective amount of an antifungal agent. A disclosed compounded composition comprising the antibacterial agent and the antifungal agent can comprise a dry powder formulation or can comprise a cream or ointment. The antibacterial agent may include one or more antibacterials pharmaceutically acceptable salts thereof selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, meticillin, metronidazole, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin (piperacillin/tazobactam), pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, streptomycin, sulbactam, sulfacetamide, sulfamethizole, sulfamethoxazole, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or pharmaceutically acceptable salts thereof, or a combination thereof. In an aspect, fluoroquinolones can comprise enoxacin, ciprofloxacin, norfloxacin, ofloxacin, levofloxacin, trovafloxacin, gatifloxacin, or moxifloxacin.

The antifungal agent may comprise one or more antifungals pharmaceutically acceptable salts thereof selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole. The antifungal agent may be in addition to or instead of the second antibacterial agent.

4. Mupirocin and an Antifungal Agent

Disclosed herein is a compounded composition comprising a therapeutically effective amount of mupirocin and a therapeutically effective amount of an antifungal agent. A disclosed compounded composition comprising mupirocin and the antifungal agent can comprise a dry powder formulation or can comprise a cream or ointment.

The antifungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole. The antifungal agent may be in addition to or instead of the second antibacterial agent.

In an aspect, a disclosed compounded composition comprising mupirocin and an antifungal agent can comprise from about 1.0% w/w to about 3.0% w/w mupirocin. A disclosed compounded composition comprising mupirocin and the antifungal agent can comprise a dry powder formulation or can comprise a cream or ointment. In an aspect, a disclosed compounded composition comprising mupirocin and an antifungal agent can comprise about 1.6% w/w, or about 1.7% w/w, or about 1.8% w/w mupirocin. In an aspect, a disclosed compounded composition comprising mupirocin and an antifungal agent can comprise from about 1.0% w/w to about 9.0% w/w or from about 6.0% w/w to about 8.0% w/w of an antifungal agent. In an aspect, a disclosed compounded composition comprising mupirocin and an antifungal agent can comprise about 2.5% w/w, about 5.0% w/w, or about 7.5% w/w of an antifungal agent.

Disclosed herein is a compounded composition comprising a therapeutically effective amount of mupirocin and a therapeutically effective amount of ketoconazole. In an aspect, a disclosed compounded composition comprising mupirocin and ketoconazole can comprise a dry powder formulation or can comprise a cream or ointment. In an aspect, a disclosed compounded composition comprising mupirocin and ketoconazole can comprise from about 1.0% w/w to about 3.0% w/w mupirocin. In an aspect, a disclosed compounded composition comprising mupirocin and ketoconazole can comprise about 1.77% w/w mupirocin. In an aspect, a disclosed compounded composition comprising mupirocin and ketoconazole can comprise from about 6.5% w/w to about 8.5% w/w ketoconazole. In an aspect, a disclosed compounded composition comprising mupirocin and ketoconazole can comprise about 7.5% w/w ketoconazole. In an aspect, a disclosed compounded composition comprising mupirocin and ketoconazole can comprise about 1.77% w/w mupirocin and about 7.5% w/w ketoconazole.

Disclosed herein is a compounded composition comprising a therapeutically effective amount of mupirocin and a therapeutically effective amount of nystatin. A disclosed compounded composition comprising mupirocin and nystatin can comprise a dry powder formulation or can comprise a cream or ointment. In an aspect, a disclosed compounded composition comprising mupirocin and nystatin can comprise from about 1.0% w/w to about 3.0% w/w mupirocin. In an aspect, a disclosed compounded composition comprising mupirocin and nystatin can comprise about 1.60% w/w mupirocin. In an aspect, a disclosed compounded composition comprising mupirocin and nystatin can comprise from about 15,000 units per gram to about 25,000 units per gram nystatin. In an aspect, a disclosed compounded composition comprising mupirocin and nystatin can comprise about 20,000 units per gram nystatin. In an aspect, a disclosed compounded composition comprising mupirocin and nystatin can comprise about 1.60% w/w mupirocin and about 20,000 units per gram nystatin.

In various embodiments, the antifungal agent may comprise one or more of ketoconazole, voriconazole, or amphotericin B. The antifungal agent may comprise a powder including the antifungal or a pharmaceutically acceptable salt thereof. In one embodiment, the antifungal agent comprises voriconazole. The voriconazole may comprise a dry powder compounded with mupirocin cream or mupirocin ointment. The voriconazole may comprise Voriconazole for Injection. In a further embodiment, the voriconazole comprises Voriconazole for Injection in 200 mg vials of lyophilized powder. In one embodiment, the antifungal agent comprises amphotericin B. The amphotericin B may comprise Amphotericin B for Injection USP. In one embodiment, the antifungal agent comprises ketoconazole.

In various embodiments, first antibacterial comprises about 1% to about 1.9% w/w mupirocin and the antifungal comprises from about 0.2% to about 6% w/w voriconazole. In one example, the compounded composition comprises about 1.71% w/w mupirocin and 0.8% w/w voriconazole. The mupirocin may be mupirocin 2% cream or ointment in an amount approximately 85.7% w/w of the compounded composition and the voriconazole may include voriconazole for injection in an amount about 0.8% w/w of the compounded composition.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

In an aspect, a disclosed compounded composition can comprise a therapeutically effective amount of one or more additional antimicrobial agents. In an aspect, the additional antimicrobial agent can be an antibacterial agent. In an aspect, the additional antimicrobial agent can be an antifungal agent. In an aspect, a disclosed compounded composition can comprise mupirocin and a therapeutically effective amount of one or more additional antimicrobial agents, such as additional second antibacterial agents, as noted above. Additionally or alternatively, the additional antimicrobial may include an antifungal agent.

5. Mupirocin, an Antibacterial Agent, and an Antifungal Agent

Disclosed herein is a compounded composition comprising a therapeutically effective amount of mupirocin, a therapeutically effective amount of an antibacterial agent or second antibacterial agent (in addition to mupirocin), and a therapeutically effective amount of an antifungal agent. A disclosed compounded composition comprising mupirocin, an antibacterial agent, and an antifungal agent can comprise a dry powder formulation or can comprise a cream or ointment.

The antifungal agent may comprise one or more antifungals selected from abafungin, albaconazole, amorolfin, amphotericin b, anidulafungin, bifonazole, butenafine, butoconazole, candicidin, caspofungin, ciclopirox, clotrimazole, econazole, fenticonazole, filipin, fluconazole, flucytosine, griseofulvin, haloprogin, hamycin, isavuconazole, isoconazole, itraconazole, ketoconazole, micafungin, miconazole, naftifine, natamycin, nystatin, omoconazole, oxiconazole, polygodial, posaconazole, ravuconazole, rimocidin, sertaconazole, sulconazole, terbinafine, terconazole, tioconazole, tolnaftate, undecylenic acid, voriconazole, or pharmaceutically acceptable salts thereof, or a combination thereof. In an aspect, azoles can comprise clotrimazole, econazole, oxiconazole, ketoconazole, miconazole, sulconazole, fluconazole, itraconazole, or voriconazole. The antifungal agent may be in addition to or instead of the second antibacterial agent.

Disclosed herein is a compounded composition comprising a therapeutically effective amount of mupirocin, a therapeutically effective amount of doxycycline or a pharmaceutically acceptable salt thereof, and a therapeutically effective amount of fluconazole. A disclosed compounded composition comprising mupirocin, doxycycline or a salt thereof, and fluconazole can comprise a dry powder formulation or can comprise a cream or ointment.

In an aspect, a disclosed compounded composition comprising mupirocin, doxycycline or a salt thereof, and fluconazole can comprise from about 1.0% w/w to about 3.0% w/w mupirocin. In an aspect, a disclosed compounded composition comprising mupirocin, doxycycline or a salt thereof, and fluconazole can comprise about 1.655% w/w mupirocin. In an aspect, a disclosed compounded composition comprising mupirocin, doxycycline or a salt thereof, and fluconazole can comprise from about 1.5% w/w to about 3.5% w/w fluconazole. In an aspect, a disclosed compounded composition comprising mupirocin, doxycycline or a salt thereof, and fluconazole can comprise about 2.5% w/w fluconazole. In an aspect, a disclosed compounded composition comprising mupirocin, doxycycline or a salt thereof, and fluconazole can comprise from about 4.0% to about 6.0% w/w doxycycline or a pharmaceutically acceptable salt thereof. In an aspect, a disclosed compounded composition comprising mupirocin, doxycycline or a salt thereof, and fluconazole can comprise about 5.0% w/w doxycycline or a pharmaceutically acceptable salt thereof. In an aspect, a disclosed compounded composition comprising mupirocin, doxycycline or a salt thereof, and fluconazole can comprise about 1.655% w/w mupirocin, about 5.0% w/w doxycycline or a pharmaceutically acceptable salt thereof, and about 2.5% w/w fluconazole.

Disclosed herein is a compounded composition comprising a therapeutically effective amount of mupirocin, a therapeutically effective amount of doxycycline or a pharmaceutically acceptable salt thereof, and a therapeutically effective amount of ketoconazole. A disclosed compounded composition comprising mupirocin, doxycycline or a salt thereof, and ketoconazole can comprise a dry powder formulation or can comprise a cream or ointment.

In an aspect, a disclosed compounded composition comprising mupirocin, doxycycline or a salt thereof, and ketoconazole can comprise from about 1.0% w/w to about 3.0% w/w mupirocin. In an aspect, a disclosed compounded composition comprising mupirocin, doxycycline or salt thereof, and ketoconazole can comprise about 1.6% w/w or about 1.8% w/w mupirocin. In an aspect, a disclosed compounded composition comprising mupirocin, doxycycline or a salt thereof, and ketoconazole can comprise from about 1.5% to about 3.5% w/w or from about 4.0% to about 6.0% w/w doxycycline or a pharmaceutically acceptable salt thereof. In an aspect, a disclosed compounded composition comprising mupirocin, doxycycline or a salt thereof, and ketoconazole can comprise about 2.5% w/w or 5.0% w/w doxycycline or a pharmaceutically acceptable salt thereof. In an aspect, a disclosed compounded composition comprising mupirocin, doxycycline or a salt thereof, and ketoconazole can comprise from about 1.5% w/w to about 3.5% w/w or from about 4.0% to about 6.0% w/w ketoconazole. In an aspect, a disclosed compounded composition comprising mupirocin, doxycycline or a salt thereof, and ketoconazole can comprise about 2.5% w/w or about 5.0% w/w ketoconazole. In an aspect, a disclosed compounded composition comprising mupirocin, doxycycline or salt thereof, and ketoconazole can comprise about 1.6% w/w mupirocin, about 5.0% w/w doxycycline or a pharmaceutically acceptable salt thereof, and about 5.0% w/w ketoconazole. In an aspect, a disclosed compounded composition comprising mupirocin, doxycycline or a salt thereof, and ketoconazole can comprise about 1.8% w/w mupirocin, about 2.5% w/w doxycycline or a pharmaceutically acceptable salt thereof, and about 2.5% w/w ketoconazole.

Disclosed herein is a compounded composition comprising a therapeutically effective amount of mupirocin, a therapeutically effective amount of tobramycin or a pharmaceutically acceptable salt thereof, and ketoconazole or fluconazole. A disclosed compounded composition comprising mupirocin, tobramycin or a salt thereof, and ketoconazole or fluconazole can comprise a dry powder formulation or can comprise a cream or ointment.

In an aspect, a disclosed compounded composition comprising mupirocin, tobramycin or a salt thereof, and ketoconazole can comprise from about 1.4% w/w to about 2.0% w/w, from about 1.5% w/w to about 1.9% w/w, or from about 1.6% w/w to about 1.8% w/w mupirocin. In an aspect, a disclosed compounded composition comprising mupirocin, tobramycin or a salt thereof, and ketoconazole can comprise about 1.695% w/w or about 1.8475% w/w mupirocin. In an aspect, a disclosed compounded composition comprising mupirocin, tobramycin or a salt thereof, and ketoconazole can comprise from about 1.0% w/w to about 7.0% w/w or from about 2.0% to about 6.0% w/w tobramycin or a pharmaceutically acceptable salt thereof. In an aspect, a disclosed compounded composition comprising mupirocin, tobramycin or a salt thereof, and ketoconazole can comprise about 2.5% w/w or about 5.0% w/w tobramycin or a pharmaceutically acceptable salt thereof. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w ketoconazole. In an aspect, a disclosed compounded composition comprising mupirocin, tobramycin or a salt thereof, and ketoconazole can comprise about 2.5% w/w or 5.0% w/w ketoconazole.

In an aspect, a disclosed compounded composition comprising mupirocin, tobramycin or a salt thereof, and ketoconazole can comprise about 1.695% w/w mupirocin, about 5.0% tobramycin or a pharmaceutically acceptable salt thereof, and about 5.0% ketoconazole.

In an aspect, a disclosed compounded composition comprising mupirocin, tobramycin or a salt thereof, and ketoconazole can comprise about 1.8475% w/w mupirocin, about 2.5% tobramycin or a pharmaceutically acceptable salt thereof, and about 2.5% ketoconazole.

In an aspect, a disclosed compounded composition comprising mupirocin, tobramycin or a salt thereof, and fluconazole can comprise about 1.7% w/w mupirocin, about 5% w/w tobramycin or a pharmaceutically acceptable salt thereof, and about 2.5% w/w fluconazole.

Disclosed herein is a compounded composition comprising a therapeutically effective amount of mupirocin, a therapeutically effective amount of fluoroquinolone, and a therapeutically effective amount of an azole. A disclosed compounded composition comprising mupirocin, a fluoroquinolone, and an azole can comprise a dry powder formulation or can comprise a cream or ointment. In an aspect, a fluoroquinolone can comprise enoxacin, ciprofloxacin, norfloxacin, ofloxacin, levofloxacin, trovafloxacin, gatifloxacin, or moxifloxacin. In an aspect, a fluoroquinolone can comprise ciprofloxacin. In an aspect, an azole can comprise clotrimazole, econazole, oxiconazole, ketoconazole, miconazole, sulconazole, fluconazole, itraconazole, or voriconazole. In an aspect, an azole can comprise ketoconazole.

In an aspect, a disclosed compounded composition comprising mupirocin, a fluoroquinolone, and an azole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, a fluoroquinolone, and an azole can comprise about 1.8453% w/w mupirocin. In an aspect, a disclosed compounded composition comprising mupirocin, a fluoroquinolone, and an azole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w of a fluoroquinolone. In an aspect, a disclosed compounded composition comprising mupirocin, a fluoroquinolone, and an azole can comprise about 2.5% w/w of a fluoroquinolone. In an aspect, a disclosed compounded composition comprising mupirocin, a fluoroquinolone, and an azole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w of an azole. In an aspect, a disclosed compounded composition comprising mupirocin, a fluoroquinolone, and an azole can comprise about 2.5% w/w of an azole. In an aspect, an azole can comprise ketoconazole.

In an aspect, a disclosed compounded composition comprising mupirocin, a fluoroquinolone, and an azole can comprise about the same amount of both an azole and a fluoroquinolone. In an aspect, a disclosed compounded composition comprising mupirocin, a fluoroquinolone, and an azole can comprise about 1.8453% w/w mupirocin, about 2.5% w/w of a fluoroquinolone, and about 2.5% w/w of an azole.

Disclosed herein is a compounded composition comprising a therapeutically effective amount of mupirocin, a therapeutically effective amount of ciprofloxacin or a pharmaceutically acceptable salt thereof, and a therapeutically effective amount of ketoconazole. A disclosed compounded composition comprising mupirocin, ciprofloxacin or a salt thereof, and ketoconazole can comprise a dry powder formulation or can comprise a cream or ointment.

In an aspect, a disclosed compounded composition comprising mupirocin, ciprofloxacin or a salt thereof, and ketoconazole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, ciprofloxacin or a salt thereof, and ketoconazole can comprise about 1.768% w/w or 1.8453% w/w mupirocin. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ciprofloxacin or a pharmaceutically acceptable salt thereof. In an aspect, a disclosed compounded composition comprising mupirocin, ciprofloxacin or a salt thereof, and ketoconazole can comprise about 2.5% w/w or about 5.0% w/w ciprofloxacin or a pharmaceutically acceptable salt thereof. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ketoconazole. In an aspect, a disclosed compounded composition comprising mupirocin, ciprofloxacin or a salt thereof, and ketoconazole can comprise about 2.5% w/w or about 5.0% w/w ketoconazole. In an aspect, a disclosed compounded composition can comprise about 1.8453% w/w mupirocin, about 2.5% w/w ciprofloxacin or a pharmaceutically acceptable salt thereof, and about 2.5% w/w ketoconazole. In an aspect, a disclosed compounded composition can comprise from about 1.768% w/w to about 1.8% w/w mupirocin, about 5% w/w ciprofloxacin or a pharmaceutically acceptable salt thereof, and about 2.5% w/w ketoconazole.

Disclosed herein is a compounded composition comprising a therapeutically effective amount of mupirocin, a therapeutically effective amount of an additional or second antibacterial agent, and a therapeutically effective amount of an antifungal agent selected from one or more antifungals described herein, such as one or more of ketoconazole, voriconazole, or amphotericin B. The second antibacterial agent may comprise one or more of doxycycline, bacitracin, colistimethate, piperacillin-tazobactam, polymyxin B, or streptomycin. In one embodiment, the second antibacterial agent comprises doxycycline and one or more of bacitracin, colistimethate, piperacillin-tazobactam, polymyxin B, or streptomycin. Other antibacterials may be used in addition to or instead of doxycycline, bacitracin, colistimethate, piperacillin-tazobactam, polymyxin B, or streptomycin, such as the antibacterials described herein.

In one embodiment, a disclosed compounded composition comprising mupirocin and doxycycline or a salt thereof comprises an antifungal agent comprising ketoconazole. In an aspect, a disclosed compounded composition can comprise about 1.6% w/w mupirocin, about 5.0% w/w doxycycline or a pharmaceutically acceptable salt thereof, and about 5.0% w/w ketoconazole. In an aspect, a disclosed compounded composition can comprise about 1.8% w/w mupirocin, about 2.5% w/w doxycycline or a pharmaceutically acceptable salt thereof, and about 2.5% w/w ketoconazole.

In an aspect, a disclosed compounded composition can comprise mupirocin, an antifungal agent, and a second antibacterial agent. In one example, the antifungal agent includes ketoconazole and the second antibacterial agent includes one or more antibacterials (which may include pharmaceutically acceptable salts) selected from bacitracin, colistimethate, piperacillin-tazobactam, polymyxin B, streptomycin, or doxycycline. In one such example, the antifungal agent includes ketoconazole and the second antibacterial agent includes doxycycline and one or more antibacterials selected from bacitracin, colistimethate, piperacillin-tazobactam, polymyxin B, or streptomycin. In an aspect, the mupirocin can comprise a cream or ointment (for example, a mupirocin 2% cream or ointment), the doxycycline or a pharmaceutically acceptable salt thereof can comprise a dry powder, and the ketoconazole can comprise a dry powder. In an aspect, a disclosed compounded composition can comprise from about 1.6% to about 1.8% w/w mupirocin, from about 1.0% to about 5.0% w/w doxycycline or a pharmaceutically acceptable salt thereof, and from about 1.0% to about 5.0% w/w ketoconazole. In an aspect, a disclosed compounded composition can comprise from about 1.6 to about 1.7% w/w mupirocin, from about 1.0% to about 5.0% w/w doxycycline, from about 2% to about 6% w/w streptomycin, and from about 1.0% to about 5.0% w/w ketoconazole. In another embodiment, streptomycin may be replaced by about antibacterial. For example, streptomycin may be replaced by an antibacterial selected from bacitracin, colistimethate, piperacillin-tazobactam, or polymyxin B in an amount from about 2% to about 6% w/w. In another embodiment, streptomycin may be replaced by an antifungal. For example, streptomycin may be replaced by an antifungal selected from voriconazole or amphotericin B in an amount from about 1% to about 5% w/w. In one example, a disclosed compounded composition can comprise about 1.7% w/w mupirocin, about 2% w/w doxycycline, about 4% w/w streptomycin, and about 2.5% w/w ketoconazole.

In one aspect, a disclosed compounded composition comprises a compounded cream or ointment comprising doxycycline, tobramycin, mupirocin, and ketoconazole. The doxycycline may comprise crushed doxycycline hyclate tablets, e.g., 100 mg tablets. The tobramycin may comprise tobramycin sulfate for injection powder. The mupirocin may comprise mupirocin 2% cream or ointment. The ketoconazole may comprise crushed ketoconazole tablets, e.g., 200 mg tablets.

In various aspects, the compounded composition may comprise between about 0.5% and about 5.0%, about 0.5% and about 4.0%, about 0.5% and about 3.0%, about 0.5% and about 2.5%, about 0.5% and about 2.0%, about 0.5% and about 1.5%, about 1.0% and about 5.0%, about 1.0% and about 4.0%, about 1.0% and about 3.0%, about 1.0% and about 2.5%, about 1.0% and about 2.0%, about 1.5% and about 5.0%, about 1.5% and about 4.0%, about 1.5% and about 3.0%, about 1.5% and about 2.5%, about 1.5% and about 2.0%, about 2.0% and about 5.0%, about 2.0% and about 4.0%, about 2.0% and about 3.0%, about 2.0% and about 2.5%, about 2.5% and about 5.0%, about 2.5% and about 4.0%, about 2.5% and about 3.0%, about 3.0% and about 5.0%, about 3.0% and about 4.0%, or about 4.0% and 5.0% (w/w) doxycycline; between about 0.5% and about 5.0%, about 0.5% and about 4.0%, about 0.5% and about 3.0%, about 0.5% and about 2.5%, about 0.5% and about 2.0%, about 0.5% and about 1.5%, about 1.0% and about 5.0%, about 1.0% and about 4.0%, about 1.0% and about 3.0%, about 1.0% and about 2.5%, about 1.0% and about 2.0%, about 1.5% and about 5.0%, about 1.5% and about 4.0%, about 1.5% and about 3.0%, about 1.5% and about 2.5%, about 1.5% and about 2.0%, about 2.0% and about 5.0%, about 2.0% and about 4.0%, about 2.0% and about 3.0%, about 2.0% and about 2.5%, about 2.5% and about 5.0%, about 2.5% and about 4.0%, about 2.5% and about 3.0%, about 3.0% and about 5.0%, about 3.0% and about 4.0%, or about 4.0% and 5.0% (w/w) tobramycin; between about 0.5% and about 5.0%, about 0.5% and about 4.0%, about 0.5% and about 3.0%, about 0.5% and about 2.5%, about 0.5% and about 2.0%, about 0.5% and about 1.5%, about 1.0% and about 5.0%, about 1.0% and about 4.0%, about 1.0% and about 3.0%, about 1.0% and about 2.5%, about 1.0% and about 2.0%, about 1.5% and about 5.0%, about 1.5% and about 4.0%, about 1.5% and about 3.0%, about 1.5% and about 2.5%, about 1.5% and about 2.0%, about 2.0% and about 5.0%, about 2.0% and about 4.0%, about 2.0% and about 3.0%, about 2.0% and about 2.5%, about 2.5% and about 5.0%, about 2.5% and about 4.0%, about 2.5% and about 3.0%, about 3.0% and about 5.0%, about 3.0% and about 4.0%, or about 4.0% and 5.0% (w/w) ketoconazole; and between about 0.5% and about 1.8%, about 0.5% and about 1.5%, about 0.5% and about 1.0%, about 1.0% and about 1.8%, about 1.0% and about 1.8%, about 1.0% and about 1.5%, or about 1.5% and about 1.8% (w/w) mupirocin. In a further aspect, the tobramycin is replaced by the same weight percent of ciprofloxacin. The bulk or remainder of the compounded cream or ointment may be provided by the mupirocin cream or ointment, respectively. In some aspects, additional base or carrier cream or ointment may be added.

In various embodiments, the compounded cream or ointment comprises about 1% to about 1.9% w/w mupirocin and from about 0.2% to about 6% w/w voriconazole. In one example, the compounded cream or ointment comprises about 1.71% w/w mupirocin and 0.8% w/w voriconazole. The mupirocin may be mupirocin 2% cream or mupirocin 2% ointment in an amount approximately 85.7% w/w of the compounded cream or ointment, respectively, and the voriconazole may include voriconazole for injection in an amount about 0.8% w/w of the compounded cream or ointment.

In various embodiments, the compounded cream or ointment comprises about 1% to about 1.9% w/w mupirocin, from about 0.2% to about 6% w/w voriconazole, and from about 0.2% to about 6% w/w streptomycin. In one example, the compounded cream or ointment comprises about 1.6% w/w mupirocin, about 0.8% w/w voriconazole, and about 4% w/w streptomycin. The mupirocin may be mupirocin 2% cream or mupirocin 2% ointment in an amount approximately 80% w/w of the compounded cream or ointment, respectively, the voriconazole may include voriconazole for injection in an amount about 0.8% w/w of the compounded cream or ointment, and the streptomycin may comprise streptomycin sulfate for injection in an amount about 5.528% w/w of the compounded cream or ointment.

In various embodiments, the compounded cream or ointment comprises about 1% to about 1.9% w/w mupirocin, from about 0.2% to about 6% w/w voriconazole, from about 0.2% to about 6% w/w streptomycin, and from about 0.2% to about 6% doxycycline. In one example, the compounded cream or ointment comprises about 1.55% w/w mupirocin, about 0.8% w/w voriconazole, about 4% w/w streptomycin, and about 1% w/w doxycycline. The mupirocin may be mupirocin 2% cream or ointment in an amount approximately 77.6% w/w of the compounded cream or ointment, the voriconazole may include voriconazole for injection in an amount about 0.8% w/w of the compounded cream or ointment, the streptomycin may comprise streptomycin sulfate for injection in an amount about 5.528% w/w of the compounded cream or ointment, and the doxycycline may comprise doxycycline hyclate 100 mg tablets in an amount about 2.435% w/w of the compounded cream or ointment. Other strength tablets may be used.

In various embodiments, the compounded cream or ointment comprises about 1% to about 1.9% w/w mupirocin, from about 0.2% to about 6% w/w voriconazole, from about 0.2% to about 6% w/w tobramycin, and from about 0.2% to about 6% doxycycline. In one example, the compounded cream or ointment comprises about 1.62% w/w mupirocin, about 0.8% w/w voriconazole, about 1.2% w/w tobramycin, and about 1% w/w doxycycline. The mupirocin may be mupirocin 2% cream or ointment in an amount approximately 81.3% w/w of the compounded cream or ointment, the voriconazole may include voriconazole for injection in an amount about 0.8% w/w of the compounded cream or ointment, the tobramycin may comprise tobramycin sulfate for injection in an amount about 1.8% w/w of the compounded cream or ointment, and the doxycycline may comprise doxycycline hyclate 100 mg tablets in an amount about 2.435% w/w of the compounded cream or ointment. Other strength tablets may be used.

In various embodiments, the compounded cream or ointment comprises about 1% to about 1.9% w/w mupirocin, from about 0.2% to about 6% w/w ketoconazole, from about 0.2% to about 6% w/w streptomycin, and from about 0.2% to about 6% doxycycline. In one example, the compounded cream or ointment comprises about 1.71% w/w mupirocin, about 2% w/w ketoconazole, about 4% w/w streptomycin, and about 2% w/w doxycycline. The mupirocin may be mupirocin 2% cream or ointment in an amount approximately 85.7% w/w of the compounded cream or ointment, the ketoconazole may include ketoconazole 200 mg tablets in an amount about 3.875% w/w of the compounded cream or ointment, the streptomycin may comprise streptomycin sulfate for injection in an amount about 5.528% w/w of the compounded cream or ointment, and the doxycycline may comprise doxycycline hyclate 100 mg tablets in an amount about 4.87% w/w of the compounded cream or ointment. Other strength tablets may be used as described further below, a method of compounding the compounded composition may comprise grinding a suitable amount of doxycycline hyclate tablets and ketoconazole tablets and combining the powder from the crushed tablets with a suitable amount of tobramycin sulfate for injection powder and a suitable volume of mupirocin 2% cream or ointment. For example, compounding a compounded composition comprising about 2.5% (w/w) doxycycline, about 2.5% (w/w) tobramycin, about 1.726% (w/w) mupirocin, and about 2.5% (w/w) ketoconazole may include crushing doxycycline hyclate tablets and ketoconazole tablets and combining the powder from the crushed tablets with a suitable amount of tobramycin sulfate for injection powder and a suitable volume of mupirocin 2% cream or ointment. Each gram of the compounded composition contains about 2.5% doxycycline (or 25 mg doxycycline), which is equivalent to 0.25 tablets of 100 mg doxycycline tablets, which is equivalent to 60.875 mg (25% of 243.5 mg total weight of a 100 mg doxycycline tablet). Each gram of compounded composition contains about 2.5% ketoconazole (or 25 mg ketoconazole) which is equivalent to about 0.125 tablets of 200 mg ketoconazole tablets, which is equivalent to about 38.75 mg (25% of 310 mg total weight of a 100 mg ketoconazole tablet). Each gram of compounded composition contains about 2.5% tobramycin, equivalent to about 25 mg tobramycin USP, equivalent to about 37.5 mg of tobramycin sulfate, which may reflect usage of about 2% of 1 vial of tobramycin 1.2 g vials per gram of compounded composition. The powders may be added to a suitable amount of mupirocin cream or mupirocin ointment to formulate the desired concentration of the compounded composition cream or ointment. For example, for every gram of compounded composition cream or ointment, the powders may be combined with about 0.863 g of mupirocin 2% cream or ointment. The combined mixture may be suitably processed in an ointment mill as described elsewhere herein. The compounded composition may be packaged in suitable packaging, e.g., tubes or syringes. As noted elsewhere herein, the term "about" means a value falling within a range that is ±10% of the stated value. Thus, in an aspect, the skilled person can combine 0.863 g±10% mupirocin 2.0% cream or ointment (e.g., from about 0.7767 g-0.9493 g), 0.060875 g±10% powder from crushed doxycycline hyclate 100 mg tablets (e.g., from about 0.0547875 g-0.0669625 g), 0.0375 g±10% tobramycin sulfate USP powder for injection (e.g., from about 0.03375 g-0.04125 g), and 0.03875 g±10% powder from crushed ketoconazole 200 mg tablets (e.g., from about 0.034875 g-0.042625 g) and mix together according to a method described above to make about 1.0 g±10% of the compounded composition. Other strength tablets and cream or ointments may be used wherein amounts combined are suitably adjusted.

In these or other embodiments, the compounded composition may comprise between 5.5% and 6.5% w/w crushed doxycycline hyclate 100 mg tablets. The compounded composition may further comprise between 3.3% and 4.3% w/w crushed ketoconazole 200 mg tablets. The compounded composition may further comprise between 3.2% and 4.2% w/w tobramycin sulfate USP powder for injection. In any of the above combinations, the compounded composition may comprise at least 60%, 75%, 80%, 85%, or 89% mupirocin cream or mupirocin ointment. In one example, mupirocin cream or mupirocin ointment makes up the remaining weight of the composition. For example, the compounded composition may comprise between 84.9% and 88.9% mupirocin cream or mupirocin ointment.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin. In one example, the compounded composition comprises about 1.6% w/w mupirocin, about 0.8% w/w voriconazole, and about 4% w/w streptomycin. The mupirocin may be mupirocin 2% cream or ointment in an amount approximately 80% w/w of the compounded composition, the voriconazole may include voriconazole for injection in an amount about 0.8% w/w of the compounded composition, and the streptomycin may comprise streptomycin sulfate for injection in an amount about 5.528% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin and about 0.2% to about 6% doxycycline. In one example, the compounded composition comprises about 1.55% w/w mupirocin, about 0.8% w/w voriconazole, about 4% w/w streptomycin, and about 1% w/w doxycycline. The mupirocin may be mupirocin 2% cream or ointment in an amount approximately 77.6% w/w of the compounded composition, the voriconazole may include voriconazole for injection in an amount about 0.8% w/w of the compounded composition, the streptomycin may comprise streptomycin sulfate for injection in an amount about 5.528% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w tobramycin and about 0.2% to about 6% doxycycline. In one example, the compounded composition comprises about 1.62% w/w mupirocin, about 0.8% w/w voriconazole, about 1.2% w/w tobramycin, and about 1% w/w doxycycline. The mupirocin may be mupirocin 2% cream or ointment in an amount approximately 81.3% w/w of the compounded composition, the voriconazole may include voriconazole for injection in an amount about 0.8% w/w of the compounded composition, the tobramycin may comprise tobramycin sulfate for injection in an amount about 1.8% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w ketoconazole, and the second antibacterial comprises from about 0.2% to about 6% w/w streptomycin and about 0.2% to about 6% doxycycline. In one example, the compounded composition comprises about 1.71% w/w mupirocin, about 2% w/w ketoconazole, about 4% w/w streptomycin, and about 2% w/w doxycycline. The mupirocin may be mupirocin 2% cream or ointment in an amount approximately 85.7% w/w of the compounded composition, the ketoconazole may include ketoconazole 200 mg tablets in an amount about 3.875% w/w of the compounded composition, the streptomycin may comprise streptomycin sulfate for injection in an amount about 5.528% w/w of the compounded composition, and the doxycycline may comprise doxycycline hyclate 100 mg tablets in an amount about 4.87% w/w of the compounded composition.

As another example, a method of compounding the compounded composition may comprise grinding a suitable amount of doxycycline hyclate tablets, ketoconazole tablets, and ciprofloxacin tablets and combining the powder from the crushed tablets with a suitable volume of mupirocin 2% cream or ointment. For example, compounding a compounded composition comprising about 2.5% (w/w) doxycycline, about 2.5% (w/w) ciprofloxacin, about 1.724% (w/w) mupirocin, and about 2.5% (w/w) ketoconazole may include crushing tablets of doxycycline hyclate, ketoconazole, and ciprofloxacin and combining the powder from the crushed tablets with a volume of mupirocin 2% cream or ointment. Each gram of the compounded composition contains about 2.5% doxycycline (or 25 mg doxycycline), which is equivalent to 0.25 tablets of 100 mg doxycycline tablets, which is equivalent to 60.875 mg (25% of 243.5 mg total weight of a 100 mg doxycycline tablet). Each gram of compounded composition contains about 2.5% ketoconazole (or 25 mg ketoconazole) which is equivalent to about 0.125 tablets of 200 mg ketoconazole tablets, which is equivalent to about 38.75 mg (25% of 310 mg total weight of a 100 mg ketoconazole tablet). Each gram of compounded composition contains about 2.5% ciprofloxacin (or 25 mg ketoconazole) which is equivalent to about 0.033 tablets of 750 mg ciprofloxacin tablets, which is equivalent to about 39.9 mg (25% of 1.137 g total weight of a 750 mg ciprofloxacin tablet). The powders may be added to a suitable amount of mupirocin cream or mupirocin ointment to formulate the desired concentration of the compounded composition cream or ointment. For example, for every gram of compounded composition cream or ointment, the powders may be combined with about 0.863 g of mupirocin 2% cream, ointment, or combination thereof. The combined mixture may be suitably processed in an ointment mill as described elsewhere herein. The compounded composition may be packaged in suitable packaging, e.g., tubes or syringes. As noted elsewhere herein, the term "about" means a value falling within a range that is ±10% of the stated value. Thus, in an aspect, the skilled person can combine 0.862 g±10% mupirocin 2.0% cream or ointment (e.g., from about 0.7758 g-0.9482 g), 0.060875 g±10% powder from crushed doxycycline hyclate 100 mg tablets (e.g., from about 0.0547875 g-0.0669625 g), 0.0379 g±10% powder from ciprofloxacin 750 mg tablets (e.g., from about 0.03411 g-0.04169 g), and 0.03875 g±10% powder from crushed ketoconazole 200 mg tablets (e.g., from about 0.034875 g-0.042625 g) and mix together according to a method described above to make about 1.0 g±10% of the compounded composition. Other strength tablets and ointments may be used wherein amounts combined are suitably adjusted. In these or other embodiments, the compounded composition comprises between 5.5% and 6.5% w/w crushed doxycycline hyclate 100 mg tablets. The compounded composition may further comprise between 3.3% and 4.3% w/w crushed ketoconazole 200 mg tablets. The compounded composition may further comprise between 3.3% and 4.3% w/w crushed ciprofloxacin 750 mg tablets. In any of the above combinations, the compounded composition may comprise at least 60%, 75%, 80%, 85%, or 89% mupirocin cream or mupirocin ointment. In one example, mupirocin cream or mupirocin ointment makes up the remaining weight of the composition. For example, the compounded composition may comprise between 84.9% and 88.9% mupirocin cream or mupirocin ointment.

In an aspect, a disclosed compounded composition can comprise a therapeutically effective amount of one or more additional antimicrobial agents. In an aspect, the additional antimicrobial agent can be an antibacterial agent. In an aspect, the additional antimicrobial agent can be an antifungal agent.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

6. Miscellaneous

The compounded composition may include multiple antimicrobials in combination with mupirocin, such as mupirocin 2% cream or ointment. The multiple antimicrobials may be selected from any combination of the antibacterial and antifungals described herein. In one example, one or more of the antimicrobials may comprise one or more antibacterials or pharmaceutically acceptable salt thereof selected from bacitracin, colistimethate, piperacillin-tazobactam, polymyxin B, streptomycin, or combination thereof and/or one or more one or more antifungals or pharmaceutically acceptable salt thereof selected from voriconazole, amphotericin B, or combination thereof. In these or other embodiments, one or more of the antimicrobials may comprise the antibacterial doxycycline or pharmaceutically acceptable salt and/or the antifungal ketoconazole or pharmaceutically acceptable salt thereof. In some embodiments, mupirocin may be provided in a cream or ointment. In various embodiments, the compounded composition may include from about 20% to about 95%, about 60% to about 90%, about 70% to about 88%, about 75% to about 88% mupirocin 2% cream or ointment w/w. As introduced above, the compounded composition may include additional antimicrobials such as a second antibacterial agent and an antifungal agent may comprise powders compounded with the mupirocin cream or mupirocin ointment. In an aspect, the compounded composition may include an amount of second antibacterial agent from about 1% to about 30%, about 1% to about 20%, about 1% to about 10%, about 1% to about 5%, about 4% to about 15%, about 4% to about 10%, or about 4% to about 8% w/w. In an aspect, the compounded composition may include an amount of antifungal agent from about 1% to about 30%, about 1% to about 20%, about 1% to about 10%, about 1% to about 5%, about 2% to about 15%, about 2% to about 10%, or about 2% to about 8% w/w. In various embodiments, the powders may comprise antimicrobial tablets (ground, e.g., crushed), bulk powder, or antimicrobial for injection. Antimicrobials for injection may comprise powder, typically available in vials, for reconstitution. In some embodiments, the compounded composition may include from about 1% to about 30%, about 1% to about 20%, about 4% to about 20%, about 4% to about 15% w/w antimicrobial for injection. In various embodiments, the compounded composition comprises antimicrobial for injection in an amount between about 3% and about 20% w/w. In an aspect, the antimicrobial for injection comprises one or more of bacitracin for injection, colistimethate sodium for injection, pentasodium colistin methanesulfonate for injection, piperacillin-tazobactam for injection, polymyxin B for injection USP, streptomycin sulfate for injection, tobramycin sulfate for injection, voriconazole for injection, or amphotericin B for injection. In these or other embodiments, the compounded composition may include from about 1% to about 30%, about 1% to about 20%, about 1% to about 10%, about 3% to about 15%, or about 4% to about 12% crushed antimicrobial tablets.

Disclosed herein is a compounded composition comprising a therapeutically effective amount of mupirocin, a therapeutically effective of amount of clindamycin or a pharmaceutically acceptable salt thereof, a therapeutically effective of amount of gentamicin or a pharmaceutically acceptable salt thereof, and a therapeutically effective of amount of econazole or a pharmaceutically acceptable salt thereof. A disclosed compounded composition comprising mupirocin, clindamycin or a salt thereof, gentamicin or a salt thereof, and econazole or a salt thereof can comprise a dry powder formulation or can comprise a cream or ointment.

In an aspect, a disclosed compounded composition comprising mupirocin, clindamycin or a salt thereof, gentamicin or a salt thereof, and econazole or a salt thereof can comprise from about 0.5% w/w to about 1.4% w/w, from about 0.6% w/w to about 1.3% w/w, from about 0.7% w/w to about 1.2% w/w, from about 0.7% w/w to about 1.1% w/w, from about 0.8% w/w to about 1.0% w/w, or from about 0.9% w/w to about 1.0% w/w mupirocin.

In an aspect, a disclosed compounded composition comprising mupirocin, clindamycin or a salt thereof, gentamicin or a salt thereof, and econazole or a salt thereof can comprise from about 0.01% w/w to about 0.08% w/w or from about 0.04% w/w and about 0.06% w/w clindamycin or a pharmaceutically acceptable salt thereof. In an aspect, a disclosed compounded composition comprising mupirocin, clindamycin or a salt thereof, gentamicin or a salt thereof, and econazole or a salt thereof can comprise about 0.01% w/w, about 0.02% w/w, about 0.03% w/w, about 0.06% w/w, or about 0.07% w/w clindamycin or a pharmaceutically acceptable salt thereof.

In an aspect, a disclosed compounded composition comprising mupirocin, clindamycin or a salt thereof, gentamicin or a salt thereof, and econazole or a salt thereof can comprise from about 0.01% w/w to about 0.05% w/w, from about 0.01% w/w to about 0.04% w/w, from about 0.01% w/w to about 0.03% w/w, or from about 0.015% w/w to about 0.025% w/w gentamicin or a pharmaceutically acceptable salt thereof.

In an aspect, a disclosed compounded composition comprising mupirocin, clindamycin or a salt thereof, gentamicin or a salt thereof, and econazole or a salt thereof can comprise from about 0.1% w/w to about 0.6% w/w, from about 0.2% w/w to about 0.5% w/w, from about 0.2% w/w to about 0.4% w/w, or from about 0.025% w/w to about 0.035% w/w econazole or a pharmaceutically acceptable salt thereof.

In an aspect, a disclosed compounded composition comprising mupirocin, clindamycin or a salt thereof, gentamicin or a salt thereof, and econazole or a salt thereof can comprise from about 0.9% w/w to 1.0% w/w mupirocin, from about 0.04% w/w to about 0.06% w/w clindamycin or a pharmaceutically acceptable salt thereof, from about 0.01% w/w to about 0.03% w/w gentamicin or a pharmaceutically acceptable salt thereof, and from about 0.2% w/w to about 0.4% w/w econazole or a pharmaceutically acceptable salt thereof. In an aspect, a disclosed compounded composition can comprise about 0.9% w/w mupirocin, about 0.05% w/w clindamycin phosphate, about 0.02% w/w gentamicin sulfate, and about 0.3% w/w econazole nitrate.

Disclosed herein is a compounded composition comprising a therapeutically effective amount of doxycycline or a pharmaceutically acceptable salt thereof and a therapeutically effective amount of nystatin. A disclosed compounded composition comprising doxycycline or a salt thereof and nystatin can comprise a dry powder formulation or can comprise a cream or ointment.

In an aspect, a disclosed compounded composition comprising doxycycline or a salt thereof and nystatin can comprise from about 1.0% w/w to about 10.0% w/w or from about 2.0% w/w to about 9.0% w/w doxycycline or a pharmaceutically acceptable salt thereof. In an aspect, a disclosed compounded composition comprising doxycycline or a salt thereof and nystatin can comprise about 3.0% w/w, about 4.0% w/w, about 5.0% w/w, about 6.0%, about 7.0% w/w, or about 8.0% w/w doxycycline or a pharmaceutically acceptable salt thereof. In an aspect, a disclosed compounded composition comprising doxycycline or a salt thereof and nystatin can comprise from about 50,000 to about 98,000 units per gram, from about 60,000 to about 90,000 units per gram, from about 70,000 to about 90,000 units per gram, or from about 80,000 to about 90,000 units per gram nystatin. In an aspect, a disclosed compounded composition comprising doxycycline or a salt thereof and nystatin can comprise from about 4.0% w/w to about 6.0% w/w doxycycline or a pharmaceutically acceptable salt thereof and from about 80,000 to about 90,000 units per gram nystatin. In an aspect, a disclosed compounded composition comprising doxycycline or a salt thereof and nystatin can comprise about 5.0% w/w doxycycline or a pharmaceutically acceptable salt thereof and about 87,825 units per gram nystatin.

Disclosed herein is a compounded composition comprising a therapeutically effective amount of tobramycin or a pharmaceutically acceptable salt thereof and a therapeutically effective amount of nystatin. A disclosed compounded composition comprising tobramycin or a salt thereof and nystatin can comprise a dry powder formulation or can comprise a cream or ointment.

In an aspect, a disclosed compounded composition comprising tobramycin or a salt thereof and nystatin can comprise from about 1.0% w/w to about 10.0% w/w or from about 2.0% w/w to about 9.0% w/w tobramycin or a pharmaceutically acceptable salt thereof. In an aspect, a disclosed compounded composition comprising tobramycin or a salt thereof and nystatin can comprise about 3.0% w/w, about 4.0% w/w, about 5.0% w/w, about 6.0%, about 7.0% w/w, or about 8.0% w/w tobramycin or a pharmaceutically acceptable salt thereof. In an aspect, a disclosed compounded composition comprising tobramycin or a salt thereof and nystatin can comprise from about 50,000 to about 98,000 units per gram, from about 60,000 to about 90,000 units per gram, from about 70,000 to about 90,000 units per gram, or from about 80,000 to about 90,000 units per gram nystatin. In an aspect, a disclosed compounded composition comprising tobramycin or a salt thereof and nystatin can comprise from about 4.0% w/w to about 6.0% w/w tobramycin or a pharmaceutically acceptable salt thereof and from about 80,000 to about 90,000 units per gram nystatin. In an aspect, a disclosed compounded composition comprising tobramycin or a salt thereof and nystatin can comprise about 5.0% tobramycin or a pharmaceutically acceptable salt thereof and about 87,825 units per gram nystatin.

Disclosed herein is a compounded composition comprising a therapeutically effective amount of clobetasol propionate and a therapeutically effective amount of fluconazole or urea. In an aspect, a disclosed compounded composition comprising clobetasol propionate and fluconazole or urea can comprise a dry powder formulation or can comprise a cream or ointment.

In an aspect, a disclosed compounded composition comprising clobetasol propionate and fluconazole can comprise from about 0.02% w/w to about 0.10% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and fluconazole can comprise from about 1.0% w/w to about 5.0% w/w, from about 2.0% w/w to about 4.0% w/w, from about 2.0% w/w to about 3.0% w/w, or from about 2.0% w/w to about 4.0% w/w fluconazole. In an aspect, a disclosed compounded composition comprising clobetasol propionate and fluconazole can comprise from about 0.02% w/w to about 0.06% w/w clobetasol propionate and from about 2.0% w/w to about 4.0% w/w fluconazole. In an aspect, a disclosed compounded composition can comprise about 0.0485% w/w clobetasol propionate and about 3.0% w/w fluconazole. In an aspect, clobetasol propionate can comprise clobetasol propionate 0.05% ointment.

In an aspect, a disclosed compounded composition comprising clobetasol propionate and urea can comprise from about 0.02% w/w to about 0.10% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and urea can comprise from about 10.0% w/w to about 60.0% w/w, from about 20.0% w/w to about 50.0% w/w, from about 30.0% w/w to about 50.0% w/w, from about 30.0% w/w to about 40.0% w/w, or from about 40.0% w/w to about 50.0% w/w urea. In an aspect, a disclosed compounded composition comprising clobetasol propionate and urea can comprise from about 0.02% w/w to about 0.055% w/w clobetasol propionate and from about 30.0% w/w to about 50.0% w/w urea. In an aspect, a disclosed compounded composition comprising clobetasol propionate and urea can comprise about 0.03% w/w clobetasol propionate and about 40.0% w/w urea. In an aspect, clobetasol propionate can comprise clobetasol propionate 0.05% ointment.

Disclosed herein is a compounded composition comprising a therapeutically effective amount of clobetasol propionate and a therapeutically effective of amount of ketoconazole. A disclosed compounded composition can comprise a dry powder formulation or can comprise a cream or ointment.

In an aspect, a disclosed compounded composition comprising clobetasol propionate and ketoconazole can comprise from about 0.02% w/w to about 0.1% w/w, from about 0.02% w/w to about 0.08% w/w, from about 0.02% w/w to about 0.06% w/w, from about 0.02% w/w to about 0.05% w/w, from about 0.03% w/w to about 0.05% w/w, from about 0.03% w/w to about 0.04% w/w, or from about 0.04% w/w to about 0.05% w/w clobetasol propionate. In an aspect, a disclosed compounded composition comprising clobetasol propionate and ketoconazole can comprise from about 3.0% w/w to about 12.0% w/w, from about 4.0% w/w to about 10.0% w/w, from about 5% w/w to about 10% w/w, or from about 6.0% w/w to about 8.0% w/w ketoconazole. In an aspect, a disclosed compounded composition comprising clobetasol propionate and ketoconazole can comprise from about 0.04% w/w to about 0.05% w/w clobetasol propionate and from about 6.0% w/w to about 8.0% w/w ketoconazole. In an aspect, a disclosed compounded composition comprising clobetasol propionate and ketoconazole can comprise about 0.04% w/w clobetasol propionate and about 7.5% w/w ketoconazole. In an aspect, clobetasol propionate can comprise clobetasol propionate 0.05% ointment.

Disclosed herein is a compounded composition comprising a therapeutically effective amount of ketoconazole, a sufficient amount of an excipient base powder comprising a blend of micronized xylitol and poloxamers, and a sufficient amount of xylitol. A disclosed compounded composition can comprise a dry powder formulation or can comprise an ointment.

In an aspect, an excipient base powder comprising a blend a micronized xylitol and poloxamers can be LoxaSperse™ excipient base powder. In an aspect, an excipient base powder comprising a blend a micronized xylitol and poloxamers can be XyliFos™ excipient base powder.

In an aspect, a disclosed compounded composition comprising ketoconazole, an excipient base powder, and xylitol can comprise from about 10.0% w/w to about 50.0% w/w, from about 20.0% w/w to about 40.0% w/w, or from about 25.0% w/w to about 35.0% w/w ketoconazole. In an aspect, a disclosed compounded composition comprising ketoconazole, an excipient base powder, and xylitol can comprise a weight ratio of excipient base powder to xylitol of about 1:1, about 1:2, about 1:3, about 1:4, about 1:5, about 1:6, about 1:7, from about 1:1 to about 1:7, from about 1:2 to about 1:6, or from about 1:4 to about 1:5. In an aspect, the weight ratio of excipient base powder to xylitol can be about 1:4.35. In an aspect, a disclosed compounded composition comprising ketoconazole, an excipient base powder, and xylitol can comprise about 30.0% w/w ketoconazole and a weight ratio of excipient base powder to xylitol of about 1:4 to about 1:5. In an aspect, a disclosed compounded composition comprising ketoconazole, an excipient base powder, and xylitol can comprise about 30.0% w/w ketoconazole and a weight ratio of excipient base powder to xylitol of about 1:4.35. In an aspect, a disclosed compounded composition comprising ketoconazole, LoxaSperse™, and xylitol can comprise about 30.0% w/w ketoconazole and a weight ratio of LoxaSperse™ to xylitol of about 1:4.35.

In an aspect, a disclosed compounded composition can comprise a therapeutically effective amount of one or more additional antimicrobial agents. In an aspect, the additional antimicrobial agent can be an antibacterial agent. In an aspect, the additional antimicrobial agent can be an antifungal agent.

In an aspect, a disclosed compounded composition can comprise one or more excipients or additives. In an aspect, excipients or additives include, but are not limited to, the following: solvents, surfactants, humectants, preservatives, flavorings, stabilizers (including antioxidants), binders, and colorants.

7. Capsules

Disclosed herein is a capsule comprising a disclosed compounded composition. Capsules may include dry powder obtained from crushed tablets, bulk powders, antimicrobials for injection, or combinations thereof.

In an aspect, a disclosed capsule can comprise about 100 mg to about 2000 mg of a disclosed compounded composition. In an aspect, a disclosed capsule can comprise about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg of a disclosed compounded composition.

In an aspect, a disclosed capsule comprising a disclosed compounded composition can be broken apart such that its contents can be retrieved. In an aspect, a disclosed capsule can be dissolved in water such that its contents can be contacted with the water.

In an aspect, a disclosed capsule can comprise one or more additional antimicrobial agents. In an aspect, the additional antimicrobial agent can be a dry powder. In an aspect, the additional antimicrobial agent can be a cream or ointment. The additional antimicrobial agent can be pure or substantially pure. The additional antimicrobial agent can be obtained from a bulk source. In an aspect, the additional antimicrobial agent can be an antibacterial agent. In an aspect, the additional antimicrobial agent can be an antifungal agent.

In an aspect, a disclosed capsule can comprise one or more excipients or additives. In an aspect, excipients or additives include, but are not limited to, the following: solvents, surfactants, humectants, preservatives, flavorings, stabilizers (including antioxidants), binders, and colorants.

B. Methods

1. A First Antibacterial Agent and a Second Antibacterial Agent

Disclosed herein is a method of making a compounded composition, the method comprising: mixing a therapeutically effective amount of a first antibacterial agent and a therapeutically effective amount of a second antibacterial agent to make a homogeneous compounded composition. A disclosed compounded composition can comprise a dry powder formulation or can comprise a cream or ointment.

The first and/or second antimicrobial agent may comprise one or more enicillins, cephalosporins, fluoroquinolones, aminoglycosides, monobactams, carbapenems, macrolides, other antibacterial, or combination thereof. For example, the first and/or second antibacterial agent may include one or more antibacterial pharmaceutical drugs selected from afenide, amikacin, amoxicillin, ampicillin, arsphenamine, azithromycin, azlocillin, aztreonam, bacampicillin, bacitracin, carbacephem (loracarbef), carbenicillin, cefaclor, cefadroxil, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalexin, chloramphenicol, chlorhexidine, ciprofloxacin, clarithromycin, clavulanic acid, clindamycin, cloxacillin, colimycin, colistimethate teicoplanin, colistin, demeclocycline, dicloxacillin, dirithromycin, doripenem, doxycycline, efprozil, enoxacin, ertapenem, erythromycin, ethambutol, flucloxacillin, fosfomycin, furazolidone, gatifloxacin, geldanamycin, gentamicin, grepafloxacin, herbimycin, imipenem, isoniazid, kanamycin, levofloxacin, lincomycin, linezolid, lomefloxacin, meropenem, methicillin, meticillin, mezlocillin, minocycline, mitomycin, moxifloxacin, mupirocin, nafcillin, neomycin, netilmicin, nitrofurantoin, norfloxacin, ofloxacin, oxacillin, oxytetracycline, paromomycin, penicillin G, penicillin V, piperacillin, pivmecillinam, platensimycin, polymyxin B, prontosil, pvampicillin, pyrazinamide, quinupristin/dalfopristin, rifampicin, rifampin, roxithromycin, sparfloxacin, spectinomycin, spiramycin, sulbactam, sulfacetamide, sulfamethizole, sulfamethoxazole, sulfanilamide, sulfanilimide, sulfisoxazole, sulphonamides, sultamicillin, telithromycin, tetracycline, thiamphenicol, ticarcillin, tobramycin, trimethoprim, trimethoprim-sulfamethoxazole, troleandomycin, trovafloxacin, or a combination thereof. In some embodiments, the first antibacterial agent is selected from mupirocin, gentamycin, tobramycin, or combinations thereof. In one embodiment, the first antibacterial agent includes an aminoglycoside. In one embodiment, the first antimicrobial agent comprises an antibacterial agent selected from one or more antibacterial drugs comprising vancomycin, ciprofloxacin, levofloxacin, azithromycin, clindamycin, doxycycline, mupirocin, ceftriaxone, colistimethate, tobramycin, cefepime, gentamicin, streptomycin, sulfamethoxazole/ trimethoprim.

In an aspect, the mixing can comprise using an electronic mortar and pestle (EMP). In an aspect, a disclosed method can comprise milling the ingredients (using, for example, a three-roll mill). Mixing and milling can be done according to standards known to the skilled person in the art.

In an aspect, a disclosed method can comprise obtaining the first antibacterial agent, obtaining the second antibacterial agent, or a combination thereof. In an aspect, obtaining can comprise obtaining a bulk source of the first antibacterial agent, obtaining a bulk source of the second antibacterial agent, or a combination thereof.

In an aspect, a disclosed compounded composition comprising a first antibacterial agent and a second antibacterial agent can comprise from about 1.0% w/w to about 3.0% w/w of the first antibacterial agent. In an aspect, a disclosed compounded composition comprising a first antibacterial agent and a second antibacterial agent can comprise about 1.6% w/w, or about 1.7% w/w, or about 1.756% w/w, or about 1.77% w/w, or about 1.775% w/w, or about 1.8% w/w of the first antibacterial agent. In an aspect, a disclosed compounded composition comprising a first antibacterial agent and a second antibacterial agent can comprise from about 4.0% w/w to about 9.0% w/w or from about 6.0% w/w to about 8.0% w/w of the second antibacterial agent. In an aspect, a disclosed compounded composition comprising a first antibacterial agent and a second antibacterial agent comprise about 5.0% w/w or about 7.5% w/w of the second antibacterial agent.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

2. An Antibacterial Agent and an Antifungal Agent

Disclosed herein is a method of making a compounded composition, the method comprising: mixing a therapeutically effective amount of an antibacterial agent and a therapeutically effective amount of an antifungal agent to make a homogeneous compounded composition. A disclosed compounded composition can comprise a dry powder formulation or can comprise a cream or ointment.

In an aspect, the mixing can comprise using an electronic mortar and pestle (EMP). In an aspect, a disclosed method can comprise milling the ingredients (using, for example, a three-roll mill). Mixing and milling can be done according to standards known to the skilled person in the art.

In an aspect, a disclosed method can comprise obtaining the antibacterial agent, obtaining the antifungal agent, or a combination thereof. In an aspect, obtaining can comprise obtaining a bulk source of one or more antibacterials of the antibacterial agent or obtaining a bulk source of one or more antifungals of the antifungal agent.

In an aspect, a disclosed compounded composition comprising an antibacterial agent and an antifungal agent can comprise from about 1.0% w/w to about 3.0% w/w of the antibacterial agent. In an aspect, a disclosed compounded composition comprising an antibacterial agent and an antifungal agent can comprise about 1.6% w/w, or about 1.626 w/w, or about 1.7% w/w, or about 1.71% w/w, or about 1.756% w/w, or about 1.77% w/w, or about 1.775% w/w, or about 1.8% w/w of the antibacterial agent. In an aspect, a disclosed compounded composition comprising an antibacterial agent and an antifungal agent can comprise from about 2.0% w/w to about 9.0% w/w or from about 3.0% w/w to about 8.0% w/w of the antifungal agent. In various embodiments, first antibacterial comprises about 1% to about 1.9% w/w mupirocin and the antifungal comprises from about 0.2% to about 6% w/w voriconazole. In one example, the compounded composition comprises about 1.71% w/w mupirocin and 0.8% w/w voriconazole. The mupirocin may be mupirocin 2% cream or ointment in an amount approximately 85.7% w/w of the compounded composition and the voriconazole may include voriconazole for injection in an amount about 0.8% w/w of the compounded composition.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

3. A First Antibacterial Agent, a Second Antibacterial Agent, and an Antifungal Agent Disclosed herein is a method of making a compounded composition, the method comprising: mixing a therapeutically effective amount of a first antibacterial agent, a therapeutically effective amount of a second antibacterial agent, and a therapeutically effective amount of an antifungal agent to make a homogeneous compounded composition. A disclosed compounded composition can comprise a dry powder formulation or can comprise a cream or ointment.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art.

In an aspect, a disclosed method can comprise obtaining the first antibacterial agent, obtaining the second antibacterial agent, obtaining the antifungal agent, or a combination thereof. In an aspect, obtaining can comprise obtaining a bulk source of the first antibacterial agent, obtaining a bulk source of the second antibacterial agent, obtaining a bulk source of the antifungal agent, or a combination thereof.

In an aspect, a disclosed compounded composition comprising a first antibacterial agent, a second antibacterial agent, and an antifungal agent can comprise from about 1.0% w/w to about 3.0% w/w of the first antibacterial agent. In an aspect, a disclosed compounded composition comprising a first antibacterial agent, a second antibacterial agent, and an antifungal agent can comprise about 1.6% w/w, or about 1.756% w/w, or about 1.77% w/w, or about 1.775% w/w, or about 1.8% w/w of the first antibacterial agent. In an aspect, a disclosed compounded composition comprising a first antibacterial agent, a second antibacterial agent, and an antifungal agent can comprise from about 2.0% w/w to about 9.0% w/w or from about 3.0% w/w to about 8.0% w/w of the second antibacterial agent. In an aspect, a disclosed compounded composition comprising a first antibacterial agent, a second antibacterial agent, and an antifungal agent can comprise about 2.5% w/w, about 5.0% w/w, or about 7.5% w/w of the second antibacterial agent. In an aspect, a disclosed compounded composition comprising a first antibacterial agent, a second antibacterial agent, and an antifungal agent can comprise from about 2.0% w/w to about 9.0% w/w or from about 3.0% w/w to about 8.0% w/w of the antifungal agent. In an aspect, a disclosed compounded composition comprising a first antibacterial agent, a second antibacterial agent, and an antifungal agent can comprise about 2.5% w/w, about 5.0% w/w, or about 7.5% w/w of the antifungal agent.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin. In one example, the compounded composition comprises about 1.6% w/w mupirocin, about 0.8% w/w voriconazole, and about 4% w/w streptomycin. The mupirocin may be mupirocin 2% cream or ointment in an amount approximately 80% w/w of the compounded composition, the voriconazole may include voriconazole for injection in an amount about 0.8% w/w of the compounded composition, and the streptomycin may comprise streptomycin sulfate for injection in an amount about 5.528% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w streptomycin and about 0.2% to about 6% doxycycline. In one example, the compounded composition comprises about 1.55% w/w mupirocin, about 0.8% w/w voriconazole, about 4% w/w streptomycin, and about 1% w/w doxycycline. The mupirocin may be mupirocin 2% cream or ointment in an amount approximately 77.6% w/w of the compounded composition, the voriconazole may include voriconazole for injection in an amount about 0.8% w/w of the compounded composition, the streptomycin may comprise streptomycin sulfate for injection in an amount about 5.528% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w voriconazole, and the second antibacterial comprises from about 0.2% to about 6% w/w tobramycin and about 0.2% to about 6% doxycycline. In one example, the compounded composition comprises about 1.62% w/w mupirocin, about 0.8% w/w voriconazole, about 1.2% w/w tobramycin, and about 1% w/w doxycycline. The mupirocin may be mupirocin 2% cream or ointment in an amount approximately 81.3% w/w of the compounded composition, the voriconazole may include voriconazole for injection in an amount about 0.8% w/w of the compounded composition, the tobramycin may comprise tobramycin sulfate for injection in an amount about 1.8% w/w of the compounded composition, and the doxycycline may comprise doxycycline hyclate 100 mg tablets in an amount about 2.435% w/w of the compounded composition.

In various embodiments, first antibacterial comprises about 1% to about 1.9% w/w mupirocin, the antifungal comprises from about 0.2% to about 6% w/w ketoconazole, and the second antibacterial comprises from about 0.2% to about 6% w/w streptomycin and about 0.2% to about 6% doxycycline. In one example, the compounded composition comprises about 1.71% w/w mupirocin, about 2% w/w ketoconazole, about 4% w/w streptomycin, and about 2% w/w doxycycline. The mupirocin may be mupirocin 2% cream or ointment in an amount approximately 85.7% w/w of the compounded composition, the ketoconazole may include ketoconazole 200 mg tablets in an amount about 3.875% w/w of the compounded composition, the streptomycin may comprise streptomycin sulfate for injection in an amount about 5.528% w/w of the compounded composition, and the doxycycline may comprise doxycycline hyclate 100 mg tablets in an amount about 4.87% w/w of the compounded composition.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising a first antibacterial agent, a second antibacterial agent, and an antifungal agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising a first antibacterial agent, a second antibacterial agent, and an antifungal agent.

4. Mupirocin and an Antibacterial Agent

Disclosed herein is a method of making a compounded composition, the method comprising: mixing a therapeutically effective amount of mupirocin and a therapeutically effective amount of an antibacterial agent to make a homogeneous compounded composition. A disclosed compounded composition can comprise a dry powder formulation or can comprise a cream or ointment.

In an aspect, a disclosed method can comprise obtaining the mupirocin, obtaining the antibacterial agent, or a combination thereof. In an aspect, obtaining can comprise obtaining a bulk source of the mupirocin, obtaining a bulk source of the antibacterial agent, or a combination thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art.

In an aspect, a disclosed compounded composition comprising mupirocin and an antibacterial agent can comprise from about 1.0% w/w to about 3.0% w/w mupirocin. In an aspect, a disclosed compounded composition comprising mupirocin and an antibacterial agent can comprise about 1.6% w/w, or about 1.756% w/w, or about 1.77% w/w, or about 1.775% w/w, or about 1.8% w/w mupirocin. In an aspect, a disclosed compounded composition comprising mupirocin and an antibacterial agent can comprise from about 4.0% w/w to about 9.0% w/w or from about 6.0% w/w to about 8.0% w/w of the antibacterial agent. In an aspect, a disclosed compounded composition comprising mupirocin and an antibacterial agent can comprise about 5.0% w/w or about 7.5% w/w of the antibacterial agent.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and an antibacterial agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and an antibacterial agent.

Mupirocin and Tobramycin or a Salt Thereof

Disclosed herein is a method of making a compounded composition, the method comprising: mixing a therapeutically effective amount of mupirocin and a therapeutically effective amount of tobramycin or a pharmaceutically acceptable salt thereof to make a homogeneous compounded composition. A disclosed compounded composition can comprise a dry powder formulation or can comprise a cream or ointment.

In an aspect, a disclosed method can comprise obtaining the mupirocin, obtaining the tobramycin or a pharmaceutically acceptable salt thereof, or a combination thereof. In an aspect, obtaining can comprise obtaining a bulk source of the mupirocin, obtaining a bulk source of the tobramycin or a pharmaceutically acceptable salt thereof, or a combination thereof.

In an aspect, a disclosed compounded composition comprising mupirocin and tobramycin or a salt thereof can comprise from about 1.0% w/w to about 3.0% w/w mupirocin. In an aspect, a disclosed compounded composition comprising mupirocin and tobramycin or a salt thereof can comprise about 1.775% w/w mupirocin. In an aspect, a disclosed compounded composition comprising mupirocin and tobramycin or a salt thereof can comprise from about 7.0% to about 9.0% w/w of tobramycin or a pharmaceutically acceptable salt thereof. In an aspect, a disclosed compounded composition comprising mupirocin and tobramycin or a salt thereof can comprise about 7.5% w/w of tobramycin or a pharmaceutically acceptable salt thereof. In an aspect, a disclosed compounded composition comprising mupirocin and tobramycin or a salt thereof can comprise about 1.775% w/w mupirocin and about 7.5% w/w tobramycin or a pharmaceutically acceptable salt thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and tobramycin or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 1

In an aspect, to make 1 g of the compounded composition, which has about 1.775% w/w mupirocin and about 7.5% w/w tobramycin sulfate, about 0.8875 g of mupirocin 2.0% cream or ointment and about 0.1125 g of tobramycin sulfate for injection USP powder can be combined and mixed together according to a method described above.

Table 1 provides the approximate amount of mupirocin and tobramycin sulfate needed to make various amounts of the compounded composition.

TABLE 1

MUPIROCIN AND TOBRAMYCIN SULFATE

| Compounded Composition (in grams) | Mupirocin (2.0% cream or ointment) | Tobramycin Sulfate (for injection USP powder) |
| --- | --- | --- |
| 1 | 0.8875 g | 0.1125 g |
| 4 | 3.55 g | 0.45 g |
| 8 | 7.1 g | 0.90 g |
| 25 | 22.1875 g | 2.8125 g |
| 50 | 44.375 g | 5.625 g |
| 240 | 213.0 g | 27.0 g |
| 1500 | 1331.25 g | 168.75 g |

As used in Example 1, the term "about" means a value falling within a range that is ±10% of the stated value. In an aspect, the skilled person can combine 0.8875 g±10% mupirocin 2.0% cream or ointment (e.g., from about 0.79875 g-0.97625 g) and 0.1125 g±10% tobramycin sulfate for injection USP powder (e.g., from about 0.10125 g-0.12375 g) and mix together according to a method described above to make about 1.0 g±10% of the compounded composition.

Example 2

In an aspect, to make 1 g of the compounded composition, which has about 1.775% w/w mupirocin and about 7.5% w/w tobramycin, about 0.925 g of mupirocin 2.0% cream or ointment and about 0.075 g of pure or substantially pure tobramycin powder can be combined and mixed together according to a method described above.

Table 2 provides the approximate amount of mupirocin and pure or substantially pure tobramycin needed to make various amounts of the compounded composition.

TABLE 2

MUPIROCIN AND PURE OR SUBSTANTIALLY PURE TOBRAMYCIN

| Compounded Composition (in grams) | Mupirocin (2.0% cream or ointment) | Tobramycin (pure/substantially pure dry powder) |
|---|---|---|
| 1 | 0.925 g | 0.075 g |
| 4 | 3.7 g | 0.3 g |
| 8 | 7.4 g | 0.6 g |
| 25 | 23.125 g | 1.875 g |
| 50 | 46.25 g | 3.75 g |
| 240 | 222.0 g | 18.0 g |
| 1500 | 1387.5 g | 112.5 g |

As used in Example 2, the term "about" means a value falling within a range that is ±10% of the stated value. In an aspect, the skilled person can combine 0.925 g±10% mupirocin 2.0% cream or ointment (e.g., from about 0.8325 g-1.0175 g) and 0.075 g±10% pure or substantially pure dry tobramycin powder (e.g., from about 0.0675 g-0.0825 g and mix together according to a method described above to make about 1.0 g±10% of the compounded composition.

Mupirocin and Doxycycline or a Salt Thereof

Disclosed herein is a method of making a compounded composition, the method comprising: mixing a therapeutically effective amount of mupirocin and a therapeutically effective amount of doxycycline or a pharmaceutically acceptable salt thereof to make a homogeneous compounded composition. A disclosed compounded composition can comprise a dry powder formulation or can comprise a cream or ointment.

In an aspect, a disclosed method can comprise obtaining the mupirocin, obtaining the doxycycline or a pharmaceutically acceptable salt thereof, or a combination thereof. In an aspect, obtaining can comprise obtaining a bulk source of the mupirocin, obtaining a bulk source of the doxycycline or a pharmaceutically acceptable salt thereof, or a combination thereof.

In an aspect, a disclosed compounded composition comprising mupirocin and doxycycline or a salt thereof can comprise from about 1.0% w/w to about 3.0% w/w mupirocin. In an aspect, a disclosed compounded composition comprising mupirocin and doxycycline or a salt thereof can comprise about 1.756% w/w mupirocin. In an aspect, a disclosed compounded composition comprising mupirocin and doxycycline or a salt thereof can comprise from about 4.0% to about 6.0% w/w doxycycline or a pharmaceutically acceptable salt thereof. In an aspect, a disclosed compounded composition comprising mupirocin and doxycycline or a salt thereof can comprise about 5.0% w/w doxycycline or a pharmaceutically acceptable salt thereof. In an aspect, a disclosed compounded composition comprising mupirocin and doxycycline or a salt thereof can comprise about 1.756% w/w mupirocin and about 5.0% w/w doxycycline or a pharmaceutically acceptable salt thereof.

In an aspect, the formula presented below can be used to identify the approximate amount of powder from crushed doxycycline hyclate tablets needed for 1 g of the compounded composition:
0.878.8

In an aspect, the average weight of a doxycycline hyclate tablet can be about 0.2435 g and can comprise about 100 mg of doxycycline. In an aspect, using the above-identified formula, the amount of powder from crushed doxycycline hyclate tablets can be determined to be about 0.12175 g (or 121.75 mg).

$$\text{average tablet weight} \times \frac{\% \text{ of a tablet needed}}{(50\%)} = \text{amount of powder from crushed tablets needed} \\ (0.2435 \text{ g}) \qquad \qquad \qquad \qquad \qquad \qquad (0.12175 \text{ g})$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and doxycycline or a salt thereof into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and doxycycline or a salt thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and doxycycline or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 3

In an aspect, to make 1 g of the compounded composition, which has about 5.0% mupirocin and about 1.756% doxycycline or a pharmaceutically acceptable salt thereof, about 0.8782 g of mupirocin 2.0% cream or ointment and about 0.12175 g of powder from crushed doxycycline hyclate tablets can be combined and mixed together according to a method described above.

Table 3 provides the approximate amount of mupirocin and doxycycline hyclate needed to make various amounts of the compounded composition.

TABLE 3

MUPIROCIN AND DOXYCYCLINE HYCLATE

| Compounded Composition (in grams) | Mupirocin (2.0% cream or ointment) | Doxycycline Hyclate (powder from crushed tablets) |
|---|---|---|
| 1 | 0.8782 g | 0.12175 g |
| 4 | 3.5128 g | 0.487 g |
| 8 | 7.0256 g | 0.974 g |
| 25 | 21.955 g | 3.04375 g |
| 50 | 43.91 g | 6.0875 g |
| 240 | 210.768 g | 29.22 g |
| 1500 | 1317.3 g | 182.625 g |

As used in Example 3, the term "about" means a value falling within a range that is ±10% of the stated value. In an aspect, the skilled person can combine 0.8782 g±10% mupirocin 2.0% cream or ointment (e.g., from about 0.79038 g-0.96602 g) and 0.12175 g±10% powder from crushed doxycycline hyclate tablets (e.g., from about 0.109575 g-0.133925 g) and mix together according to a method described above to make about 1.0 g±10% of the compounded composition.

Example 4

In an aspect, to make 1 g of the compounded composition, which has about 5.0% mupirocin and about 1.756% doxycycline, about 0.950 g of mupirocin 2.0% cream or ointment and about 0.050 g of pure or substantially pure doxycycline powder can be combined and mixed together according to a method described above.

Table 4 provides the approximate amount of mupirocin and pure or substantially pure doxycycline needed to make various amounts of the compounded composition.

TABLE 4

MUPIROCIN AND PURE OR SUBSTANTIALLY PURE DOXYCYCLINE

| Compounded Composition (in grams) | Mupirocin (2.0% cream or ointment) | Doxycycline (pure/substantially pure dry powder) |
|---|---|---|
| 1 | 0.950 g | 0.050 g |
| 4 | 3.8 g | 0.2 g |
| 8 | 7.6 g | 0.4 g |
| 25 | 23.75 g | 1.25 g |
| 50 | 47.5 g | 2.5 g |
| 240 | 228.0 g | 12.0 g |
| 1500 | 1425.0 g | 75.0 g |

As used in Example 4, the term "about" means a value falling within a range that is ±10% of the stated value. In an aspect, the skilled person can combine 0.950 g±10% mupirocin 2.0% cream or ointment (e.g., from about 0.855 g-1.045 g) and 0.050 g±10% pure or substantially pure doxycycline dry powder (e.g., from about 0.045 g-0.055 g) and mix together according to a method described above to make about 1.0 g±10% of the compounded composition.

Mupirocin and Azithromycin

A method of making a compounded composition, the method comprising: mixing a therapeutically effective amount of mupirocin and a therapeutically effective amount of azithromycin to make a homogeneous compounded composition. A disclosed compounded composition can comprise a dry powder formulation or can comprise a cream or ointment.

In an aspect, a disclosed method can comprise obtaining the mupirocin, obtaining the azithromycin, or a combination thereof. In an aspect, obtaining can comprise obtaining a bulk source of the mupirocin, obtaining a bulk source of the azithromycin, or a combination thereof.

In an aspect, a disclosed compounded composition comprising mupirocin and azithromycin can comprise from about 1.0% w/w to about 3.0% w/w mupirocin. In an aspect, a disclosed compounded composition comprising mupirocin and azithromycin can comprise about 1.8% w/w mupirocin. In an aspect, a disclosed compounded composition comprising mupirocin and azithromycin can comprise from about 4.0% w/w to about 6.0% w/w azithromycin. In an aspect, a disclosed compounded composition comprising mupirocin and azithromycin can comprise about 5.0% w/w azithromycin. In an aspect, a disclosed compounded composition comprising mupirocin and azithromycin can comprise about 1.8% w/w mupirocin and about 5.0% w/w azithromycin.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and azithromycin into a container and sealing the container. In an aspect, a container can be a container disclosed herein. In an aspect, a disclosed method can comprise sterilizing the compounded composition comprising mupirocin and azithromycin.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and azithromycin can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 5

In an aspect, to make 1 g of the compounded composition, which has about 1.8% w/w mupirocin and about 5.0% w/w azithromycin, about 0.9 g of mupirocin 2.0% cream or ointment and about 0.10 g of azithromycin for injection USP powder (500 mg azithromycin/1 g powder) can be combined and mixed together according to a method described above.

Table 5 provides the approximate amount of mupirocin and azithromycin needed to make various amounts of the compounded composition.

TABLE 5

MUPIROCIN AND AZITHROMYCIN

| Compounded Composition (in grams) | Mupirocin (2.0% cream or ointment) | Azithromycin (500 mg/1 g powder for injection USP) |
|---|---|---|
| 1 | 0.9 g | 0.10 g |
| 4 | 3.6 g | 0.40 g |
| 8 | 7.2 g | 0.80 g |
| 25 | 22.5 g | 2.5 g |
| 50 | 45.0 g | 5.0 g |
| 240 | 216.0 g | 24.0 g |
| 1500 | 1350.0 g | 150.0 g |

As used in Example 5, the term "about" means a value falling within a range that is ±10% of the stated value. In an aspect, the skilled person can combine 0.90 g±10% mupirocin 2.0% cream or ointment (e.g., from about 0.81 g-0.99 g) and 0.10 g±10% azithromycin powder for injection USP (e.g., from about 0.09 g-0.11 g) and mix together according to a method described above to make about 1.0 g±10% of the compounded composition.

Mupirocin and Ciprofloxacin or a Salt Thereof

Disclosed herein is a method of making a compounded composition, the method comprising: mixing a therapeutically effective amount of mupirocin and a therapeutically effective amount of ciprofloxacin or a pharmaceutically acceptable salt thereof to make a homogeneous compounded composition. A disclosed compounded composition can comprise a dry powder formulation or can comprise a cream or ointment.

In an aspect, a disclosed method can comprise obtaining the mupirocin, obtaining the ciprofloxacin or a pharmaceutically acceptable salt thereof, or a combination thereof. In an aspect, obtaining can comprise obtaining a bulk source of the mupirocin, obtaining a bulk source of ciprofloxacin or a pharmaceutically acceptable salt thereof, or a combination thereof.

In an aspect, a disclosed compounded composition comprising mupirocin and ciprofloxacin or salt thereof can comprise from about 1.0% w/w to about 3.0% w/w, from about 1.2% w/w to about 2.5% w/w, from about 1.4% w/w to about 2.3% w/w, from about 1.4% w/w to about 2.2% w/w, from about 1.5% w/w to about 2.1% w/w, from about 1.6% w/w to about 2.0% w/w, from about 1.7% w/w to about 2.0% w/w, or from about 1.8% w/w to about 2.0% w/w mupirocin. In an aspect, a disclosed compounded composition comprising mupirocin and ciprofloxacin or salt thereof can comprise from about 1.0% w/w to about 5.0% w/w, from about 1.0% w/w to about 3.0% w/w, or from about 1.5% w/w to about 2.5% w/w ciprofloxacin or a pharmaceutically acceptable thereof. In an aspect, a disclosed compounded composition comprising mupirocin and ciprofloxacin or salt thereof can comprise from about 1.8% w/w to about 2.0% w/w mupirocin and from about 1.0% w/w to about 3.0% w/w ciprofloxacin or a pharmaceutically acceptable thereof. In an aspect, a disclosed compounded composition comprising mupirocin and ciprofloxacin or salt thereof can comprise about 1.95% w/w mupirocin and about 2.0% w/w ciprofloxacin or a pharmaceutically acceptable salt thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and ciprofloxacin or salt thereof into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and ciprofloxacin or salt thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and ciprofloxacin or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 6

In an aspect, to make 1 g of the compounded composition, which has about 1.95% w/w mupirocin and about 2.0% w/w ciprofloxacin, about 0.9767 g of mupirocin 2.0% cream or ointment and about 0.023288 g of ciprofloxacin HCl USP monohydrate can be combined and mixed together according to a method described above.

Table 6 provides the approximate amount of mupirocin and ciprofloxacin hydrochloride needed to make various amounts of the compounded composition.

TABLE 6

MUPIROCIN AND CIPROFLOXACIN HYDROCHLORIDE

| Compounded Composition (in grams) | Mupirocin (2.0% cream or ointment) | Ciprofloxacin HCl (USP monohydrate) |
|---|---|---|
| 1 | 0.9767 g | 0.023288 g |
| 4 | 3.9068 g | 0.093152 g |
| 8 | 7.8136 g | 0.186304 g |
| 25 | 24.4175 g | 0.5822 g |
| 50 | 48.835 g | 1.1644 g |
| 240 | 234.408 g | 5.58912 g |
| 1500 | 1465.05 g | 34.932 g |

As used in Example 6, the term "about" means a value falling within a range that is ±10% of the stated value. In an aspect, the skilled person can combine 0.9767 g±10% mupirocin 2.0% cream or ointment (e.g., from about 0.87903 g-1.07437 g) and 0.02328 g±10% ciprofloxacin HCl monohydrate powder (e.g., from about 0.02095 g-0.025616 g) and mix together according to a method described above to make about 1.0 g±10% of the compounded composition.

Mupirocin and Clindamycin or a Salt Thereof

Disclosed herein is method of making a compounded composition, the method comprising: mixing a therapeutically effective amount of mupirocin and a therapeutically effective amount of clindamycin or a pharmaceutically acceptable salt thereof to make a homogeneous compounded composition. A disclosed compounded composition can comprise a dry powder formulation or can comprise a cream or ointment.

In an aspect, a disclosed method can comprise obtaining the mupirocin, obtaining the clindamycin or a pharmaceutically acceptable salt thereof, or a combination thereof. In an aspect, obtaining can comprise obtaining a bulk source of the mupirocin, obtaining a bulk source of the clindamycin or a pharmaceutically acceptable salt thereof, or a combination thereof.

In an aspect, a disclosed compounded composition comprising mupirocin and clindamycin or a salt thereof can comprise from about 1.0% w/w to about 3.0% w/w mupirocin. In an aspect, a disclosed compounded composition comprising mupirocin and clindamycin or a salt thereof can comprise about 1.88% w/w mupirocin. In an aspect, a disclosed compounded composition comprising mupirocin and clindamycin or a salt thereof can comprise from about 4.0% to about 6.0% w/w clindamycin or a pharmaceutically acceptable salt thereof. In an aspect, a disclosed compounded composition comprising mupirocin and clindamycin or a salt thereof can comprise about 5.0% w/w clindamycin or a pharmaceutically acceptable salt thereof. In an aspect, a disclosed compounded composition comprising mupirocin and clindamycin or a salt thereof can comprise about 1.88% w/w mupirocin and about 5.0% w/w clindamycin or a pharmaceutically acceptable salt thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and clindamycin or a salt thereof into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and clindamycin or a salt thereof.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and clindamycin or a pharmaceutically acceptable salt thereof can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 7

In an aspect, to make about 1.0 g of the compounded composition, which has about 1.88% mupirocin and about 5.0% clindamycin or a pharmaceutically acceptable salt thereof, about 0.940 g of mupirocin 2.0% cream or ointment and about 0.050 g of clindamycin hydrochloride USP powder be combined and mixed together according to a method described above.

Table 7 provides the approximate amount of mupirocin and clindamycin hydrochloride needed to make various amounts of the compounded composition.

TABLE 7

MUPIROCIN AND CLINDAMYCIN HYDROCHLORIDE

| Compounded Composition (in grams) | Mupirocin (2.0% cream or ointment) | Clindamycin HCl (USP powder) |
|---|---|---|
| ~1 | 0.94 g | 0.050 g |
| ~4 | 3.8 g | 0.20 g |

TABLE 7-continued

MUPIROCIN AND CLINDAMYCIN HYDROCHLORIDE

| Compounded Composition (in grams) | Mupirocin (2.0% cream or ointment) | Clindamycin HCl (USP powder) |
|---|---|---|
| ~8 | 7.6 g | 0.40 g |
| ~25 | 23.75 g | 1.25 g |
| ~50 | 47.5 g | 2.5 g |
| ~240 | 228.0 g | 12.0 g |
| ~1500 | 1425.0 g | 75.0 g |

As used in Example 7, the term "about" means a value falling within a range that is ±10% of the stated value. In an aspect, the skilled person can combine 0.95 g±10% mupirocin 2.0% cream or ointment (e.g., from about 0.855 g-1.045 g) and 0.05 g±10% clindamycin HCl powder USP (e.g., from about 0.045 g-0.055 g) and mix together according to a method described above to make about 1.0 g±10% of the compounded composition.

5. Mupirocin and an Antifungal Agent Disclosed herein is a method of making a compounded composition, the method comprising: mixing a therapeutically effective amount of mupirocin and a therapeutically effective amount of an antifungal agent to make a homogeneous compounded composition. A disclosed compounded composition can comprise a dry powder formulation or can comprise a cream or ointment.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise obtaining the mupirocin, obtaining the antifungal agent, or a combination thereof. In an aspect, obtaining can comprise obtaining a bulk source of the mupirocin, obtaining a bulk source of the antifungal agent, or a combination thereof.

In an aspect, a disclosed compounded composition comprising mupirocin and an antifungal agent can comprise from about 1.0% w/w to about 3.0% w/w of the mupirocin. In an aspect, a disclosed compounded composition comprising mupirocin and an antifungal agent can comprise about 1.6% w/w, or about 1.756% w/w, or about 1.77% w/w, or about 1.775% w/w, or about 1.8% w/w of the mupirocin. In an aspect, a disclosed compounded composition comprising mupirocin and an antifungal agent from about 4.0% w/w to about 9.0% w/w or from about 6.0% w/w to about 8.0% w/w of the antifungal agent. In an aspect, a disclosed compounded composition comprising mupirocin and an antifungal agent can comprise about 2.5% w/w, about 5.0% w/w, or about 7.5% w/w of the antifungal agent.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and an antifungal agent into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and an antifungal agent.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art.

Mupirocin and Ketoconazole

Disclosed herein is a method of making a compounded composition, the method comprising: mixing a therapeutically effective amount of mupirocin and a therapeutically effective amount of ketoconazole to make a homogeneous compounded composition. A disclosed compounded composition can comprise a dry powder formulation or can comprise a cream or ointment.

In an aspect, a disclosed method can comprise obtaining the mupirocin, obtaining the ketoconazole, or a combination thereof. In an aspect, obtaining can comprise obtaining a bulk source of the mupirocin, obtaining a bulk source of ketoconazole, or a combination thereof.

In an aspect, a disclosed compounded composition comprising mupirocin and ketoconazole can comprise from about 1.0% w/w to about 3.0% w/w mupirocin. In an aspect, a disclosed compounded composition comprising mupirocin and ketoconazole can comprise about 1.77% w/w mupirocin. In an aspect, a disclosed compounded composition comprising mupirocin and ketoconazole can comprise from about 6.5% w/w to about 8.5% w/w ketoconazole. In an aspect, a disclosed compounded composition comprising mupirocin and ketoconazole can comprise about 7.5% w/w ketoconazole. In an aspect, a disclosed compounded composition comprising mupirocin and ketoconazole can comprise about 1.77% w/w mupirocin and about 7.5% w/w ketoconazole.

The formula presented below can be used to identify the identify the approximate amount of powder from crushed ketoconazole tablets needed for 1 gram of the compounded composition: avg. tablet weight (g)×% of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets can be determined to be about 0.11625 g (or 116.25 mg).

$$\text{average tablet weight} \times \text{\% of a tablet needed} = $$
$$(0.310 \text{ g}) \quad\quad (37.5\%)$$
$$\text{amount of powder from crushed tablets needed}$$
$$(0.11625 \text{ g})$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 8

In an aspect, to make 1 g of the compounded composition, which has about 1.77% w/w mupirocin and about 7.5% w/w ketoconazole, about 0.8838 g of mupirocin 2.0% cream or ointment and about 0.11625 g of powder from crushed ketoconazole tablets can be combined and mixed together according to a method described above.

Table 8 provides the approximate amount of mupirocin and ketoconazole needed to make various amounts of the compounded composition.

TABLE 8

MUPIROCIN AND KETOCONAZOLE

| Compounded Composition (in grams) | Mupirocin (2.0% cream or ointment) | Ketoconazole (powder from crushed tablets) |
| --- | --- | --- |
| 1 | 0.8838 g | 0.11625 g |
| 4 | 3.5352 g | 0.465 g |
| 8 | 7.0704 g | 0.93 g |
| 25 | 22.095 g | 2.90625 g |
| 50 | 44.19 g | 5.8125 g |
| 240 | 212.112 g | 27.9 g |
| 1500 | 1325.7 g | 174.375 g |

As used in Example 8, the term "about" means a value falling within a range that is ±10% of the stated value. In an aspect, the skilled person can combine 0.8838 g±10% mupirocin 2.0% cream or ointment (e.g., from about 0.79542 g-0.97218 g) and 0.11625 g±10% powder from crushed ketoconazole tablets (e.g., from about 0.104625 g-0.127875 g) and mix together according to a method described above to make about 1.0 g±10% of the compounded composition.

Mupirocin and Nystatin

Disclosed herein is method of making a compounded composition, the method comprising: mixing a therapeutically effective amount of mupirocin and a therapeutically effective amount of nystatin to make a homogeneous compounded composition. A disclosed compounded composition can comprise a dry powder formulation or can comprise a cream or ointment.

In an aspect, a disclosed method can comprise obtaining the mupirocin, obtaining the nystatin powder, or a combination thereof. In an aspect, obtaining can comprise obtaining a bulk source of the mupirocin, obtaining a bulk source of the nystatin powder, or a combination thereof.

In an aspect, a disclosed compounded composition comprising mupirocin and nystatin can comprise from about 1.0% w/w to about 3.0% w/w mupirocin. In an aspect, a disclosed compounded composition comprising mupirocin and nystatin can comprise about 1.60% w/w mupirocin. In an aspect, a disclosed compounded composition comprising mupirocin and nystatin can comprise from about 15,000 units per gram to about 25,000 units per gram nystatin. In an aspect, a disclosed compounded composition comprising mupirocin and nystatin can comprise about 20,000 units per gram nystatin. In an aspect, a disclosed compounded composition comprising mupirocin and nystatin can comprise about 1.60% w/w mupirocin and about 20,000 units per gram nystatin.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition mupirocin and nystatin into a container and sealing the container. In an aspect, a container can be a container disclosed herein, such as, for example, a plastic tube, a glass or non-glass vial, a syringe, etc. In an aspect, a disclosed method can comprise sterilizing the compounded composition mupirocin and nystatin.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin and nystatin can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 9

In an aspect, to make 1 g of the compounded composition, which has about 1.6% w/w mupirocin and about 20,000 units/g nystatin, about 0.80 g of mupirocin 2.0% cream or ointment and about 0.20 g of nystatin powder (100,000 units/g) can be combined and mixed together according to a method described above.

Table 9 provides the approximate amount of mupirocin and nystatin needed to make various amounts of the compounded composition.

TABLE 9

MUPIROCIN AND NYSTATIN

| Compounded Composition (in grams) | Mupirocin (2.0% cream or ointment) | Nystatin Powder (100,000 units/gram) |
|---|---|---|
| 1 | 0.80 g | 0.20 g |
| 4 | 3.2 g | 0.80 g |
| 8 | 6.4 g | 1.6 g |
| 25 | 20.0 g | 5.0 g |
| 50 | 40.0 g | 10.0 g |
| 240 | 192.0 g | 48.0 g |
| 1500 | 1200.0 g | 300.0 g |

As used in Example 9, the term "about" means a value falling within a range that is ±10% of the stated value. In an aspect, the skilled person can combine 0.80 g±10% mupirocin 2.0% cream or ointment (e.g., from about 0.72 g-0.88 g) and 0.20 g±10% nystatin (e.g., from about 0.18 g-0.22 g) and mix together according to a method described above to make about 1.0 g 10% of the compounded composition.

6. Mupirocin, an Antibacterial Agent, and an Antifungal Agent

Disclosed herein is a method of making a compounded composition, the method comprising: mixing a therapeutically effective amount of mupirocin, a therapeutically effective amount of an antibacterial agent, and a therapeutically effective amount of an antifungal agent to make a homogeneous compounded composition. A disclosed compounded composition can comprise a dry powder formulation or can comprise a cream or ointment.

In an aspect, a disclosed method can comprise obtaining the mupirocin, obtaining the antibacterial agent, obtaining the antifungal agent, or a combination thereof. In an aspect, obtaining can comprise obtaining a bulk source of the mupirocin, obtaining a bulk source of the antibacterial agent, obtaining a bulk source of the antifungal agent, or a combination thereof. In an aspect, obtaining can comprise crushing oral tablets containing an antibacterial or antifungal. In an aspect, obtaining can comprise obtaining a cream or ointment of an antibacterial or antifungal.

In an aspect, a disclosed compounded composition comprising mupirocin, an antibacterial agent, and an antifungal agent can comprise from about 1.0% w/w to about 3.0% w/w mupirocin. In an aspect, a disclosed compounded composition comprising mupirocin, an antibacterial agent, and an antifungal agent can comprise about 1.6% w/w, or about 1.7% w/w or about 1.756% w/w, or about 1.77% w/w, or about 1.775% w/w, or about 1.8% w/w mupirocin. In an aspect, a disclosed compounded composition comprising mupirocin, an antibacterial agent, and an antifungal agent can comprise from about 4.0% w/w to about 9.0% w/w or from about 6.0% w/w to about 8.0% w/w of the antibacterial agent. In an aspect, a disclosed compounded composition comprising mupirocin, an antibacterial agent, and an antifungal agent can comprise about 5.0% w/w or about 7.5% w/w of the antibacterial agent. In an aspect, a disclosed compounded composition comprising mupirocin, an antibacterial agent, and an antifungal agent can comprise from about 4.0% w/w to about 9.0% w/w or from about 6.0% w/w to about 8.0% w/w of the antifungal agent. In an aspect, a disclosed compounded composition comprising mupirocin, an antibacterial agent, and an antifungal agent can comprise about 5.0% w/w or about 7.5% w/w of the antifungal agent.

In an aspect, a disclosed compounded composition comprises a therapeutically effective amount of mupirocin, a therapeutically effective amount of an additional or second antibacterial agent, and a therapeutically effective amount of an antifungal agent selected from one or more antifungals described herein, such as one or more of ketoconazole, voriconazole, or amphotericin B. The second antibacterial agent may comprise one or more of doxycycline, bacitracin, colistimethate, piperacillin-tazobactam, polymyxin B, or streptomycin. In one embodiment, the second antibacterial agent comprises doxycycline and one or more of bacitracin, colistimethate, piperacillin-tazobactam, polymyxin B, or streptomycin. Other antibacterials may be used in addition to or instead of doxycycline, bacitracin, colistimethate, piperacillin-tazobactam, polymyxin B, or streptomycin, such as the antibacterials described herein.

In one embodiment, a disclosed compounded composition comprising mupirocin and doxycycline or a salt thereof comprises an antifungal agent comprising ketoconazole. In an aspect, a disclosed compounded composition can comprise about 1.6% w/w mupirocin, about 5.0% w/w doxycycline or a pharmaceutically acceptable salt thereof, and about 5.0% w/w ketoconazole. In an aspect, a disclosed compounded composition can comprise about 1.8% w/w mupirocin, about 2.5% w/w doxycycline or a pharmaceutically acceptable salt thereof, and about 2.5% w/w ketoconazole.

In an aspect, a disclosed compounded composition can comprise mupirocin, an antifungal agent, and a second antibacterial agent. In one example, the antifungal agent includes ketoconazole and the second antibacterial agent includes one or more antibacterials (which may include pharmaceutically acceptable salts) selected from bacitracin, colistimethate, piperacillin-tazobactam, polymyxin B, streptomycin, or doxycycline. In one such example, the antifungal agent includes ketoconazole and the second antibacterial agent includes doxycycline and one or more antibacterials selected from bacitracin, colistimethate, piperacillin-tazobactam, polymyxin B, or streptomycin. In an aspect, the mupirocin can comprise a cream or ointment (for example, a mupirocin 2.0% cream or ointment), the doxycycline or a pharmaceutically acceptable salt thereof can comprise a dry powder, and the ketoconazole can comprise a dry powder. In an aspect, a disclosed compounded composition can comprise from about 1.6% to about 1.8% w/w mupirocin, from about 1.0% to about 5.0% w/w doxycycline or a pharmaceutically acceptable salt thereof, and from about 1.0% to about 5.0% w/w ketoconazole. In an aspect, a disclosed compounded composition can comprise from about 1.6 to about 1.7% w/w mupirocin, from about 1.0% to about 5.0% w/w doxycycline, from about 2% to about 6% w/w streptomycin, and from about 1.0% to about 5.0% w/w ketoconazole. In another embodiment, streptomycin may be replaced by about antibacterial. For example, streptomycin may be replaced by an antibacterial selected from bacitracin, colistimethate, piperacillin-tazobactam, or polymyxin B in an amount from about 2% to about 6% w/w. In another embodiment, streptomycin may be replaced by an antifungal. For example, streptomycin may be replaced by an antifungal selected from voriconazole or amphotericin B in an amount from about 1% to about 5% w/w. In one example, a disclosed compounded composition can comprise about 1.7% w/w mupirocin, about 2% w/w doxycycline, about 4% w/w streptomycin, and about 2.5% w/w ketoconazole.

In one aspect, a disclosed compounded composition comprises a compounded cream or ointment comprising doxycycline, tobramycin, mupirocin, and ketoconazole. The doxycycline may comprise crushed doxycycline hyclate tablets, e.g., 100 mg tablets. The tobramycin may comprise tobramycin sulfate for injection powder. The mupirocin may comprise mupirocin 2% cream or ointment. The ketoconazole may comprise crushed ketoconazole tablets, e.g., 200 mg tablets.

A method of compounding a compounded composition comprising mupirocin, doxycycline, streptomycin, and ketoconazole may comprise grinding a suitable amount of doxycycline hyclate tablets and ketoconazole tablets and combining the powder from the crushed tablets with a suitable amount of streptomycin sulfate for injection powder and a suitable volume of mupirocin 2% cream or ointment. For example, compounding a compounded composition comprising about 2% w/w doxycycline, about 1.71% w/w mupirocin, about 4% w/w streptomycin, and about 2.5% w/w ketoconazole may include crushing doxycycline hyclate tablets and ketoconazole tablets and combining the powder from the crushed tablets with a suitable amount of tobramycin sulfate for injection powder and a suitable volume of mupirocin 2% cream or ointment. Each gram of the compounded composition contains about 2% doxycycline (or 20 mg doxycycline), which is equivalent to 0.20 tablets of 100 mg doxycycline tablets, which is equivalent to about 48.7 mg (20% of 243.5 mg total weight of a 100 mg doxycycline tablet). Each gram of compounded composition contains about 2.5% ketoconazole (or 25 mg ketoconazole) which is equivalent to about 0.125 tablets of 200 mg ketoconazole tablets, which is equivalent to about 38.75 mg (25% of 310 mg total weight of a 100 mg ketoconazole tablet). Each gram of compounded composition contains about 4% streptomycin, equivalent to about 40 mg streptomycin USP, equivalent to about 55.28 mg of streptomycin sulfate, which may reflect usage of about 4% of 1 vial of streptomycin 1 g vials per gram of compounded composition. The powders may be added to a suitable amount of mupirocin cream or mupirocin ointment to formulate the desired concentration of the compounded composition cream or ointment. For example, for every gram of compounded composition cream or ointment, the powders may be combined with about 0.863 g of mupirocin 2% cream or ointment. The combined mixture may be suitably processed in an ointment mill as described elsewhere herein. The compounded composition may be packaged in suitable packaging, e.g., tubes or syringes. As noted elsewhere herein, the term "about" means a value falling within a range that is ±10% of the stated value. Thus, in an aspect, the skilled person can combine 0.8573 g±10% mupirocin 2.0% cream or ointment, 0.0487 g±10% powder from crushed doxycycline hyclate 100 mg tablets, 0.05528 g±10% streptomycin sulfate USP powder for injection, and 0.03875 g±10% powder from crushed ketoconazole 200 mg tablets and mix together according to a method described above to make about 1.0 g±10% of the compounded composition. Other strength tablets and creams or ointments may be used wherein amounts combined are suitably adjusted.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition into a container and sealing the container. In an aspect, a container can be a container disclosed herein, such as, for example, a plastic tube, a glass or non-glass vial, a syringe, etc. In an aspect, a disclosed method can comprise sterilizing the compounded composition.

In an aspect, the mixing can comprise using an electronic mortar and pestle (EMP). In an aspect, a disclosed method can comprise milling the mixture of ingredients (using, for example, a three-roll mill). Mixing and milling can be done according to standards known to the skilled person in the art.

In one example, a method of making a compounded composition comprising 1.7% w/w mupirocin, about 2% w/w doxycycline, about 4% w/w streptomycin, and about 2.5% w/w ketoconazole comprises obtaining mupirocin, doxycycline, streptomycin, and ketoconazole. In an aspect, mupirocin may comprise mupirocin 2% cream or ointment and can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, the average weight of a ketoconazole tablet can be about 0.310 grams and can comprise about 200 mg of ketoconazole. In an aspect, the formula presented below can be used to identify the approximate amount of powder from crushed commercially available ketoconazole tablets needed for 1 g of the compounded composition:

$$\text{avg. tablet weight (g)} \times \frac{\% \text{ of a tablet needed}}{(25.0\%)} = \text{amt. of powder from crushed tablets needed (g)} \atop (0.0775 \text{ g})$$
$$(0.3100 \text{ g})$$

In an aspect, a disclosed compounded composition comprising mupirocin, tobramycin or a salt thereof, and ketoconazole can comprise from about 1.4% w/w to about 2.0% w/w, from about 1.5% w/w to about 1.9% w/w, or from about 1.6% w/w to about 1.8% w/w mupirocin. In an aspect, a disclosed compounded composition comprising mupirocin, tobramycin or a salt thereof, and ketoconazole can comprise about 1.695% w/w or about 1.8475% w/w mupirocin. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w tobramycin or a pharmaceutically acceptable salt thereof. In an aspect, a disclosed compounded composition comprising mupirocin, tobramycin or a salt thereof, and ketoconazole can comprise about 2.5% w/w or about 5.0% w/w tobramycin or a pharmaceutically acceptable salt thereof. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w ketoconazole. In an aspect, a disclosed compounded composition comprising mupirocin, tobramycin or a salt thereof, and ketoconazole can comprise about 2.5% w/w or 5.0% w/w ketoconazole.

In an aspect, a disclosed compounded composition comprising mupirocin, tobramycin or a salt thereof, and ketoconazole can comprise from about 1.695% w/w mupirocin, about 5.0% w/w tobramycin or a pharmaceutically acceptable salt thereof, and about 5.0% w/w ketoconazole.

In an aspect, a disclosed compounded composition comprising mupirocin, tobramycin or a salt thereof, and ketoconazole can comprise from about 1.8475% w/w mupirocin, about 2.5% w/w tobramycin or a pharmaceutically acceptable salt thereof, and about 2.5% w/w ketoconazole.

In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, tobramycin or a salt thereof, and ketoconazole into a container and sealing the container. In an aspect, a container can be a container disclosed herein, such as, for example, a syringe. In an aspect, a disclosed method can comprise sterilizing the compounded composition comprising mupirocin, tobramycin or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, tobramycin or a pharmaceutically acceptable salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 13

In an aspect, to make 1 g of the compounded composition, which has about 1.8475% w/w mupirocin, about 2.5% w/w tobramycin or a pharmaceutically acceptable salt thereof, and about 2.5% w/w ketoconazole, about 0.92375 g of mupirocin 2.0% cream or ointment, about 0.0375 g of tobramycin sulfate for injection USP powder, and about 0.03875 g of powder from crushed ketoconazole tablets.

Table 13 provides the approximate amount of mupirocin, tobramycin sulfate, and ketoconazole needed to make various amounts of the compounded composition.

TABLE 13

| MUPIROCIN, TOBRAMYCIN SULFATE, AND KETOCONAZOLE | | | |
|---|---|---|---|
| Compounded Composition (in grams) | Mupirocin (2.0% cream or ointment) | Tobramycin Sulfate (USP powder for injection) | Ketoconazole (powder from crushed tablets) |
| 1 | 0.92375 g | 0.0375 g | 0.03875 g |
| 4 | 3.695 g | 0.15 g | 0.155 g |

TABLE 13-continued

MUPIROCIN, TOBRAMYCIN SULFATE, AND KETOCONAZOLE

| Compounded Composition (in grams) | Mupirocin (2.0% cream or ointment) | Tobramycin Sulfate (USP powder for injection) | Ketoconazole (powder from crushed tablets) |
|---|---|---|---|
| 8 | 7.39 g | 0.30 g | 0.31 g |
| 25 | 23.09375 g | 0.9375 g | 0.96875 g |
| 50 | 46.1875 g | 1.875 g | 1.9375 g |
| 240 | 221.7 g | 9.0 g | 9.3 g |
| 1500 | 1385.625 g | 56.25 g | 58.125 g |

As used in Example 13, the term "about" means a value falling within a range that is ±10% of the stated value. In an aspect, the skilled person can combine 0.92375 g±10% mupirocin 2.0% cream or ointment (e.g., from about 0.8313 g-1.0161 g), 0.0375 g±10% tobramycin sulfate USP powder for injection (e.g., from about 0.03375 g-0.04125 g), and 0.03875 g±10% powder from crushed ketoconazole tablets (e.g., from about 0.03487 g-0.04262 g) and mix together according to a method described above to make about 1.0 g±10% of the compounded composition.

Mupirocin, Doxycycline or a Salt Thereof, and Fluconazole

Disclosed herein is a method of making a compounded composition, the method comprising: mixing a therapeutically effective amount of mupirocin, a therapeutically effective amount of doxycycline or a pharmaceutically acceptable salt thereof, and a therapeutically effective amount of fluconazole to make a homogeneous compounded composition. A disclosed compounded composition can comprise a dry powder formulation or can comprise a cream or ointment.

In an aspect, a disclosed method can comprise obtaining the mupirocin, obtaining the doxycycline or a pharmaceutically acceptable salt thereof, obtaining the fluconazole, or a combination thereof. In an aspect, obtaining can comprise obtaining a bulk source of the mupirocin, obtaining a bulk source of the doxycycline or a pharmaceutically acceptable salt thereof, obtaining a bulk source of the fluconazole, or a combination thereof.

In an aspect, a disclosed compounded composition comprising mupirocin, doxycycline or a salt thereof, and fluconazole can comprise from about 1.0% w/w to about 3.0% w/w mupirocin. In an aspect, a disclosed compounded composition comprising mupirocin, doxycycline or a salt thereof, and fluconazole can comprise about 1.655% w/w mupirocin. In an aspect, a disclosed compounded composition comprising mupirocin, doxycycline or a salt thereof, and fluconazole can comprise from about 1.5% w/w to about 3.5% w/w fluconazole. In an aspect, a disclosed compounded composition comprising mupirocin, doxycycline or a salt thereof, and fluconazole can comprise about 2.5% w/w fluconazole. In an aspect, a disclosed compounded composition comprising mupirocin, doxycycline or a salt thereof, and fluconazole can comprise from about 4.0% to about 6.0% w/w doxycycline or the pharmaceutically acceptable salt thereof. In an aspect, a disclosed compounded composition comprising mupirocin, doxycycline or a salt thereof, and fluconazole about 5.0% w/w doxycycline or a pharmaceutically acceptable salt thereof. In an aspect, a disclosed compounded composition comprising mupirocin, doxycycline or a salt thereof, and fluconazole can comprise about 1.655% w/w mupirocin, about 5.0% w/w doxycycline or a pharmaceutically acceptable salt thereof, and about 2.5% w/w fluconazole. In an aspect, the formula presented below can be used to identify the approximate amount of powder from crushed doxycycline hyclate tablets needed for 1 g of the compounded composition: avg. tablet weight (g)×% of a tablet needed=amt. of powder from crushed tablets needed (g)

In an aspect, the average weight of a doxycycline hyclate tablet can be about 0.2435 grams and can comprise about 100 mg of doxycycline. In an aspect, using the above-identified formula, the amount of powder from crushed doxycycline hyclate tablets can be determined to be about 0.12175 g (or 121.75 mg).

$$\text{average tablet weight} \times \text{\% of a tablet needed} =$$
$$(0.2435 \text{ g}) \quad (50\%)$$
$$\text{amount of powder from crushed tablets needed}$$
$$(0.12175 \text{ g})$$

In an aspect, the formula presented below can be used to identify the approximate amount of powder from crushed fluconazole tablets needed for 1 g of the compounded composition:

In an aspect, the average weight of a fluconazole tablet can be about 0.405 grams and can comprise about 200 mg of fluconazole. In an aspect, using the above-identified formula, the amount of powder from crushed fluconazole tablets can be determined to be about 0.050625 g (or 50.625 mg).

$$\text{average tablet weight} \times \text{\% of a tablet needed} =$$
$$(0.405 \text{ g}) \quad (12.5\%)$$
$$\text{amount of powder from crushed tablets needed}$$
$$(0.050625 \text{ g})$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, doxycycline or a salt thereof, and fluconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, doxycycline or a salt thereof, and fluconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, doxycycline or a pharmaceutically acceptable salt thereof, and fluconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 10

In an aspect, to make 1 g of the compounded composition, which has about 1.655% w/w mupirocin, about 5.0% w/w doxycycline or a pharmaceutically acceptable salt thereof, and about 2.5% w/w fluconazole, about 0.8276 g of mupirocin 2.0% cream or ointment, about 0.12175 g of powder from crushed doxycycline hyclate tablets, and about 0.050625 g of powder from crushed fluconazole tablets can be combined and mixed together according to a method described above.

Table 10 provides the approximate amount of mupirocin, doxycycline hyclate, and fluconazole needed to make various amounts of the compounded composition.

TABLE 10

MUPIROCIN, DOXYCYCLINE HYCLATE, AND FLUCONAZOLE

| Compounded Composition (in grams) | Mupirocin (2.0% cream or ointment) | Doxycycline Hyclate (powder from crushed tablets) | Fluconazole (powder from crushed tablets) |
| --- | --- | --- | --- |
| 1 | 0.8276 g | 0.12175 g | 0.050625 g |
| 4 | 3.3104 g | 0.487 g | 0.2025 g |
| 8 | 6.6208 g | 0.974 g | 0.405 g |
| 25 | 20.69 g | 3.04375 g | 1.26562 g |
| 50 | 41.38 g | 6.0875 g | 2.53125 g |
| 240 | 198.624 g | 29.22 g | 12.15 g |
| 1500 | 1241.4 g | 182.625 g | 75.9375 g |

As used in Example 10, the term "about" means a value falling within a range that is ±10% of the stated value. In an aspect, the skilled person can combine 0.8276 g±10% mupirocin 2.0 ointment (e.g., from about 0.74484 g-0.91036 g), 0.12175 g±10% powder from crushed doxycycline hyclate tablets (e.g., from about 0.109575 g-0.133925 g), and 0.050625 g±10% powder from crushed fluconazole tablets (e.g., from about 0.0455625 g-0.0556875 g) and mix together according to a method described above to make about 1.0 g±10% of the compounded composition.

Mupirocin, Doxycycline or a Salt Thereof, and Ketoconazole

Disclosed herein is a method of making a compounded composition, the method comprising: mixing a therapeutically effective amount of mupirocin, a therapeutically effective amount of a doxycycline or a pharmaceutically acceptable salt thereof, and a therapeutically effective amount of a ketoconazole to make a homogeneous compounded composition. A disclosed compounded composition can comprise a dry powder formulation or can comprise a cream or ointment.

In an aspect, a disclosed method can comprise obtaining the mupirocin, obtaining the doxycycline or a pharmaceutically acceptable salt thereof, obtaining the ketoconazole, or a combination thereof. In an aspect, obtaining can comprise obtaining a bulk source of the mupirocin, obtaining a bulk source of the doxycycline or a pharmaceutically acceptable salt thereof, obtaining a bulk source of the ketoconazole, or a combination thereof.

In an aspect, a disclosed compounded composition comprising mupirocin, doxycycline or a salt thereof, and ketoconazole can comprise from about 1.0% w/w to about 3.0% w/w mupirocin. In an aspect, a disclosed compounded composition comprising mupirocin, doxycycline or a salt thereof, and ketoconazole can comprise about 1.6% w/w or about 1.8% w/w mupirocin. In an aspect, a disclosed compounded composition comprising mupirocin, doxycycline or a salt thereof, and ketoconazole can comprise from about 1.5% to about 3.5% w/w or from about 4.0% to about 6.0% w/w doxycycline or a pharmaceutically acceptable salt thereof. In an aspect, a disclosed compounded composition comprising mupirocin, doxycycline or a salt thereof, and ketoconazole can comprise about 2.5% w/w or 5.0% w/w doxycycline or a pharmaceutically acceptable salt thereof. In an aspect, a disclosed compounded composition comprising mupirocin, doxycycline or a salt thereof, and ketoconazole can comprise from about 1.5% w/w to about 3.5% w/w or from about 4.0% to about 6.0% w/w ketoconazole. In an aspect, a disclosed compounded composition comprising mupirocin, doxycycline or a salt thereof, and ketoconazole can comprise about 2.5% w/w or about 5.0% w/w ketoconazole.

In an aspect, a disclosed compounded composition comprising mupirocin, doxycycline or a salt thereof, and ketoconazole can comprise about 1.6% w/w mupirocin, about 5.0% w/w doxycycline or a pharmaceutically acceptable salt thereof, and about 5.0% w/w ketoconazole.

In an aspect, a disclosed compounded composition comprising mupirocin, doxycycline or a salt thereof, and ketoconazole can comprise about 1.8% w/w mupirocin, about 2.5% w/w doxycycline or a pharmaceutically acceptable salt thereof, and about 2.5% w/w ketoconazole.

In an aspect, the formula presented below can be used to identify the approximate amount of powder from crushed doxycycline hyclate tablets needed for 1 g of the compounded composition: avg. tablet weight (g)×% of a tablet needed=amt. of powder from crushed tablets needed (g)

In an aspect, the average weight of a doxycycline hyclate tablet can be about 0.2435 grams and can comprise about 100 mg of doxycycline. In an aspect, using the above-identified formula, the amount of powder from crushed doxycycline hyclate tablets needed for 1 g of the compounded composition can be determined to be about 0.060875 g (or 60.875 mg).

$$\underset{(0.2435\ \text{g})}{\text{average tablet weight}} \times \underset{(25.0\%)}{\text{\% of a tablet needed}} = \underset{(0.060875\ \text{g})}{\text{amount of powder from crushed tablets needed}}$$

In an aspect, using the above-identified formula, the amount of powder from crushed doxycycline hyclate tablets needed for 1 g of the compounded composition can be determined to be about 0.12175 g (or 121.75 mg).

$$\frac{\text{average tablet weight}}{(0.2435 \text{ g})} \times \frac{\% \text{ of a tablet needed}}{(50.0\%)} = \frac{\text{amount of powder from crushed tablets needed}}{(0.12175 \text{ g})}$$

In an aspect, the formula presented below can be used to identify the approximate amount of powder from crushed ketoconazole tablets needed for 1 g of the compounded composition:

avg. tablet weight (g)×% of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets needed for 1 g of the compounded composition can be determined to be about 0.0775 g (or 77.5 mg).

$$\frac{\text{avg. tablet weight (g)}}{(0.3100 \text{ g})} \times \frac{\% \text{ of a tablet needed}}{(25.0\%)} = \frac{\text{amt. of powder from crushed tablets needed (g)}}{(0.0775 \text{ g})}$$

In an aspect, using the above-identified formula, the amount of powder from crushed ketoconazole tablets needed for 1 g of the compounded composition can be determined to be about 0.03875 g (or 38.75 mg).

$$\frac{\text{avg. tablet weight (g)}}{(0.3100 \text{ g})} \times \frac{\% \text{ of a tablet needed}}{(12.5\%)} = \frac{\text{amt. of powder from crushed tablets needed (g)}}{(0.03875 \text{ g})}$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, doxycycline or a salt thereof, and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, doxycycline or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, doxycycline or a pharmaceutically acceptable salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 11

In an aspect, to make 1 g of the compounded composition, which has about 1.6% w/w mupirocin, about 5.0% w/w doxycycline or a pharmaceutically acceptable salt thereof, and about 5.0% w/w ketoconazole, about 0.8008 g of mupirocin 2.0% cream or ointment, about 0.12175 g of powder from crushed doxycycline hyclate tablets, and about 0.0775 g of powder from crushed ketoconazole tablets can be combined and mixed together according to a disclosed method described above.

Table 11 provides the approximate amount of mupirocin, doxycycline hyclate, and ketoconazole needed to make various amounts of the compounded composition.

TABLE 11

MUPIROCIN, DOXYCYCLINE HYCLATE, AND KETOCONAZOLE

| Compounded Composition (in grams) | Mupirocin (2.0% cream or ointment) | Doxycycline Hyclate (powder from crushed tablets) | Ketoconazole (powder from crushed tablets) |
|---|---|---|---|
| 1 | 0.8008 g | 0.12175 g | 0.0775 g |
| 4 | 3.2032 g | 0.487 g | 0.31 g |
| 8 | 6.4064 g | 0.974 g | 0.62 g |
| 25 | 20.02 g | 3.04375 g | 1.9375 g |
| 50 | 40.04 g | 6.0875 g | 3.875 g |
| 240 | 192.192 g | 29.22 g | 18.6 g |
| 1500 | 1201.2 g | 182.625 g | 116.25 g |

As used in Example 11, the term "about" means a value falling within a range that is ±10% of the stated value. In an aspect, the skilled person can combine 0.8008 g±10% mupirocin 2.0% cream or ointment (e.g., from about 0.72072 g-0.88088 g), 0.12175 g±10% powder from crushed doxycycline hyclate tablets (e.g., from about 0.109575 g-0.133925 g), and 0.0775 g±10% powder from crushed ketoconazole tablets (e.g., from about 0.06975 g-0.08525 g)

and mix together according to a method described above to make about 1.0 g±10% of the compounded composition.

Example 12

In an aspect, to make 1 g of the compounded composition, which has about 1.8% w/w mupirocin, about 2.5% w/w doxycycline or a pharmaceutically acceptable salt thereof, and about 2.5% w/w ketoconazole, about 0.9004 g of mupirocin 2.0% cream or ointment, about 0.060875 g of powder from crushed doxycycline hyclate tablets, and about 0.03875 g of powder from crushed ketoconazole tablets can be combined and mixed together according to a disclosed method described above.

Table 12 provides the approximate amount of mupirocin, doxycycline hyclate, and ketoconazole needed to make various amounts of the compounded composition.

TABLE 12

MUPIROCIN, DOXYCYCLINE HYCLATE, AND KETOCONAZOLE

| Compounded Composition (in grams) | Mupirocin (2.0% cream or ointment) | Doxycycline Hyclate (powder from crushed tablets) | Ketoconazole (powder from crushed tablets) |
|---|---|---|---|
| 1 | 0.9004 g | 0.060875 g | 0.03875 g |
| 4 | 3.6016 g | 0.2435 g | 0.155 g |
| 8 | 7.2032 g | 0.487 g | 0.31 g |
| 25 | 22.51 g | 1.521875 g | 0.96875 g |
| 50 | 45.02 g | 3.04375 g | 1.9375 g |
| 240 | 216.096 g | 14.61 g | 9.3 g |
| 1500 | 1350.6 g | 91.3125 g | 58.125 g |

As used in Example 12, the term "about" means a value falling within a range that is ±10% of the stated value. In an aspect, the skilled person can combine 0.9004 g±10% mupirocin 2.0% cream or ointment (e.g., from about 0.81036 g-0.99044 g), 0.060875 g±10% powder from crushed doxycycline hyclate tablets (e.g., from about 0.0547875 g-0.0669625 g), and 0.03875 g±10% powder from crushed ketoconazole tablets (e.g., from about 0.034875 g-0.042625 g) and mix together according to a method described above to make about 1.0 g±10% of the compounded composition.

Mupirocin, Tobramycin or a Salt Thereof, and Ketoconazole

Disclosed herein is a method of making a compounded composition, the method comprising: mixing a therapeutically effective amount of mupirocin, a therapeutically effective amount of tobramycin or a pharmaceutically acceptable salt thereof, and a therapeutically effective amount of ketoconazole to make a homogeneous compounded composition. A disclosed compounded composition can comprise a dry powder formulation or can comprise a cream or ointment.

In an aspect, a disclosed method can comprise obtaining the mupirocin, obtaining the tobramycin or a pharmaceutically acceptable salt thereof, obtaining the ketoconazole, or a combination thereof. In an aspect, obtaining can comprise obtaining a bulk source of the mupirocin, obtaining a bulk source of the tobramycin or a pharmaceutically acceptable salt thereof, obtaining a bulk source of ketoconazole, or a combination thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, the average weight of a ketoconazole tablet can be about 0.310 grams and can comprise about 200 mg of ketoconazole. In an aspect, the formula presented below can be used to identify the approximate amount of powder from crushed commercially available ketoconazole tablets needed for 1 g of the compounded composition:

$$\text{avg. tablet weight (g)} \times \frac{\% \text{ of a tablet needed}}{(25.0\%)} = $$
$$(0.3100 \text{ g})$$
$$\text{amt. of powder from crushed tablets needed (g)}$$
$$(0.0775 \text{ g})$$

In an aspect, a disclosed compounded composition comprising mupirocin, tobramycin or a salt thereof, and ketoconazole can comprise from about 1.4% w/w to about 2.0% w/w, from about 1.5% w/w to about 1.9% w/w, or from about 1.6% w/w to about 1.8% w/w mupirocin. In an aspect, a disclosed compounded composition comprising mupirocin, tobramycin or a salt thereof, and ketoconazole can comprise about 1.695% w/w or about 1.8475% w/w mupirocin. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w tobramycin or a pharmaceutically acceptable salt thereof. In an aspect, a disclosed compounded composition comprising mupirocin, tobramycin or a salt thereof, and ketoconazole can comprise about 2.5% w/w or about 5.0% w/w tobramycin or a pharmaceutically acceptable salt thereof. In an aspect, a disclosed compounded composition comprising mupirocin, tobramycin or a salt thereof, and ketoconazole can comprise from about 1.0% w/w to about 7.0% w/w or from about 2.0% w/w to about 6.0% w/w ketoconazole. In an aspect, a disclosed compounded composition comprising mupirocin, tobramycin or a salt thereof, and ketoconazole can comprise about 2.5% w/w or 5.0% w/w ketoconazole.

In an aspect, a disclosed compounded composition comprising mupirocin, tobramycin or a salt thereof, and ketoconazole can comprise from about 1.695% w/w mupirocin, about 5.0% w/w tobramycin or a pharmaceutically acceptable salt thereof, and about 5.0% w/w ketoconazole.

In an aspect, a disclosed compounded composition comprising mupirocin, tobramycin or a salt thereof, and ketoconazole can comprise from about 1.8475% w/w mupirocin, about 2.5% w/w tobramycin or a pharmaceutically acceptable salt thereof, and about 2.5% w/w ketoconazole.

In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise from about 1.7% w/w to about 1.8% w/w mupirocin, about 5.0% w/w tobramycin or a pharmaceutically acceptable salt thereof, and about 2.5% w/w ketoconazole. In an aspect, a disclosed compounded composition comprising mupirocin, tobramycin or a salt thereof, and ketoconazole can comprise about 1.749% w/w mupirocin, about 5.0% w/w tobramycin or a pharmaceutically acceptable salt thereof, and about 2.5% w/w ketoconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, tobramycin or a salt thereof, and ketoconazole into a container and sealing the container. In an aspect, a container can be a container disclosed herein, such as, for example, a syringe. In an aspect, a disclosed method can comprise sterilizing the compounded composition comprising mupirocin, tobramycin or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, tobramycin or a pharmaceutically acceptable salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 13

In an aspect, to make 1 g of the compounded composition, which has about 1.8475% w/w mupirocin, about 2.5% w/w tobramycin or a pharmaceutically acceptable salt thereof, and about 2.5% w/w ketoconazole, about 0.92375 g of mupirocin 2.0% cream or ointment, about 0.0375 g of tobramycin sulfate for injection USP powder, and about 0.03875 g of powder from crushed ketoconazole tablets.

Table 13 provides the approximate amount of mupirocin, tobramycin sulfate, and ketoconazole needed to make various amounts of the compounded composition.

TABLE 13

MUPIROCIN, TOBRAMYCIN SULFATE, AND KETOCONAZOLE

| Compounded Composition (in grams) | Mupirocin (2.0% cream or ointment) | Tobramycin Sulfate (USP powder for injection) | Ketoconazole (powder from crushed tablets) |
| --- | --- | --- | --- |
| 1 | 0.92375 g | 0.0375 g | 0.03875 g |
| 4 | 3.695 g | 0.15 g | 0.155 g |
| 8 | 7.39 g | 0.30 g | 0.31 g |
| 25 | 23.09375 g | 0.9375 g | 0.96875 g |
| 50 | 46.1875 g | 1.875 g | 1.9375 g |
| 240 | 221.7 g | 9.0 g | 9.3 g |
| 1500 | 1385.625 g | 56.25 g | 58.125 g |

As used in Example 13, the term "about" means a value falling within a range that is ±10% of the stated value. In an aspect, the skilled person can combine 0.92375 g±10% mupirocin 2.0% cream or ointment (e.g., from about 0.8313 g-1.0161 g), 0.0375 g±10% tobramycin sulfate USP powder for injection (e.g., from about 0.03375 g-0.04125 g), and 0.03875 g±10% powder from crushed ketoconazole tablets (e.g., from about 0.03487 g-0.04262 g) and mix together according to a method described above to make about 1.0 g±10% of the compounded composition.

Example 14

In an aspect, to make about 1 g of the compounded composition, which has about 1.695% w/w mupirocin, about 5.0% w/w tobramycin or a pharmaceutically acceptable salt thereof, and about 5.0% w/w ketoconazole, about 0.8475 g of mupirocin 2.0% cream or ointment, about 0.075 g of tobramycin sulfate for injection USP powder, and about 0.0775 g of powder from crushed ketoconazole tablets.

Table 14 provides the approximate amount of mupirocin, tobramycin sulfate, and ketoconazole needed to make various amounts of the compounded composition.

TABLE 14

MUPIROCIN, TOBRAMYCIN SULFATE, AND KETOCONAZOLE

| Compounded Composition (in grams) | Mupirocin (2.0% cream or ointment) | Tobramycin Sulfate (USP powder for injection) | Ketoconazole (powder from crushed tablets) |
| --- | --- | --- | --- |
| 1 | 0.8475 g | 0.075 g | 0.0775 g |
| 4 | 3.39 g | 0.30 g | 0.31 g |
| 8 | 6.78 g | 0.60 g | 0.62 g |
| 25 | 21.1875 g | 1.875 g | 1.9375 g |
| 50 | 42.375 g | 3.75 g | 3.875 g |
| 240 | 203.4 g | 18.0 g | 18.6 g |
| 1500 | 1271.25 g | 112.5 g | 116.25 g |

As used in Example 14, the term "about" means a value falling within a range that is ±10% of the stated value. In an aspect, the skilled person can combine 0.8475 g±10% mupirocin 2.0% cream or ointment (e.g., from about 0.7627 g-0.9322 g), 0.075 g±10% tobramycin sulfate USP powder for injection (e.g., from about 0.0675 g-0.0825 g), and 0.0775 g±10% powder from crushed ketoconazole tablets (e.g., from about 0.06975 g-0.08525 g) and mix together according to a method described above to make about 1.0 g±10% of the compounded composition.

Mupirocin, Tobramycin or a Salt Thereof, and Fluconazole

Disclosed herein is a method of making a compounded composition, the method comprising: mixing a therapeutically effective amount of mupirocin, a therapeutically effective amount of tobramycin or a pharmaceutically acceptable salt thereof, and a therapeutically effective amount of fluconazole to make a homogeneous compounded composition. A disclosed compounded composition can comprise a dry powder formulation or can comprise a cream or ointment.

In an aspect, a disclosed method can comprise obtaining the mupirocin, obtaining the tobramycin or a pharmaceutically acceptable salt thereof, obtaining the fluconazole, or a combination thereof. In an aspect, obtaining can comprise obtaining a bulk source of the mupirocin, obtaining a bulk source of the tobramycin or a pharmaceutically acceptable salt thereof, obtaining a bulk source of fluconazole, or a combination thereof.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, the formula presented below can be used to identify the approximate amount of powder from crushed fluconazole tablets needed for 1 g of the compounded composition:

average tablet weight×% of a tablet needed=amount of powder from crushed tablets needed (g)

In an aspect, the average weight of a fluconazole tablet can be about 0.405 grams and can comprise about 200 mg of fluconazole. In an aspect, using the above-identified formula, the amount of powder from crushed fluconazole tablets can be determined.

$$\text{average tablet weight (g)} \times \text{\% of a tablet needed} = \text{amount of powder from crushed tablets needed}$$
$$(0.405 \text{ g}) \times (12.5\%) = (0.050625 \text{ g})$$

In an aspect, a disclosed compounded composition comprising mupirocin, tobramycin or a salt thereof, and fluconazole can comprise about 1.8% w/w mupirocin, about 2.5% w/w tobramycin or a pharmaceutically acceptable salt thereof, and about 2.5% w/w fluconazole. In an aspect, a disclosed compounded composition comprising mupirocin, tobramycin or a salt thereof, and fluconazole can comprise about 1.8475% w/w mupirocin, about 2.5% w/w tobramycin or a pharmaceutically acceptable salt thereof, and about 2.5% w/w fluconazole.

In an aspect, a disclosed compounded composition comprising mupirocin, tobramycin or a salt thereof, and fluconazole can comprise about 1.7% w/w mupirocin, about 5.0% w/w tobramycin or a pharmaceutically acceptable salt thereof, and about 5.0% w/w fluconazole. In an aspect, a disclosed compounded composition comprising mupirocin, tobramycin or a salt thereof, and fluconazole can comprise about 1.695% w/w mupirocin, about 5.0% w/w tobramycin or a pharmaceutically acceptable salt thereof, and about 5.0% w/w fluconazole.

In an aspect, a disclosed compounded composition comprising mupirocin, tobramycin or a salt thereof, and fluconazole can comprise from about 1.7% w/w to about 1.8% w/w mupirocin, about 5.0% w/w tobramycin or a pharmaceutically acceptable salt thereof, and about 2.5% w/w fluconazole. In an aspect, a disclosed compounded composition comprising mupirocin, tobramycin or a salt thereof, and fluconazole can comprise about 1.749% w/w mupirocin, about 5.0% w/w tobramycin or a pharmaceutically acceptable salt thereof, and about 2.5% w/w fluconazole.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, tobramycin or a salt thereof, and fluconazole into a container and sealing the container. In an aspect, a container can be a container disclosed herein, such as, for example, a syringe. In an aspect, a disclosed method can comprise sterilizing the compounded composition comprising mupirocin, tobramycin or a salt thereof, and fluconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. In an aspect, to make the compounded composition, mupirocin, tobramycin or a pharmaceutically acceptable salt thereof, and fluconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 15

In an aspect, to make 1 g of the compounded composition, which has about 1.749% w/w mupirocin, about 5.0% w/w tobramycin or a pharmaceutically acceptable salt thereof, and about 2.5% w/w fluconazole, about 0.8744 g of mupirocin 2.0% cream or ointment, about 0.075 g of tobramycin sulfate for injection USP powder, and about 0.050625 g of powder from crushed fluconazole tablets can be combined and mixed together according to a disclosed method described above.

Table 15 provides the approximate amount of mupirocin, tobramycin sulfate, and fluconazole needed to make various amounts of the compounded composition.

TABLE 15

MUPIROCIN, TOBRAMYCIN SULFATE, AND FLUCONAZOLE

| Compounded Composition (in grams) | Mupirocin (2.0% cream or ointment) | Tobramycin Sulfate (USP powder for injection) | Fluconazole (powder from crushed tablets) |
|---|---|---|---|
| 1 | 0.8744 g | 0.075 g | 0.050625 g |
| 4 | 3.4976 g | 0.3 g | 0.2025 g |

TABLE 15-continued

MUPIROCIN, TOBRAMYCIN SULFATE, AND FLUCONAZOLE

| Compounded Composition (in grams) | Mupirocin (2.0% cream or ointment) | Tobramycin Sulfate (USP powder for injection) | Fluconazole (powder from crushed tablets) |
|---|---|---|---|
| 8 | 6.9952 g | 0.6 g | 0.405 g |
| 25 | 21.86 g | 1.875 g | 1.265625 g |
| 50 | 43.72 g | 3.75 g | 2.53125 g |
| 240 | 209.856 g | 18.0 g | 12.15 g |
| 1500 | 1311.6 g | 112.5 g | 75.9375 g |

As used in Example 15, the term "about" means a value falling within a range that is ±10% of the stated value. In an aspect, the skilled person can combine 0.8744 g±10% mupirocin 2.0% cream or ointment (e.g., from about 0.78696 g-0.96184 g), 0.075 g±10% tobramycin sulfate USP powder for injection (e.g., from about 0.0675 g-0.0825 g), and 0.050625 g±10% powder from crushed fluconazole tablets (e.g., from about 0.0455625 g-0.0556875 g) and mix together according to a method described above to make about 1.0 g 10% of the compounded composition.

Example 16

In an aspect, to make 1 g of the compounded composition, which has about 1.8% w/w mupirocin, about 2.5% w/w tobramycin or a pharmaceutically acceptable salt thereof, and about 2.5% w/w fluconazole, about 0.92375 g of mupirocin 2.0% cream or ointment, about 0.0375 g of tobramycin sulfate for injection USP powder, and about 0.03875 g of powder from crushed fluconazole tablets.

Table 16 provides the approximate amount of mupirocin, tobramycin sulfate, and fluconazole needed to make various amounts of the compounded composition.

TABLE 16

MUPIROCIN, TOBRAMYCIN SULFATE, AND FLUCONAZOLE

| Compounded Composition (in grams) | Mupirocin (2.0% cream or ointment) | Tobramycin Sulfate (USP powder for injection) | Fluconazole (powder from crushed tablets) |
|---|---|---|---|
| 1 | 0.92375 g | 0.0375 g | 0.03875 g |
| 4 | 3.695 g | 0.15 g | 0.155 g |
| 8 | 7.39 g | 0.30 g | 0.31 g |
| 25 | 23.09375 g | 0.9375 g | 0.96875 g |
| 50 | 46.1875 g | 1.875 g | 1.9375 g |
| 240 | 221.7 g | 9.0 g | 9.3 g |
| 1500 | 1385.625 g | 56.25 g | 58.125 g |

As used in Example 16, the term "about" means a value falling within a range that is ±10% of the stated value. In an aspect, the skilled person can combine 0.92375 g±10% mupirocin 2.0% cream or ointment (e.g., from about 0.83137 g-1.01612 g), 0.0375 g±10% tobramycin sulfate powder for injection (e.g., from about 0.03375 g-0.04125 g), and 0.03875 g±10% powder from crushed fluconazole tablets (e.g., from about 0.03487 g-0.042625 g) and mix together according to a method described above to make about 1.0 g±10% of the compounded composition.

Example 17

In an aspect, to make about 1 g of the compounded composition, which has about 1.7% w/w mupirocin, about 5.0% w/w tobramycin or a pharmaceutically acceptable salt thereof, and about 5.0% w/w fluconazole, about 0.8475 g of mupirocin 2.0% cream or ointment, about 0.075 g of tobramycin sulfate for injection USP powder, and about 0.0775 g of powder from crushed fluconazole tablets.

Table 17 provides the approximate amount of mupirocin, tobramycin sulfate, and fluconazole needed to make various amounts of the compounded composition.

TABLE 17

MUPIROCIN, TOBRAMYCIN SULFATE, AND FLUCONAZOLE

| Compounded Composition (in grams) | Mupirocin (2.0% cream or ointment) | Tobramycin Sulfate (USP powder for injection) | Fluconazole (powder from crushed tablets) |
|---|---|---|---|
| 1 | 0.8475 g | 0.075 g | 0.0775 g |
| 4 | 3.39 g | 0.30 g | 0.31 g |
| 8 | 6.78 g | 0.60 g | 0.62 g |
| 25 | 21.1875 g | 1.875 g | 1.9375 g |
| 50 | 42.375 g | 3.75 g | 3.875 g |
| 240 | 203.4 g | 18.0 g | 18.6 g |
| 1500 | 1271.25 g | 112.5 g | 116.25 g |

As used in Example 17, the term "about" means a value falling within a range that is ±10% of the stated value. In an aspect, the skilled person can combine 0.8475 g±10% mupirocin 2.0% cream or ointment (e.g., from about 0.76275 g-0.9322 g), 0.075 g±10% powder from tobramycin sulfate powder for injection (e.g., from about 0.0675 g-0.0825 g), and 0.0775 g±10% powder from crushed fluconazole tablets (e.g., from about 0.06975 g-0.08525 g) and mix together according to a method described above to make about 1.0 g±10% of the compounded composition.

Mupirocin, an Azole, and a Fluoroquinolone

Disclosed herein is a method of making a compounded composition, the method comprising: mixing a therapeutically effective amount of mupirocin, a therapeutically effective amount of a fluoroquinolone, and a therapeutically effective amount of an azole to make a homogeneous compounded composition.

In an aspect, a disclosed method can comprise obtaining the mupirocin, obtaining the fluoroquinolone, obtaining the azole, or a combination thereof. In an aspect, obtaining can comprise obtaining a bulk source of the mupirocin, obtaining a bulk source of the fluoroquinolone, obtaining a bulk source of the azole, or a combination thereof.

In an aspect, a disclosed compounded composition comprising mupirocin, a fluoroquinolone, and an azole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, a fluoroquinolone, and an azole can comprise about 1.8453% w/w mupirocin.

In an aspect, a disclosed compounded composition comprising mupirocin, a fluoroquinolone, and an azole can comprise from about 1.0% w/w to about 6.0% w/w, from about 1.5% w/w to about 5.0% w/w, from about 2.5% w/w to about 5.0% w/w, from about 2.0% w/w to about 4%, from about 2.0% w/w to about 4.0% w/w, or from about 2.5% w/w to about 3.0% w/w of the fluoroquinolone. In an aspect, a disclosed compounded composition comprising mupirocin, a fluoroquinolone, and an azole can comprise about 2.5% w/w of the fluoroquinolone.

In an aspect, a disclosed compounded composition comprising mupirocin, a fluoroquinolone, and an azole can comprise from about 1.0% w/w to about 6.0% w/w, about 1.5% w/w to about 5.0% w/w, from about 2.5% w/w to about 5.0% w/w, from about 2.0% w/w to about 4.0% w/w, from about 2.0% w/w to about 4.0% w/w, from about 2.5% w/w to about 3.0% w/w of the azole. In an aspect, a disclosed compounded composition comprising mupirocin, a fluoroquinolone, and an azole can comprise about 2.5% w/w of the azole.

In an aspect, a disclosed compounded composition comprising mupirocin, a fluoroquinolone, and an azole can comprise about the same amount of an azole and a fluoroquinolone. In an aspect, a disclosed compounded composition comprising mupirocin, a fluoroquinolone, and an azole can comprise about 1.8453% w/w mupirocin, about 2.5% w/w of the fluoroquinolone, and about 2.5% w/w of the azole. In an aspect, a disclosed compounded composition comprising mupirocin, a fluoroquinolone, and an azole can comprise about 1.768% w/w mupirocin, about 5.0% w/w of the fluoroquinolone, and about 2.5% w/w of the azole.

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, a fluoroquinolone, and an azole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, a fluoroquinolone, and an azole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, the fluoroquinolone, and the azole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Mupirocin, Ciprofloxacin or a Salt Thereof, and Ketoconazole

Disclosed herein is a method of making a compounded composition, the method comprising: mixing a therapeutically effective amount of mupirocin, a therapeutically effective amount of ciprofloxacin or a pharmaceutically acceptable salt thereof, and a therapeutically effective amount of ketoconazole to make a homogeneous compounded composition.

In an aspect, a disclosed method can comprise obtaining mupirocin, obtaining ciprofloxacin or a pharmaceutically acceptable salt thereof, obtaining ketoconazole, or a combination thereof. In an aspect, obtaining can comprise obtaining a bulk source of mupirocin, obtaining a bulk source of ciprofloxacin or a pharmaceutically acceptable salt thereof, obtaining a bulk source of ketoconazole, or a combination thereof.

In an aspect, a disclosed compounded composition comprising mupirocin, ciprofloxacin or a salt thereof, and ketoconazole can comprise from about 1.0% w/w to about 3.0% w/w, from about 1.5% w/w to about 2.5% w/w, from about 1.0% w/w to about 2.0% w/w, from about 1.5% w/w to about 2.0% w/w, or from about 2.0% w/w to about 2.5% w/w mupirocin. In an aspect, a disclosed compounded composition comprising mupirocin, ciprofloxacin or a salt thereof, and ketoconazole can comprise about 1.768% w/w or 1.8453% w/w mupirocin. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ciprofloxacin or a pharmaceutically acceptable salt thereof. In an aspect, a disclosed compounded composition comprising mupirocin, ciprofloxacin or a salt thereof, and ketoconazole can comprise about 2.5% w/w or about 5.0% w/w ciprofloxacin or a pharmaceutically acceptable salt thereof. In an aspect, a disclosed compounded composition comprising mupirocin, ciprofloxacin or a salt thereof, and ketoconazole can comprise from about 1.0% w/w to about 6.0% w/w, from about 1.5% w/w to about 5.0% w/w, from about 2.5% w/w to about 5.0% w/w, from about 2.0% w/w to about 4.0% w/w, from about 2.0% w/w to about 4.0% w/w, or from about 2.5% w/w to about 3.0% w/w ketoconazole. In an aspect, a disclosed compounded composition comprising mupirocin, ciprofloxacin or a salt thereof, and ketoconazole can comprise about 2.5% w/w or about 5.0% w/w ketoconazole.

In an aspect, a disclosed compounded composition can comprise about 1.8453% w/w mupirocin, about 2.5% w/w ciprofloxacin or a pharmaceutically acceptable salt thereof, and about 2.5% w/w ketoconazole.

In an aspect, a disclosed compounded composition can comprise from about 1.768% w/w mupirocin, about 5.0% w/w ciprofloxacin or a pharmaceutically acceptable salt thereof, and about 2.5% w/w ketoconazole.

In an aspect, the formula presented below can be used to identify the approximate amount of powder from crushed commercially available ciprofloxacin tablets needed for 1 g of the compounded composition: avg. tablet weight (g)×% of a tablet needed=amt. of powder from crushed tablets needed (g)

In an aspect, the average weight of a ciprofloxacin tablet can be about 1.158 grams and can comprise about 750 mg of ciprofloxacin.

$$\text{average tablet weight (g)} \times \frac{\% \text{ of a tablet needed}}{(6.67\%)} =$$
$$(1.158 \text{ g})$$
amount of powder from crushed tablets needed (0.07723 g)

$$\text{average tablet weight (g)} \times \frac{\% \text{ of a tablet needed}}{(3.33\%)} =$$
$$(1.158 \text{ g})$$
amount of powder from crushed tablets needed (0.03856 g)

In an aspect, the formula presented below can be used to identify the approximate amount of powder from crushed commercially available ketoconazole tablets needed for 1 g of the compounded composition: avg. tablet weight (g)×% of a tablet needed=amt. of powder from crushed tablets needed (g)

In an aspect, the average weight of a ketoconazole tablet can be about 0.310 grams and can comprise about 200 mg of ketoconazole.

$$\text{avg. tablet weight (g)} \times \frac{\% \text{ of a tablet needed}}{(12.5\%)} =$$
$$(0.3100 \text{ g})$$
amt. of powder from crushed tablets needed (g) (0.03875 g)

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, ciprofloxacin or a salt thereof, and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, ciprofloxacin or a salt thereof, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, ciprofloxacin or a salt thereof, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 18

In an aspect, to make 1 g of the compounded composition, which has about 1.8453% w/w mupirocin, about 2.5% w/w ciprofloxacin or a pharmaceutically acceptable salt thereof, and about 2.5% w/w ketoconazole, about 0.9227 g of mupirocin 2.0% cream or ointment, about 0.03856 g of powder from crushed ciprofloxacin tablets, about 0.03875 mg of powder from crushed ketoconazole tablets can be combined and mixed together according to a disclosed method described above.

Table 18 provides the approximate amount of mupirocin, ciprofloxacin, and ketoconazole needed to make various amounts of the compounded composition.

TABLE 18

MUPIROCIN, CIPROFLOXACIN OR A SALT THEREOF, AND KETOCONAZOLE

| Compounded Composition (in grams) | Mupirocin (2.0% cream or ointment) | Ciprofloxacin (powder from crushed tablets) | Ketoconazole (powder from crushed tablets) |
| --- | --- | --- | --- |
| 1 | 0.9227 g | 0.03856 g | 0.03875 g |
| 4 | 3.6908 g | 0.15424 g | 0.155 g |
| 8 | 7.3816 g | 0.30848 g | 0.310 g |
| 25 | 23.0675 g | 0.964 g | 0.96875 g |
| 50 | 46.135 g | 1.928 g | 1.9375 g |
| 240 | 221.448 g | 9.2544 g | 9.3 g |
| 1500 | 1384.05 g | 57.84 g | 58.125 g |

As used in Example 18, the term "about" means a value falling within a range that is ±10% of the stated value. In an aspect, the skilled person can combine 0.9227 g±10% mupirocin 2.0% cream or ointment (e.g., from about 0.83043 g-1.01497 g), 0.03856 g±10% powder from crushed ciprofloxacin tablets (e.g., from about 0.034704 g-0.042416 g), and 0.03875 g±10% powder from crushed ketoconazole tablets (e.g., from about 0.034875 g-0.042625 g) and mix together according to a method described above to make about 1.0 g±10% of the compounded composition.

Example 19

In an aspect, to make 1 g of the compounded composition, which has about 1.768% w/w mupirocin, about 5.0% w/w ciprofloxacin or a pharmaceutically acceptable salt thereof, and about 2.5% w/w ketoconazole, 0.8841 g of mupirocin 2% cream or ointment, about 0.07723 g of powder from crushed ciprofloxacin tablets, and about 0.03875 g of powder from crushed ketoconazole tablets (about 12.5% of a crushed 200 mg ketoconazole tablet) can be combined and mixed together according to a disclosed method described above.

Table 19 provides the approximate amount of mupirocin, ciprofloxacin, and ketoconazole powder needed to make various amounts of the compounded composition.

TABLE 19

MUPIROCIN, CIPROFLOXACIN OR A
SALT THEREOF, AND KETOCONAZOLE

| Compounded Composition (in grams) | Mupirocin (2.0% cream or ointment) | Ciprofloxacin (powder from crushed tablets) | Ketoconazole (powder from crushed tablets) |
|---|---|---|---|
| 1 | 0.8841 g | 0.07723 g | 0.03875 g |
| 4 | 3.5364 g | 0.30892 g | 0.155 g |
| 8 | 7.0728 g | 0.61784 g | 0.31 g |
| 25 | 22.1025 g | 1.93075 g | 0.96875 g |
| 50 | 44.205 g | 3.8615 g | 1.9375 g |
| 240 | 212.184 g | 18.5352 g | 9.3 g |
| 1500 | 1326.15 g | 115.845 g | 58.125 g |

As used in Example 19, the term "about" means a value falling within a range that is ±10% of the stated value. In an aspect, the skilled person can combine 0.8841 g±10% mupirocin 2.0% cream or ointment (e.g., from about 0.79569 g-0.97251 g), 0.07723 g±10% powder from crushed ciprofloxacin tablets (e.g., from about 0.069507 g-0.084953 g), and 0.03875 g±10% powder from crushed ketoconazole tablets (e.g., from about 0.034875 g-0.042625 g) and mix together according to a method described above to make about 1.0 g±10% of the compounded composition.

Mupirocin, Azithromycin, and Ketoconazole

Disclosed herein is a method of making a compounded composition, the method comprising: mixing a therapeutically effective amount of mupirocin, a therapeutically effective amount of azithromycin, and a therapeutically effective amount of a ketoconazole to make a homogeneous compounded composition. A disclosed compounded composition can comprise a dry powder formulation or can comprise a cream or ointment.

In an aspect, a disclosed method can comprise obtaining the mupirocin, obtaining the azithromycin, obtaining the ketoconazole, or a combination thereof. In an aspect, obtaining can comprise obtaining a bulk source of the mupirocin, obtaining a bulk source of the azithromycin, obtaining a bulk source of the ketoconazole, or a combination thereof.

In an aspect, a disclosed compounded composition comprising mupirocin, azithromycin, and ketoconazole can comprise from about 1.0% w/w to about 3.0% w/w mupirocin. In an aspect, a disclosed compounded composition comprising mupirocin, azithromycin, and ketoconazole can comprise about 1.645% w/w mupirocin. In an aspect, a disclosed compounded composition comprising mupirocin, azithromycin, and ketoconazole can comprise from about 4.0% to about 6.0% w/w azithromycin. In an aspect, a disclosed compounded composition comprising mupirocin, azithromycin, and ketoconazole can comprise about 5.0% w/w azithromycin. In an aspect a disclosed compounded composition comprising mupirocin, azithromycin, and ketoconazole can comprise from about 4.0% to about 6.0% w/w ketoconazole. In an aspect, a disclosed compounded composition comprising mupirocin, azithromycin, and ketoconazole can comprise about 5.0% w/w ketoconazole. In an a disclosed compounded composition comprising mupirocin, azithromycin, and ketoconazole can comprise about 1.645% w/w mupirocin, about 5.0% w/w azithromycin, and about 5.0% w/w ketoconazole.

In an aspect, the formula presented below can be used to identify the approximate amount of powder from crushed ketoconazole tablets needed for 1 g of the compounded composition:

avg. tablet weight (g)×% of a tablet needed=amt. of powder from crushed tablets needed (g)

In an aspect, the average weight of a ketoconazole tablet can be about 0.310 grams and can comprise about 200 mg of ketoconazole. In an aspect, using the above-identified formula, the amount of powder from crushed ketoconazole tablets needed for 1 g of the compounded composition can be determined to be about 0.0775 g (or 77.5 mg).

$$\underset{(0.3100 \text{ g})}{\text{avg. tablet weight (g)}} \times \underset{(25.0\%)}{\text{\% of a tablet needed}} = \underset{(0.0775 \text{ g})}{\text{amt. of powder from crushed tablets needed (g)}}$$

In an aspect, mupirocin can be added to a mixing container or extracted from a tube by attaching a key (e.g., a metal key) to an end of a tube of mupirocin and sliding the key down the length of the tube towards the aperture of the tube, thereby forcing the contents of the tube into the mixing container or out of the tube.

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition comprising mupirocin, azithromycin, and ketoconazole into a container and sealing the container. In an aspect, a container can be a container disclosed herein, such as, for example, a plastic tube, a glass or non-glass vial, a syringe, etc. In an aspect, a disclosed method can comprise sterilizing the compounded composition comprising mupirocin, azithromycin, and ketoconazole.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, azithromycin, and ketoconazole can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 20

In an aspect, to make 1 g of the compounded composition, which has about 1.645% w/w mupirocin, about 5.0% w/w azithromycin, and about 5.0% w/w ketoconazole, about 0.8225 g of mupirocin 2.0% cream or ointment, about 0.100 g of azithromycin for injection USP powder (500 mg azithromycin/1 g powder), and about 0.0775 g of powder from crushed ketoconazole tablets can be combined and mixed together according to a disclosed method described above.

Table 20 provides the approximate amount of mupirocin, azithromycin, and ketoconazole needed to make various amounts of the compounded composition.

TABLE 20

MUPIROCIN, AZITHROMYCIN, AND KETOCONAZOLE

| Compounded Composition (in grams) | Mupirocin (2.0% cream or ointment) | Azithromycin (500 mg/1 g powder for | Ketoconazole (powder from crushed tablets) |
|---|---|---|---|
| 1 | 0.8225 g | 0.100 g | 0.0775 g |
| 4 | 3.29 g | 0.400 g | 0.31 g |
| 8 | 6.58 g | 0.800 g | 0.62 g |
| 25 | 20.5625 g | 2.5 g | 1.9375 g |
| 50 | 41.125 g | 5.0 g | 3.875 g |
| 240 | 197.4 g | 24.0 g | 18.6 g |
| 1500 | 1233.75 g | 150.0 g | 116.25 g |

As used in Example 20, the term "about" means a value falling within a range that is ±10% of the stated value. In an aspect, the skilled person can combine 0.8225 g±10% mupirocin 2.0% cream or ointment (e.g., from about 0.74025 g-0.90475 g), 0.10 g±10% azithromycin powder (e.g., from about 0.09 g-0.11 g), and 0.0775 g±10% powder from crushed ketoconazole tablets (e.g., from about 0.06975 g-0.08525 g) and mix together according to a method described above to make about 1.0 g±10% of the compounded composition.

7. Miscellaneous

Mupirocin, Clindamycin or a Salt Thereof, Gentamicin or a Salt Thereof, and Econazole or a Salt Thereof Disclosed herein is method of making a compounded composition, the method comprising: mixing a therapeutically effective amount of mupirocin, a therapeutically effective of amount of clindamycin or a pharmaceutically acceptable salt thereof (e.g., phosphate), a therapeutically effective of amount of gentamicin or a pharmaceutically acceptable salt thereof (e.g., sulfate), and a therapeutically effective of amount of econazole or a pharmaceutically acceptable salt thereof (e.g., nitrate) to make a homogeneous compounded composition. A disclosed compounded composition can comprise a dry powder formulation or can comprise a cream or ointment.

In an aspect, a disclosed method can comprise obtaining mupirocin, obtaining the clindamycin or a pharmaceutically acceptable salt thereof (e.g., phosphate), obtaining the gentamicin or a pharmaceutically acceptable salt thereof (e.g., sulfate), obtaining the econazole or a pharmaceutically acceptable salt thereof (e.g., nitrate), or a combination thereof. In an aspect, obtaining can comprise obtaining a bulk source of the mupirocin, obtaining a bulk source of the clindamycin or a pharmaceutically acceptable salt thereof (e.g., phosphate), obtaining a bulk source of the gentamicin or a pharmaceutically acceptable salt thereof (e.g., sulfate), obtaining a bulk source of econazole or a pharmaceutically acceptable salt thereof (e.g., nitrate), or a combination thereof.

In an aspect, a disclosed compounded composition comprising mupirocin, clindamycin or a salt thereof, gentamicin or a salt thereof, and econazole or a salt thereof can comprise from about 0.5% w/w to about 1.4% w/w, from about 0.6% w/w to about 1.3% w/w, from about 0.7% w/w to about 1.2% w/w, from about 0.7% w/w to about 1.1% w/w, from about 0.8% w/w to about 1.0% w/w, or from about 0.9% w/w to about 1.0% w/w mupirocin.

In an aspect, a disclosed compounded composition comprising mupirocin, clindamycin or a salt thereof, gentamicin or a salt thereof, and econazole or a salt thereof can comprise from about 0.01% w/w to about 0.08% w/w or from about 0.04% w/w and about 0.06% w/w clindamycin or a pharmaceutically acceptable salt thereof (e.g., phosphate). In an aspect, a disclosed compounded composition comprising mupirocin, clindamycin or a salt thereof, gentamicin or a salt thereof, and econazole or a salt thereof can comprise about 0.01% w/w, about 0.02% w/w, about 0.03% w/w, about 0.06% w/w, or about 0.07% w/w clindamycin or a pharmaceutically acceptable salt thereof (e.g., phosphate).

In an aspect, a disclosed compounded composition comprising mupirocin, clindamycin or a salt thereof, gentamicin or a salt thereof, and econazole or a salt thereof can comprise from about 0.01% w/w to about 0.05% w/w, from about 0.01% w/w to about 0.04% w/w, from about 0.01% w/w to about 0.03% w/w, or from about 0.015% w/w to about 0.025% w/w gentamicin or a pharmaceutically acceptable salt thereof (e.g., sulfate).

In an aspect, a disclosed compounded composition comprising mupirocin, clindamycin or a salt thereof, gentamicin or a salt thereof, and econazole or a salt thereof can comprise from about 0.1% w/w to about 0.6% w/w, from about 0.2% w/w to about 0.5% w/w, from about 0.2% w/w to about 0.4% w/w, or from about 0.025% w/w to about 0.035% w/w econazole or a pharmaceutically acceptable salt thereof (e.g., nitrate).

In an aspect, a disclosed compounded composition comprising mupirocin, clindamycin or a salt thereof, gentamicin or a salt thereof, and econazole or a salt thereof can comprise from about 0.9% w/w to 1% w/w mupirocin, from about 0.04% w/w to about 0.06% w/w clindamycin or a pharmaceutically acceptable salt thereof (e.g., phosphate), from about 0.01% w/w to about 0.03% w/w gentamicin or a pharmaceutically acceptable salt thereof (e.g., sulfate), and from about 0.2% to about 0.4% w/w econazole or a pharmaceutically acceptable salt thereof (e.g., nitrate). In an aspect, a disclosed compounded composition can comprise about 0.9% w/w mupirocin, about 0.05% w/w clindamycin or a pharmaceutically acceptable salt thereof (e.g., phosphate), about 0.02% w/w gentamicin or a pharmaceutically acceptable salt thereof (e.g., sulfate), and about 0.3% w/w econazole or a pharmaceutically acceptable salt thereof (e.g., nitrate).

In an aspect, a disclosed method can comprise mixing one or more excipients or additives with the compounded composition. In an aspect, excipients or additives include, but are not limited to, the following: solvents, surfactants, humectants, preservatives, flavorings, stabilizers (including antioxidants), binders, and colorants.

In an aspect, a disclosed method can comprise mixing a therapeutically effective amount of one or more additional antimicrobial agents with the compounded composition. In an aspect, the additional antimicrobial agent can be an antibacterial agent. In an aspect, the additional antimicrobial agent can be an antifungal agent. In an aspect, a disclosed method can comprise obtaining the additional antimicrobial agent. In an aspect, obtaining can comprise obtaining a bulk source of the antimicrobial agent.

In an aspect, a disclosed method can comprise packaging the compounded composition into a container and sealing the container. In an aspect, a container can be a container disclosed herein, such as, for example, a syringe. In an aspect, a disclosed method can comprise sterilizing the compounded composition.

In an aspect, the mixing can comprise using an electronic mortar and pestle (EMP). In an aspect, a disclosed method can comprise milling the homogeneous compounded composition (using, for example, a three-roll mill). Mixing and milling can be done according to standards known to the skilled person in the art. Generally, to make the compounded composition, mupirocin, clindamycin or a pharmaceutically acceptable salt thereof (e.g., phosphate), gentamicin or a pharmaceutically acceptable salt thereof (e.g., sulfate), and econazole or a pharmaceutically acceptable salt thereof (e.g., nitrate) can be combined and mixed together using, for example, an electronic mortar and pestle (EMP). In an aspect, the EMP can be the Unguator 2100 or a similar device as recognized by the skilled person in the art. The compounded composition can be mixed at least one time using the "normal" (or a comparable) setting. Then, the compounded composition can be milled to achieved the desired consistency using, for example, a three-roll mill (e.g., an Exakt 120S-450). The milled compounded composition can then be mixed again using, for example, an EMP, and then distributed into one or more containers, such as one or more containers disclosed herein (e.g., a plastic tube, a glass or non-glass vial, a syringe, etc.).

Example 21

In an aspect, to make 1 g of the compounded composition comprising about 0.9% w/w mupirocin, about 0.05% w/w clindamycin phosphate, about 0.02% w/w gentamicin sulfate, and about 0.3% w/w econazole nitrate, about 0.45 g of mupirocin 2.0% cream or ointment, about 0.05 g of clindamycin phosphate 1.0% gel ointment, about 0.20 g gentamicin sulfate 0.1% ointment, and about 0.30 g econazole nitrate 1.0% cream can be combined and mixed together according to a method described above.

Table 21 provides the approximate amount of mupirocin, clindamycin phosphate, gentamicin sulfate, and econazole nitrate needed to make various amounts of the compounded composition.

TABLE 21

MUPIROCIN, CLINDAMYCIN PHOSPHATE, GENTAMICIN SULFATE, AND ECONAZOLE NITRATE

| Compounded Composition (in grams) | Mupirocin (2.0% cream or ointment) | Clindamycin Phosphate (1.0% gel) | Gentamicin Sulfate (0.1% ointment) | Econazole Nitrate (1.0% cream) |
|---|---|---|---|---|
| 1 | 0.45 g | 0.05 g | 0.20 g | 0.30 g |
| 4 | 1.8 g | 0.2 g | 0.80 g | 1.2 g |
| 8 | 3.6 g | 0.4 g | 1.6 g | 2.4 g |
| 25 | 11.25 g | 1.25 g | 5.0 g | 7.5 g |
| 50 | 22.5 g | 2.5 g | 10.0 g | 15.0 g |
| 240 | 108.0 g | 12.0 g | 48.0 g | 72.0 g |
| 1500 | 675.0 g | 75.0 g | 300.0 g | 450.0 g |

As used in Example 21, the term "about" means a value falling within a range that is ±10% of the stated value. In an aspect, the skilled person can combine 0.45 g±10% mupirocin 2.0% cream or ointment (e.g., from about 0.405 g-0.495 g), 0.05 g±10% clindamycin phosphate 1.0% gel (e.g., from about 0.045 g-0.055 g), 0.20 g±10% gentamicin sulfate 0.1% ointment (e.g., from about 0.18 g-0.22 g), and 0.30 g±10% econazole nitrate 1.0% ointment (e.g., from about 0.27 g-0.33 g) and mix together according to a method described above to make about 1.0 g±10% of the compounded composition.

8. Treating or Preventing an Infection Using a Compounded Composition

Disclosed herein is a method of treating or preventing an infection, the method comprising: applying to the skin of a subject a compounded composition described above or elsewhere herein, such as a compounded composition comprising one of the following 31 active combinations (1) a therapeutically effective amount of a first antibacterial agent and a therapeutically effective amount of a second antibacterial agent, (2) a therapeutically effective amount of an antibacterial agent and a therapeutically effective amount of an antifungal agent, (3) a therapeutically effective amount of a first antibacterial agent, a therapeutically effective amount of a second antibacterial agent, and a therapeutically effective amount of an antifungal agent, (4) a therapeutically effective amount of mupirocin and a therapeutically effective amount of an antibacterial agent, (5) a therapeutically effective amount of mupirocin and a therapeutically effective amount of tobramycin or a pharmaceutically acceptable salt thereof, (6) a therapeutically effective amount of mupirocin and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof, (7) a therapeutically effective amount of mupirocin and a therapeutically effective amount of doxycycline or a pharmaceutically acceptable salt thereof, (8) a therapeutically effective amount of mupirocin and a therapeutically effective amount of azithromycin, (9) a therapeutically effective amount of mupirocin and a therapeutically effective amount of ciprofloxacin or a pharmaceutically acceptable salt thereof, (10) a therapeutically effective amount of mupirocin and a therapeutically effective amount of clindamycin or a pharmaceutically acceptable salt thereof, (11) a therapeutically effective amount of mupirocin and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, (12) a therapeutically effective amount of mupirocin and a therapeutically effective amount of an antifungal agent, (13) a therapeutically effective amount of mupirocin and a therapeutically effective amount of an antifungal agent comprising one or more antifungals or pharmaceutically acceptable salt thereof selected from ketoconazole, voriconazole, amphotericin B, or combinations thereof, (14) a therapeutically effective amount of mupirocin and a therapeutically effective amount of ketoconazole, (15) a therapeutically effective amount of mupirocin and a therapeutically effective amount of nystatin, (16) a therapeutically effective amount of mupirocin, a therapeutically effective amount of an antibacterial agent, and a therapeutically effective amount of an antifungal agent, (17) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof, (18) a therapeutically effective amount of mupirocin, a therapeutically effective amount of doxycycline or a pharmaceutically acceptable salt thereof, and a therapeutically effective amount of fluconazole, (19) a therapeutically effective amount of mupirocin, a therapeutically effective amount of doxycycline or a pharmaceutically acceptable salt thereof, and a therapeutically effective amount of ketoconazole, (20) a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and one or both of voriconazole or amphotericin B or pharmaceutically acceptable salt thereof, (21) a therapeutically effective amount of mupirocin, a therapeutically effective amount of tobramycin or a pharmaceutically acceptable salt thereof, and a therapeutically effective amount of ketoconazole or fluconazole, (22) a therapeutically effective amount of mupirocin, a therapeutically effective amount of a fluoroquinolone, and a therapeutically effective amount of an azole, (23) a therapeutically effective amount of mupirocin, a therapeutically effective amount of ciprofloxacin or a pharmaceutically acceptable salt thereof, and a therapeutically effective amount of ketoconazole, (24) a therapeutically effective amount of mupirocin, a therapeutically effective amount of azithromycin, and a therapeutically effective amount of ketoconazole, (25) a therapeutically effective amount of mupirocin, a therapeutically effective amount of clindamycin or a pharmaceutically acceptable salt thereof, a therapeutically effective amount of gentamicin or a pharmaceutically acceptable salt thereof, and a therapeutically effective amount of econazole or a pharmaceutically acceptable salt thereof, (26) a therapeutically effective amount of doxycycline or a pharmaceutically acceptable salt thereof and a therapeutically effective amount of nystatin, (27) a therapeutically effective amount of tobramycin or a pharmaceutically acceptable salt thereof and a therapeutically effective amount of nystatin, (28) a therapeutically effective amount of clobetasol propionate and a therapeutically effective amount of fluconazole or urea, (29) a therapeutically effective amount of clobetasol propionate and a therapeutically effective amount of ketoconazole, (30) a therapeutically effective amount of ketoconazole, a sufficient amount of an excipient base powder comprising a blend of micronized xylitol and poloxamers, and a sufficient amount of xylitol, or (31) a therapeutically effective amount of mupirocin in combination with a therapeutically effective amount of additional antimicrobials according to any of the compounded compositions described herein.

Disclosed herein is a method of treating or preventing an infection, the method comprising: preparing a homogeneous compounded composition comprising described above or elsewhere herein, such as a compounded composition comprising one of the 31 active combinations identified above.

The compounded compositions described herein may be utilized in a variety of formats. For example, the compounded composition may be utilized in a nasal irrigation, e.g., via NeilMed® Irrigation Delivery; topical bath irrigation; topical spray application; topical irrigation application; topical gauze application; or other topical external application. In various embodiments, the topical composition comprises a cream or ointment including mupirocin, such as mupirocin 2% cream or ointment. The compounded composition may include an additional antibacterial or an antifungal agent. The compounded composition may be combined with a carrier or diluent to formulate a treatment solution format for nasal irrigation; topical bath irrigation, e.g., submersion; topical spray application; topical irrigation application; topical gauze application, or other topical external application, such as those described herein. The carrier or diluent may comprise an aqueous solution, non-aqueous solution, sodium hypochlorite, Dakin's solution, water, sterile water, water for injection, water for irrigation, hydrogen peroxide, or sodium chloride, for example.

In various embodiments, compounded compositions or treatment solutions comprising mupirocin described herein may include a daily dosage of between about 100 mg and about 800 mg, about 200 mg and about 600 mg, about 350 mg and about 550 mg, about 350 mg and about 500 mg, about 400 mg and about 450 mg, about 450 mg and about 550 mg, or about 500 mg and about 800 mg of mupirocin. The daily dosage of mupirocin may be administered in a single administration or divided between two or three administrations.

In some examples, a treatment solution may include mupirocin 2% cream or mupirocin 2% ointment in an amount described herein without an additional antimicrobial pharmaceutical drug. For example, mupirocin 2% cream or mupirocin 2% ointment may be combined with a carrier or diluent to formulate a treatment solution format for nasal irrigation; topical bath irrigation, e.g., submersion; topical spray application; topical irrigation application; topical gauze application, or other topical external application, such as those described herein. The carrier or diluent may comprise an aqueous solution, non-aqueous solution, sodium hypochlorite, Dakin's solution, water, sterile water, water for injection, water for irrigation, hydrogen peroxide, or sodium chloride, for example.

In various embodiments, infected tissue may include a bacterial infection. For example, the tissue may be infected by a Gram-positive bacterial strain. In one example, the compounded composition or a treatment comprising the compounded composition may be used to treat an infection selected from *Staphylococcus aureus* (MSSA), *Staphylococcus aureus* (MRSA), *Staphylococcus epidermidis, Corynebacterium striatum*, Group A *Streptococcus pyogene, Enterococcus faecalis, Acinetobacter baumannii, Klebsiella pneumonia, Enterobacter cloacae* complex, or *Pseudomonas aeruginosa*.

In an aspect, a disclosed method can comprise orally administering to the subject a pharmaceutical composition comprising one or more antimicrobial agents. In an aspect, the additional antimicrobial agent can be an antibacterial agent. In an aspect, the additional antimicrobial agent can be an antifungal agent.

The present disclosure also describes methods of treating an infection by providing or administering a compounded composition described herein. In some embodiments, the method may include formulating the compounded composition for topical treatment of an infection of skin, which may include broken or unbroken wounded skin. The treatment method may include contacting the compounded composition to skin, nails, or body orifice that is infected or believed to be infected. The infection may be of an exterior surface of the body, an orifice, or internal. Administration may include bath-irrigation, topical irrigation via a syringe, administration in a topical powder, or a topical gel, cream, ointment, or lotion. Administration may be to an external surface of the body or to anal or vaginal surfaces. In various embodiments, the compounded composition may be administered via contact to an infected area such as to skin of a head, face, ears, nose, neck, shoulder, torso, chest, stomach, waistline, extremity, arm, hand, finger, nail, groin, buttock, leg, foot, or toe, for example. In an embodiment of a method to treat an internal infection, the compounded composition may be administered topically as described herein wherein one or more active agents are transdermally delivered locally or for systemic circulation. Additional active agents may be utilized in the compounded composition to reduce pain, irritation, and inflammation such as NSAIDs, steroids, local anesthetics, anticonvulsants, antidepressants, for example. In various embodiments, the compounded composition may be administered 1 to 2 times daily or as otherwise needed.

In one embodiment, a compounded composition may be used to treat an infection or suspected infection accompanying a hyperkeratotic skin conditions that are marked by a thickening of the outer layers of skin. Methods of using the compounded composition may include treating an individual in need by topically applying the composition to affected skin. Conditions treated may include conditions such as those marked by thickening of the skin, referred to as hyperkeratosis. The compounded composition described herein may thus be applied to such affected areas of the skin to treat the affected area. The composition may alleviate symptoms such as redness, swelling, or itching. The composition may accelerate the healing process with respect to the affected skin. In various embodiments, the compounded composition may be administered to treat hyperkeratotic conditions. The hyperkeratotic skin condition treated may include chronic eczema, corns, calluses, warts, seborrheic keratosis, lichen planus, actinic keratosis, as examples. The hyperkeratotic skin conditions may be caused by irritation, such as physical pressure or rubbing, chemical, infection, sunlight or radiation, or inherited conditions, for example. In an embodiment, the compounded composition may be administered to such affected skin in a preventative treatment regime to combat proliferation of microbial infections with respect to the thickened skin layers. In some such embodiments, the compounded composition may include a keratolytic agent as described herein.

Compounded compositions comprising cream, lotion, paste, ointment, and similar formats may be applied by contact to skin, or mucosal tissue with respect to anal or vaginal administration. In some embodiments, the compounded composition may be formulated in a shampoo carrier for administration in a shampoo. In some formats, the composition may be administered to an infected or target area via spray, drops, wash, swab, sponge, absorbent dressing, coating (e.g., a nail lacquer), soaking, submerging, footbath, instillation or irrigation. Embodiments comprising a nail lacquer formulation may be applied directly to nails, to treat a bacterial or fungal nail infection.

Various embodiments comprising a solution format may be administered in a footbath, which may include a hand bath or soak, to treat or prevent an infection. The method may include adding the compounded composition to a footbath. In some embodiments, the method may include addition of a carrier comprising an aqueous diluent. The aqueous diluent may be in addition to the carrier as described herein or may be the carrier. For example, a compounded composition comprising a solution, cream, ointment, powder, gel, paste, or lotion format may be added to a footbath. Additional carrier comprising an aqueous diluent may also be added. In some embodiments, the compounded composition prior to addition of the diluent comprises a concentrated compounded composition, and following addition of the carrier comprising the diluent, the compounded composition comprises the percent compositions described herein. The footbath solution may be agitated and/or heated in some embodiments. A foot or a hand may contact the footbath solution in the footbath for administration of the compounded composition.

A method of treating or preventing an infection may include formulating a footbath solution comprising combining the antimicrobial agent and a carrier comprising a diluent. The carrier may comprise a liquid or dry powder diluent, base powder, cream, ointment, or other carrier identified herein.

A method treating or preventing an infection may include formulating an irrigation solution comprising combining the antimicrobial agent and a carrier comprising a diluent. The carrier may comprise a liquid or dry powder diluent, base powder, cream, ointment, or other carrier identified herein.

A method of treating a wound may include formulating a wound treatment ointment, powder, cream, or solution comprising combining the antimicrobial agent and a carrier. The carrier may comprise a liquid or dry powder diluent, base powder, cream, ointment, or other carrier identified herein.

Formulating a compounded composition comprising a treatment solution for a footbath, irrigation, or spray may comprise adding the antimicrobial agent to a carrier comprising a diluent and agitating or mixing. The compounded composition may be administered in a footbath by contacting a skin surface that is infected or suspected to be infected. The skin surface may be a hand, foot, limb, torso, or other surface identified herein. The compounded composition may be administered by irrigation by pouring onto skin or an orifice. In some embodiments, the skin or mucosal tissue comprises a wound, which may include broken or unbroken tissue.

In various embodiments, the diluent may comprise an aqueous solution, non-aqueous solution, sodium hypochlorite, Dakin's solution, water, sterile water, water for injection, water for irrigation, hydrogen peroxide solution, or sodium chloride.

In an aspect, the amount of diluent can be approximately 3.75 mL to approximately 60 mL. In an aspect, the amount of diluent can be approximately 15 mL. In some embodiments, the amount of diluent may be between 0.5 L and 5 L, or more, such as sufficient diluent to achieve a desired volume, such as those identified elsewhere herein. In an aspect, the method can comprise adding to the diluent an excipient base powder comprising a blend of micronized xylitol and poloxamers. In an aspect, the excipient base powder can comprise LoxaSperse® excipient base powder. In an aspect, the excipient base powder can comprise LoxaSperse® excipient base powder and XyliFos® excipient base powder. In an aspect, an excipient base powder can be obtained from a bulk source.

In an aspect, the subject has been diagnosed with or is suspected of having a bacterial infection that affects exterior skin or mucosal tissue of the vaginal orifice or anus. In an aspect, the subject has been diagnosed with or is suspected of having a fungal infection exterior skin or mucosal tissue of the vaginal orifice or anus.

In an aspect, the subject can have diabetes. In an aspect, the subject can be obese. In an aspect, the subject can have poor blood flow. In an aspect, the subject can routinely wear thick socks. In an aspect, the subject can routinely wear heavy boots, gloves, or clothing.

In some embodiments, a method of treating or preventing a, infection associated with a *Candida*, such as *Candida albicans, Candida auris, Candida glabrata, Candida krusei*, or *Candida tropicalis* may include topically applying the compounded composition to target skin or mucosal surface. In some examples, the antimicrobial agent may comprise an antifungal component comprising an azole. The compounded composition may also include one or more additional antifungal active drugs, an antibacterial component, and/or one or more additional active agents.

In an aspect, contacting can comprise placing at least part of the skin or mucosal tissue of the subject believed to be infected or of which infection is to be prevented in the footbath. In an aspect, contacting can comprise placing at least part of one or both feet of the subject in the footbath for approximately 5 to approximately 15 minutes.

In one embodiment, the method may include heating the solution contained within the footbath. In an aspect, a footbath can comprise a mechanical agitation agent operable to mechanically agitate the enclosed solution, a heating agent to heat the enclosed solution, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the footbath. Motors and agitators are known to the art. In an aspect, mechanical agitation can serve to distribute the compounded composition throughout the water contained within the footbath. Heating agents and/or means to heat water in a compartment are known to the art.

In an aspect, a disclosed method can comprise repeating administration until the bacterial infection, suspected bacterial infection, the fungal infection, or the suspected fungal infection is eradicated or appears to be eradicated. In an aspect, a disclosed method can comprise repeating administration twice daily until the bacterial infection, suspected bacterial infection, the fungal infection, or the suspected fungal infection is eradicated or appears to be eradicated. In an aspect, a disclosed method can comprise repeating administration twice daily for a pre-determined amount of time. In an aspect, the pre-determined amount of time can comprise at least 5 days, at least 7 days, at least 10 days, at least 14 days, at least 21 days, at least 30 days, or more than 30 days. In an aspect, the pre-determined amount can comprise an amount of time lasting at least 5-7 days, at least 7-10 days, at least 10-14 days, at least 14-21 days, at least 21-30 days, at least 30 days, or more than 30 days.

In an aspect, applying the compounded composition can comprise contacting the compounded composition with the subject's skin until the compounded composition has been absorbed or substantially absorbed by the skin. In an aspect, applying can comprise using a sterile applicator to contact the compounded composition with the skin. In an aspect, applying can comprise contacting about 2 g to about 6 g, or about 3 g to about 5 g, or about 4 g of the compounded composition with the subject's skin. In an aspect, a disclosed compounded composition can be applied to skin in conjunction with an occlusive dressing. In an aspect, a disclosed method can comprise applying a covering to the skin affected by the infection.

In an aspect, a disclosed compounded composition can be mixed with a diluent to form a solution or suspension and then applied to the subject's skin. A solution is intended to include liquid mixtures including suspensions and dispersions. In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL. In an aspect, a disclosed method can comprise cleaning and drying a mixing container.

In an aspect, a disclosed compounded composition can be applied to the subject's skin as a dry powder or as a cream or ointment. In an aspect, a disclosed compounded composition can be applied to the subject's skin as a cream, or lotion, or emulsion, or gel. For example, the compounded composition may comprise a compounded cream or ointment as described herein.

In one embodiment, a method of treating an infection comprises applying to infected skin a compounded composition cream or ointment comprising a therapeutically effective amount of mupirocin cream (e.g., mupirocin 2% cream) or mupirocin ointment (e.g., mupirocin 2% ointment) and a therapeutically effective amount of an antibacterial agent comprising one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise antimicrobial for injection powder compounded with the mupirocin cream or mupirocin ointment.

In one embodiment, a method of treating an infection comprises applying to infected skin a compounded composition cream or ointment comprising a therapeutically effective amount of mupirocin cream (e.g., mupirocin 2% cream) or mupirocin ointment (e.g., mupirocin 2% ointment) and a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise antimicrobial for injection powder compounded with the mupirocin cream or mupirocin ointment. For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof.

In one embodiment, a method of treating an infection comprises applying to infected skin a compounded composition cream or ointment comprising a therapeutically effective amount of mupirocin cream (e.g., mupirocin 2% cream) or mupirocin ointment (e.g., mupirocin 2% ointment) and a therapeutically effective amount of an antifungal agent comprising one or more antifungals or pharmaceutically acceptable salt thereof selected from ketoconazole, voriconazole, amphotericin B, or combinations thereof. All or a portion of the antifungal agent may comprise antimicrobial for injection powder compounded with the mupirocin cream or mupirocin ointment.

In one embodiment, a method of treating an infection comprises applying to infected skin a compounded composition cream or ointment comprising a therapeutically effective amount of mupirocin cream (e.g., mupirocin 2% cream) or mupirocin ointment (e.g., mupirocin 2% ointment), a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising one or more antifungals or pharmaceutically acceptable salt thereof selected from ketoconazole, voriconazole, amphotericin B, or combinations thereof. All or a portion of the antibacterial agent may comprise antimicrobial for injection powder compounded with the mupirocin cream or mupirocin ointment. For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof. All or a portion of the antifungal agent may comprise antimicrobial for injection powder compounded with the mupirocin cream or mupirocin ointment.

In one embodiment, a method of treating an infection comprises applying to infected skin a compounded composition cream or ointment comprising a therapeutically effective amount of mupirocin, a therapeutically effective amount of an antibacterial agent comprising doxycycline or pharmaceutically acceptable salt thereof and one or more antibacterials or pharmaceutically acceptable salt thereof selected from bacitracin, colistimethate, piperacillin-tazobactam, polymyxin B, streptomycin, or combinations thereof, and a therapeutically effective amount of an antifungal agent comprising ketoconazole or pharmaceutically acceptable salt thereof and For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof. All or a portion of the antibacterial agent may comprise antimicrobial for injection powder compounded with the mupirocin cream or mupirocin ointment. For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof. All or a portion of the antifungal agent may comprise antimicrobial for injection powder compounded with the mupirocin cream or mupirocin ointment. For example, ketoconazole may comprise crushed tablets of ketoconazole and the one or more antifungals or pharmaceutically acceptable salt thereof selected from For example, doxycycline may comprise doxycycline hyclate obtained from crushed tablets and the one or more antibacterials or pharmaceutically acceptable salt thereof selected from bacitracin, colistimethate, piperacillin-tazobactam, polymyxin B, streptomycin, or combinations thereof may be obtained from powder for injection formats comprising the one or more antibacterials or pharmaceutically acceptable salt thereof selected from bacitracin, colistimethate, piperacillin-tazobactam, polymyxin B, streptomycin, or combinations thereof may be obtained from powder for injection formats.

In an aspect, the subject can be diagnosed with or can be suspected of having a bacterial infection or a fungal infection that affects the subject's skin. In an aspect, the subject can have diabetes, can be obese, can be immunocompromised, can be non-ambulatory, or can have poor blood flow, or a combination thereof. In an aspect, the subject can routinely wear thick socks or wear heavy boots.

In an aspect, a disclosed method can comprise preparing a disclosed compounded composition. In an aspect, a disclosed method of treating or preventing an infection can comprise modifying one or more aspect of the disclosed method. For example, in an aspect, a disclosed method can comprise changing or altering the amount of the disclosed compounded composition applied to a subject's skin, or by changing the frequency of the subject's use of the compounded composition, or by changing the duration of time that the subject uses the compounded composition, or by substituting one compounded composition for another compounded composition, or a combination thereof.

9. Treating or Preventing a Foot Infection

Treatment for a foot infection may include administration of the compounded composition in a footbath. A footbath refers to a container that can hold some volume (e.g., approximately 1.0 liters to approximately 30 liters) of a treatment or footbath solution, which may typically be an aqueous solution or suspension, and is designed to physically accommodate at least a portion of one or both feet of a subject. A footbath administration includes administration of the compounded composition utilizing a footbath. A footbath may be used as a hand bath; however, smaller bathing containers may typically be utilized as hand baths. In various embodiments, footbath solutions may be utilized as hand bath solutions. A footbath may also be utilized for other body portions other than the hand or foot, e.g., legs, arms, limbs, torso, scalp, ear, face, chest, or back. A footbath can comprise several features or agents that effect various functions. For example, a footbath can comprise one or more lights or light-emitting devices, a mechanical agitation agent (e.g., one or more jets or bubble makers) to physically agitate the enclosed water, a bubble agent to create bubbles within the enclosed water, a heating agent to heat the enclosed water, a vibration agent to vibrate the enclosed water (e.g., a high frequency vibration massage), an infrared device to provide infrared light to a foot or other body portion of the subject within the bath, a massage agent (e.g., a roller) that provides massaging contact to at least a portion of one or both feet, a pedicure agent that can clean or contact a foot or feet with a pumice, or a combination thereof. In an aspect, a footbath can have a waterfall element. In an aspect, an agitation agent or an agitator can be coupled to both a motor and the footbath. In an aspect, a footbath can comprise one or more splashguards and other spill-resistant features to ensure that the water remains enclosed within a container. A footbath may also accommodate a subject's calves, meaning that the container is "deep" so as to allow the enclosed water to contact both the feet and at least a portion of the calves of the subject. Several manufacturers market footbaths including PIBB, Dr. Scholl's, Kendal, Conair (e.g., Model FB5X, FB3, FB27R, FB30, FB52, etc.), and Brookstone.

Disclosed herein is a method of treating or preventing a foot infection, the method comprising: (i) adding a compounded composition to water contained within a footbath; (ii) agitating the water contained within the footbath; and (iii) contacting the agitated water with at least a part of one or both feet of a subject.

Disclosed herein is a method of treating or preventing a foot infection, the method comprising: (i) agitating water contained within a footbath; (ii) adding a compounded composition to the water contained with the footbath; and (iii) contacting the agitated water with at least a part of one or both feet of a subject.

Disclosed herein is a method of treating or preventing a foot infection, the method comprising: (i) mixing a compounded composition with a diluent to create a solution or suspension; (ii) adding the solution or suspension to water contained within a footbath; (iii) agitating the water contained within the footbath; and (iv) contacting the agitated water with at least part of one or both feet of a subject.

Disclosed herein is a method of treating or preventing a foot infection, the method comprising: (i) mixing a compounded composition with a diluent to create a solution or suspension; (ii) agitating water contained within a footbath; (iii) adding the solution or suspension to the water contained within the footbath; and (iv) contacting the agitated water with at least part of one or both feet of a subject.

Disclosed herein is a method of treating or preventing a foot infection, the method comprising: (i) adding a compounded composition to water contained within a footbath; (ii) agitating the water contained within the footbath; and (iii) contacting the agitated water with at least a part of one or both feet of a subject, wherein the compounded composition comprises a composition as described above or elsewhere herein, such as a compounded composition comprising one of the 31 active combinations identified.

Disclosed herein is a method of treating or preventing a foot infection, the method comprising: (i) agitating water contained within a footbath; (ii) adding a compounded composition to the water contained within the footbath; and (iii) contacting the agitated water with at least a part of one or both feet of a subject. The compounded composition may be any compounded composition, e.g., compounded cream or ointment, described herein.

Disclosed herein is a method of treating or preventing a foot infection, the method comprising: (i) mixing a compounded composition with a diluent to create a solution or suspension; (ii) adding the solution or suspension to water contained within a footbath; (iii) agitating the water contained within the footbath; and (iv) contacting the agitated water with at least part of one or both feet of a subject, wherein the compounded composition comprises a composition as described above or elsewhere herein, such as a compounded composition comprising one of the 31 active combinations.

Disclosed herein is a method of treating or preventing a foot infection, the method comprising: (i) mixing a compounded composition with a diluent to create a solution or suspension; (ii) agitating water contained within a footbath; (iii) adding the solution or suspension to the water contained within the footbath; and (iv) contacting the agitated water with at least part of one or both feet of a subject, wherein the compounded composition comprises a composition as described above or elsewhere herein, such as a compounded composition comprising one of the 31 active combinations.

In an aspect, a disclosed method can treat or prevent an infection affecting the skin of at least a portion of a subject's foot or feet. In an aspect, a disclosed method can treat or prevent an infection affecting the nail of at least one toe on a subject's foot or feet.

In an aspect, the subject can have diabetes, can be obese, can be immunocompromised, can be non-ambulatory, or can have poor blood flow, or a combination thereof. In an aspect, the subject can routinely wear thick socks or wear heavy boots. In an aspect, the subject has been diagnosed with or is suspected of having a bacterial infection that affects at least part of one or both feet. In an aspect, the subject has been diagnosed with or is suspected of having a bacterial infection and a fungal infection that affect at least part of one or both feet. In an aspect, the subject has been diagnosed with or is suspected of having a fungal infection that affects at least part of one or both feet.

In an aspect, a disclosed method can comprise orally administering to the subject a pharmaceutical composition comprising one or more antimicrobial agents. In an aspect, the additional antimicrobial agent can be an antibacterial agent. In an aspect, the additional antimicrobial agent can be an antifungal agent.

In an aspect, adding a disclosed compounded composition to the water contained within a footbath can comprise adding to the water between about 10 g to about 40 g of a disclosed compounded composition, or about 20 g to about 30 g of a disclosed compounded composition, or about 25 g of a disclosed compounded composition.

In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL.

In an aspect, a disclosed method can comprise adding the diluent to the footbath. In an aspect, the diluent can comprise water, sterile water, water for injection, water for irrigation, sodium chloride solution, hydrogen peroxide solution, or sodium hypochlorite solution. In an aspect, the diluent can comprise Dakin's solution. In an aspect, the amount of diluent can be about 20 mL to about 60 mL, or about 30 to about 50 mL, or about 20 mL, or about 30 mL, or about 40 mL, or about 50 mL, or about 60 mL.

In an aspect, adding the solution or suspension comprising the compounded composition and the diluent can be added to the footbath already having water, thereby increasing the water level in the footbath.

In an aspect, a disclosed method can comprise heating the water contained within the footbath. In an aspect, a disclosed method can comprise agitating the water contained within the footbath. In an aspect, a footbath can comprise a mechanical agitation agent to mechanically agitate the enclosed water, a heating agent to heat the enclosed water, or both. Mechanical agitation agents and/or means to agitate water within a compartment are known to the art. In an aspect, a mechanical agitation agent can be a motorized agitation agent. In an aspect, an agitation agent or an agitator can be coupled to both a motor and the footbath. Motors and agitators are known to the art. In an aspect, mechanical agitation can serve to distribute the compounded composition, the diluent, or the solution or suspension comprising the compounded composition and the diluent throughout the water contained within the footbath. Heating agents and/or means to heat water in a compartment are known to the art.

In an aspect of a disclosed method, a disclosed compound composition can be added to the water contained within the footbath while the water is being heated. In an aspect of a disclosed method, a disclosed compound composition can be added to the water contained within the footbath while the water is being agitated.

In an aspect, agitation can ensure dissolution of the compounded composition or the dissolution of solution or suspension comprising the compounded composition.

In an aspect, agitation can ensure optimal contact of the compounded composition with at least a part of the subject's foot or feet.

In an aspect, a disclosed method can comprise repeating daily steps (i)-(iii) or steps (i)-(iv). In an aspect, a disclosed method can comprise repeating daily steps (i)-(iii) or steps (i)-(iv) until the bacterial infection, suspected bacterial infection, the fungal infection, or the suspected fungal infection is eradicated or appears to be eradicated. In an aspect, a disclosed method can comprise repeating twice daily administration for a pre-determined amount of time. In an aspect, the pre-determined amount of time can comprise at least 5 days, at least 7 days, at least 10 days, at least 14 days, at least 21 days, at least 30 days, or more. In an aspect, the pre-determined amount can comprise an amount of time lasting at least 5-7 days, at least 7-10 days, at least 10-14 days, at least 14-21 days, at least 21-30 days, or at least 30 days.

In an aspect, contacting can comprise placing at least part of one or both feet of the subject in the footbath. In an aspect, contacting can comprise placing at least part of one or both feet of the subject in the footbath for about 5 to about 15 minutes. In an aspect, contacting can comprise placing at least part of one or both feet of the subject in the footbath for about 10 minutes.

In an aspect, the method can comprise removing the compounded composition from a container, such as, for example, a tube, a packet, a capsule, a syringe, a vial, etc., prior to adding the compounded composition to the water. In an aspect, the method can comprise removing the compounded composition from a container, such as, for example, a tube, a packet, a capsule, a syringe, a vial, etc., prior to adding the composition to the diluent. In an aspect, a capsule can be broken apart and the contents of the capsule can be added to the water in the footbath. In an aspect, an intact capsule can be added to the water in the footbath.

In an aspect, a disclosed method can comprise emptying the water from the footbath. In an aspect, a disclosed method can comprise cleaning the footbath. In an aspect, a disclosed method can comprise drying the footbath.

In an aspect, a disclosed method can comprise preparing a disclosed compounded composition. In an aspect, a disclosed method of treating or preventing a foot infection can comprise modifying one or more aspect of the disclosed method. For example, in an aspect, a method can be altered by changing the amount of a disclosed compounded composition added to a footbath, by changing the frequency of the subject's use of the footbath, or by changing the duration of time that the subject's foot or feet contact the water contained within the footbath, or by substituting one disclosed compounded composition for another disclosed compounded composition, or a combination thereof.

In various aspects, a method of treating or preventing an infection, such as a foot infection, may comprise making or administering any of the disclosed compounded compositions to an affected skin surface of a subject. In some aspects, the compounded composition comprises a footbath composition for application to a foot of a subject. In one aspect, any of the disclosed compounded compositions may be administered in a footbath solution. For example, added into a mixing container along with a suitable amount of diluent.

The composition may be provided in a syringe, for example, for ease of addition with the diluent. The contents (e.g., 25 g) may be added to a suitable amount of diluent, as described herein, and mixed, e.g., in a mixing container. The amount of diluent may be about 15 ml diluent per tablespoon of the cream or ointment. Other ratios may be used, e.g., between about 10 ml and about 50 ml, about 10 ml and about 40 ml, about 10 ml and about 30 ml, about 10 ml and about 20 ml, about 10 ml and about 15 ml, about 15 ml and about 50 ml, about 15 ml and about 40 ml, about 15 ml and about 30 ml, about 10 ml and about 25 ml, about 15 ml and about 20 ml, about 20 ml and about 50 ml, about 20 ml and about 40 ml, about 20 ml and about 30 ml, or about 20 ml and about 25 ml. Furthermore, the compounded composition cream or ointment may be formulated with higher or lower concentrations of actives in the cream or ointment and amounts of the compounded composition cream or ointment added to diluent for administration may thereby adjusted accordingly. Mixing may include shaking or stirring to form a footbath solution. In a further aspect, the footbath solution may be further agitated. In one aspect, the mixing container comprises a footbath. In another aspect, the contents of the mixing container may be added to a footbath. Administering the footbath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily.

In various aspects, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

Disclosed herein is a compounded composition comprising a therapeutically effective amount of mupirocin, a therapeutically effective amount of azithromycin, and a therapeutically effective amount of ketoconazole. A disclosed compounded composition comprising mupirocin, azithromycin, and ketoconazole can comprise a dry powder formulation or can comprise a cream or ointment.

In an aspect, a disclosed compounded composition comprising mupirocin, azithromycin, and ketoconazole can comprise from about 1.0% w/w to about 3.0% w/w mupirocin. In an aspect, a disclosed compounded composition comprising mupirocin, azithromycin, and ketoconazole can comprise about 1.645% w/w mupirocin. In an aspect, a disclosed compounded composition comprising mupirocin, azithromycin, and ketoconazole can comprise from about 4.0% w/w to about 6.0% w/w azithromycin. In an aspect, a disclosed compounded composition comprising mupirocin, azithromycin, and ketoconazole can comprise about 5.0% w/w azithromycin. In an aspect, a disclosed compounded composition comprising mupirocin, azithromycin, and ketoconazole can comprise from about 4.0% w/w to about 6.0% w/w ketoconazole. In an aspect, a disclosed compounded composition comprising mupirocin, azithromycin, and ketoconazole can comprise about 5.0% w/w ketoconazole. In an aspect, a disclosed compounded composition comprising mupirocin, azithromycin, and ketoconazole can comprise about 1.645% w/w mupirocin, about 5.0% w/w azithromycin, and about 5.0% w/w ketoconazole.

In various aspects, a disclosed composition to treat or prevent an infection, such as a foot infection, includes a footbath composition. The footbath composition may be or be prepared with suitable diluent to form a footbath solution, which may be a mixture, emulsion, solution, suspension, etc. In some aspects, a footbath solution may comprise a footbath composition comprising between about 0.1 g and about 1.0 g, about 0.1 g to 0.8 g, about 0.1 g and about 0.5 g, about 0.1 g and about 0.3 g, about 0.2 g and about 0.8 g, about 0.2 g and about 0.5 g, about 0.2 g and about 0.3 g, or about 0.5 g and about 0.8 g doxycycline; between about 10 g and about 40 g, about 10 g to 30 g, about 10 g and about 25 g, about 10 g and about 15 g, about 20 g and about 40 g, about 20 g and about 30 g, about 20 g and about 25 g, or about 25 g and about 35 g mupirocin 2% cream or ointment or equivalent mupirocin; between about 5 g and about 35 g, about 5 g to 20 g, about 5 g and about 15 g, about 10 g and about 35 g, about 10 g and about 20 g, about 10 g and about 15 g, about 15 g and about 35 g, or about 15 g and about 25 g nystatin topical powder in a suitable amount of diluent, as described herein. In one aspect, the footbath solution includes three 100 mg capsules of doxycycline (0.3 g of doxycycline), one 22 g tube of mupirocin 2% cream or ointment (440 mg of mupirocin), and one 15 g container of nystatin topical powder (15 g of nystatin powder) in a suitable volume of diluent. In various aspects, additional active ingredients may be added to the footbath.

In various aspects, a method of treating or preventing an infection, such as a foot infection, may comprise making administering any of the disclosed footbath compositions or solutions to a subject. For example, a footbath composition may comprise three 100 mg capsules of doxycycline (0.3 g of doxycycline), one 22 g tube of mupirocin 2% cream or ointment (440 mg of mupirocin), and one 15 g container of nystatin topical powder (15 g of nystatin powder) and may be added into a mixing container along with a suitable amount of diluent. The contents may be mixed, e.g., shaken or stirred, to form a footbath solution. In a further aspect, the footbath solution may be further agitated. In one aspect, the mixing container comprises a footbath. In another aspect, the contents of the mixing container may be added to a footbath. Administering the footbath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily. In one aspect a 30 day supply may include ninety 100 mg capsules of doxycycline (9 g doxycycline); thirty 22 g tubes of mupirocin 2% cream or ointment (660 g of mupirocin); and thirty 15 g containers of nystatin topical powder (450 g of nystatin powder).

In various aspects, the method of treating or preventing an infection, such as a foot infection, may include making or administering any of the above footbath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

In various aspects, the composition to treat or prevent an infection, such as a foot infection, includes the compounded composition as described herein. The compounded composition may comprise a footbath composition that may be or be prepared with suitable diluent to form a footbath solution, which may be a mixture, emulsion, solution, suspension, etc. as described herein. In some aspects, a footbath solution may comprise a footbath composition comprising compounded powder of multiple medications, which may be provided in a capsule, comprising between about 0.1 g and about 1.0 g, about 0.1 g to 0.8 g, about 0.1 g and about 0.5 g, about 0.1 g and about 0.3 g, about 0.2 g and about 0.8 g, about 0.2 g and about 0.5 g, about 0.2 g and about 0.3 g, or about 0.5 g and about 0.8 g doxycycline; between about 10 g and about 40 g, about 10 g to 30 g, about 10 g and about 25 g, about 10 g and about 15 g, about 20 g and about 40 g, about 20 g and about 30 g, about 20 g and about 25 g, or about 25 g and about 35 g mupirocin 2% cream or ointment or equivalent mupirocin; and between about 5 g and about 35 g, about 5 g to 20 g, about 5 g and about 15 g, about 10 g and about 35 g, about 10 g and about 20 g, about 10 g and about 15 g, about 15 g and about 35 g, or about 15 g and about 25 g nystatin topical powder. The footbath solution may comprise the footbath composition in a suitable volume of diluent, as described herein. In one aspect, the footbath composition comprises a capsule containing about 100 mg doxycycline, about 30 mg mupirocin, and about 30 mg clotrimazole. In a further aspect, the footbath solution comprises the contents of the capsule mixed in a suitable volume of diluent. In various aspects, additional active ingredients may be added to the footbath.

In one aspect, a method of treating or preventing a foot infection, such as a foot infection, may comprise making or administering any of the above footbath compositions or solutions. In one example, the contents of a capsule may be added to a mixing container along with a suitable amount of diluent. The contents may be mixed, e.g., shaken or stirred, to form a footbath solution. In a further aspect, the footbath solution may be further agitated. In one aspect, the mixing container comprises a footbath. In another aspect, the contents of the mixing container may be added to a footbath. Administering the footbath solution may include placement of the foot (or feet) to be treated into the solution. The foot or portion to be treated thereof may be soaked, e.g., submerged, in the bath for a suitable period of time, e.g., between about 5 minutes and about 25 minutes, between about 5 minutes and about 20 minutes, about 5 minutes and about 15 minutes, about 5 minutes and about 10 minutes, between about 10 minutes and about 25 minutes, about 10 minutes and about 20 minutes, about 10 minutes and about 15 minutes, between about 15 minutes and about 25 minutes, about 15 minutes and about 20 minutes, or about 20 minutes and about 25 minutes. Administration may be repeated as directed, e.g., once daily.

In various aspects, the method of treating or preventing and infection, such as a foot infection, may include making or administering any of the above footbath compositions or solutions to a subject and further dispensing or administering up to about 2 g urea 40% cream or equivalent thereof to the affected area two times daily as directed (up to about 4 g per day) and applying up to about 4 g fluocinonide 0.1% cream to the affected area two times daily as directed (up to about 8 g per day). In another aspect, the method of treating or preventing a foot infection may include making or administering any of the above footbath compositions or solutions to a subject and further dispensing or administering up to about 2 g urea 40% cream or equivalent thereof to the affected area two times daily as directed (up to about 4 g per day) and applying up to about 3 g of clobetasol 0.05% ointment to the affected area two times daily as directed (up to about 6 g per day).

10. Treating or Preventing an Infection—Intranasally Administration

Disclosed herein is a method of treating or preventing an infection, the method comprising: (i) intranasally administering to a subject a solution or suspension comprising a compounded composition. Disclosed herein is a method of treating or preventing an infection, the method comprising: (i) mixing a compounded composition with a diluent to create a solution or suspension; and (ii) intranasally administering to a subject the solution or suspension.

Disclosed herein is a method of treating or preventing an infection, the method comprising: (i) intranasally administering to a subject a solution or suspension comprising a compounded composition, wherein the compounded composition comprises a composition as described above or elsewhere herein, such as a compounded composition comprising one of the 31 active combinations identified above.

Disclosed herein is a method of treating or preventing an infection, the method comprising: (i) mixing a compounded composition with a diluent to create a solution or suspension; and (ii) intranasally administering to a subject the solution or suspension, wherein the compounded composition comprises a composition as described above or elsewhere herein, such as a compounded composition comprising one of the 31 active combinations identified above.

In an aspect, the subject can have diabetes, can be obese, can be immunocompromised, can be non-ambulatory, or can have poor blood flow, or a combination thereof. In an aspect, the subject has been diagnosed with or can be suspected of having (i) cancer that affects at least a part of the respiratory tract, (ii) emphysema, (iii) pneumonia, (iv) bronchitis, (v) tuberculosis, (vi) asthma, or (vii) a combination thereof. In an aspect, the subject has been diagnosed with or is suspected of having a bacterial infection that affects at least a part of the subject's respiratory tract or a respiratory organ. In an aspect, the subject has been diagnosed with or is suspected of having a bacterial infection and a fungal infection that affect at least a part of the subject's respiratory tract or a respiratory organ. In an aspect, the subject has been diagnosed with or is suspected of having a fungal infection that affects at least one part of the subject's respiratory tract or a respiratory organ.

In an aspect, a disclosed method can comprise orally administering to the subject a pharmaceutical composition comprising one or more antimicrobial agents. In an aspect, the additional antimicrobial agent can be an antibacterial agent. In an aspect, the additional antimicrobial agent can be an antifungal agent.

In an aspect, mixing the compounded composition with the diluent can comprise adding about 1 g to about 30 g of the compounded composition to the diluent. In an aspect, mixing the compounded composition with the diluent can comprise adding about 1 g, or about 5 g, or about 10 g, or about 15 g, or about 20 g, or about 25 g, or about 30 g of the compounded composition to the diluent. In an aspect, mixing the compounded composition to the diluent can comprise adding about 10 g and about 20 g, about 15 g and about 30 g, about 20 g and about 30 g, or about 22 g and about 27 g of the compounded composition with the diluent.

In an aspect, a disclosed compounded composition and the diluent can be mixed in a mixing container. In an aspect, a mixing container can have a pre-determined size that can measure or hold a pre-determined amount or volume. In an aspect, a mixing container can measure or hold about 30 mL to about 300 mL. In an aspect, the mixing container can hold about 30 mL, about 60 mL, about 90 mL, about 120 mL, about 150 mL, about 180 mL, about 210 mL, about 240 mL, about 270 mL, or about 300 mL. In an aspect, the mixing container can hold about 180 mL.

In an aspect, the diluent can comprise sodium hypochlorite. In an aspect, the diluent can comprise Dakin's solution. In an aspect, the diluent may be an aqueous solution or non-aqueous solution. In an aspect, the diluent may comprise water, sterile water, water for injection, water for irrigation. In an aspect, the diluent may comprise hydrogen peroxide or sodium chloride. In an aspect, the amount of diluent can be about 20 mL to about 60 mL, or about 30 to about 50 mL, or about 20 mL, or about 30 mL, or about 40 mL, or about 50 mL, or about 60 mL. In an aspect, a disclosed method can comprise repeating daily the administering step. In an aspect, a disclosed method can comprise repeating daily the administering step until the bacterial infection or suspected bacterial infection or the fungal infection or the suspected fungal infection is eradicated or appears to be eradicated.

In an aspect, a disclosed method can comprise repeating daily the mixing step or the administering step or repeating both steps. In an aspect, a disclosed method can comprise repeating daily the mixing step or the administering step or reporting both the steps until the bacterial infection, suspected bacterial infection, the fungal infection, or the suspected fungal infection is eradicated or appears to be eradicated.

In an aspect, a disclosed method can comprise repeating the mixing step or the administering step or both the mixing step and the administering step for a pre-determined amount of time. In an aspect, the pre-determined amount of time can comprise at least 5 days, at least 7 days, at least 10 days, at least 14 days, at least 21 days, at least 30 days, or more. In an aspect, the pre-determined amount can comprise an amount of time lasting at least 5-7 days, at least 7-10 days, at least 10-14 days, at least 14-21 days, at least 21-30 days, or at least 30 days.

In an aspect, intranasally administering can comprise delivering to the subject the solution or suspension via the subject's nares. In an aspect, delivering the solution or suspension to the nares can comprise using irrigation, or using a nasal spray, or using a metered inhaler, or using nebulization, or using particle dispersion. In an aspect, delivering the solution or suspension can comprise a sinus rinse, which can use positive pressure to clean or irrigate the nasal passages and maintain the head of the subject in an upright position. A sinus rinse delivery device known to the art is the NeilMed® device. The art is familiar with each of these techniques, the equipment required to effect each of these techniques, and the means to prepare the compounded composition for each technique of intranasal administration.

In an aspect, a small particle nebulization delivery system can be configured to nebulize the solution or suspension comprising a disclosed compounded composition to produce small particles or droplets. In an aspect, small particles or droplets can have aerosol characteristics, wherein the particle size of the majority (e.g., at least 50%, at least 60%, at least 70%, at least 80%, at least 90%, or more) of the particles or droplets formed by the nebulization can be less than about 10 microns, or less than about 8 microns, or less than about 5 microns, or less than about 3 microns. In an aspect, the particles or droplets can be about 3-about 10 microns, or about 3 microns-about 8 microns, or about 3 microns-about 5 microns, or about 5 microns-about 8 microns, or about 5 microns-about 10 microns, or about 8 microns-about 10 microns.

In an aspect, a large particle nebulization delivery system can be configured to nebulize the solution or suspension comprising a disclosed compounded composition to produce large particles or droplets. In an aspect, small particles or droplets can have aerosol characteristics, wherein the particle size of the majority (e.g., at least 50%, at least 60%, at least 70%, at least 80%, at least 90%, or more) of the particles or droplets formed by the nebulization can be more than about 10 microns, or more than about 15 microns, or more than about 20 microns, or more than about 25 microns. In an aspect, the particles or droplet can be about 10 microns-about 25 microns, or about 10 microns-about 20 microns, or about 10 microns-about 15 microns, or about 15 microns-about 25 microns, or about 15 microns-about 20 microns, or about 20 microns-about 25 microns.

In an aspect, a disclosed method can comprise cleaning the device.

In an aspect, a disclosed method can comprise preparing a compounded composition disclosed herein In an aspect, a disclosed method of treating or preventing an infection using an intranasally administered compounded composition can comprise modifying one or more aspect of the disclosed method. For example, in an aspect, a method can be modified by changing the amount of a disclosed compounded composition intranasally administered, by changing the frequency of the subject's use of intranasal administration, or by substituting one disclosed compounded composition for another disclosed compounded composition, or a combination thereof.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

The term "contacting" as used herein refers to bringing one or more disclosed compositions, disclosed compounded compositions, or disclosed antimicrobial agents together with water and an intended target (such as at least a portion of one or both feet of a subject) or targeted area (such as an area diagnosed with, suspected of having a bacterial infection or a fungal infection, or susceptible to developing a bacterial infection or a fungal infection) in such a manner that the disclosed composition, a disclosed compounded composition, or a disclosed antimicrobial agent can exert an effect on the intended target or targeted area either directly or indirectly. In an aspect, "contacting" means to insert or immerse at least a portion of one or both feet of a subject into the water contained within a footbath.

The term "mixing" as used in a disclosed method of making a compounded composition, for example, means to physically combine the recited components so as to achieve a homogeneous compounded composition (which can be a dry powder formulation). For example, in an aspect, an antibacterial component and an antifungal component can be mixed with an excipient base powder; that is, an antibacterial component and an antifungal component are physically combined with an excipient base powder and shaken, or stirred, or agitated so as to achieve a homogeneous compounded composition. In an aspect, multiple recited components can be mixed together (i.e., antibacterial component, an antifungal component, an excipient base powder, and one or more additional antimicrobial agents (i.e., antibacterial component and antifungal component). In an aspect, "mixing" can also include sifting the homogeneous compounded composition though a fine mesh strainer. A suitable mixer is a TURBULA® mixer, which is able to mix powdery substances with differing specific weights and particle sizes. The mixing can be generally performed for a pre-determined amount of time, i.e., for 10 seconds, 20 seconds, 30 seconds, 45 seconds, 1 minute, 5 minute, 10 minutes, 20 minutes, 30 minutes, 40 minutes, 50 minutes, 1 hour, 2 hours, 3 hours, or more. A person skilled in the art could ascertain without undue experimentation, the amount of time required to mix the recited components so as to achieve a homogeneous compounded composition.

Also, in an aspect, "mixing" can be used to describe the process of making a solution by adding one or more of a disclosed compounded composition, a disclosed composition, or a disclosed antimicrobial agent to a diluent. For example, mixing means to physically combine one or more of a disclosed compounded composition, a disclosed composition, or a disclosed antimicrobial agent with a diluent.

"Mixing" can occur in a disclosed mixing container. In an aspect, a mixing container can have a pre-determined size that can measure or hold a pre-determined amount or volume. For example, in an aspect, a mixing container can measure or hold an amount of approximately 1 ounces to approximately 30 ounces. In an aspect, mixing container can measure or hold approximately 1 ounce, 2 ounces, 3 ounces, 4 ounces, 5 ounces, 6 ounces, 7 ounces, 8 ounces, 9 ounces, 10 ounces, 11 ounces, 12 ounces, 13 ounces, 14 ounces, 15 ounces, 16 ounces, 17 ounces, 18 ounces, 19 ounces, 20 ounces, 21 ounces, 22 ounces, 23 ounces, 24 ounces, 25 ounces, 26 ounces, 27 ounces, 28 ounces, 29 ounces, or 30 ounces. In an aspect, a mixing container can measure or hold approximately 6 ounces. In an aspect, a mixing container can measure or hold approximately 16 ounces.

As used herein, the term "subject" refers to the target of administration, e.g., an animal. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig, or rodent. The term does not denote a particular age or sex. Thus, adult and newborn subjects, as well as fetuses, whether male or female, are intended to be covered. In an aspect, a subject can be a human patient. A subject can have diabetes. A subject can be obese. A subject can have circulatory issues. A subject can have a bacterial infection, be suspected of having a bacterial infection, or be at risk of developing a bacterial infection. A subject can have a fungal infection, be suspected of having a fungal infection, or be at risk of developing a fungal infection. For example, a subject can have damaged or moist skin, can have chronic disease, or can be immunocompromised. A subject can have a bacterial infection and a fungal infection, be suspected of having a bacterial infection and a fungal infection, or be at risk of developing a bacterial infection and a fungal infection.

For example, a subject at risk of developing a bacterial infection can have, for example, risk factors for developing a bacterial infection (e.g., have damaged or moist skin, have chronic disease, and/or be immunocompromised). For example, a subject at risk for developing a bacterial infection can be exposed to a bacterium or bacteria due to employment (e.g., a health care worker) or due to the prevalence of a bacterium or bacteria at a specific location (e.g., a hospital).

For example, a subject at risk of developing a fungal infection can have, for example, risk factors for developing a fungal infection (e.g., have damaged or moist skin, have chronic disease, and/or be immunocompromised). For example, a subject at risk for developing a fungal infection can be exposed to a fungus or fungi due to employment (e.g., a health care worker) or due to the prevalence of a fungus or fungi at a specific location (e.g., a hospital).

As used herein, the term "treatment" refers to the medical management of a patient with the intent to cure, ameliorate, stabilize, or prevent a disease, pathological condition, or disorder (such as, for example, a bacterial infection, a suspected bacterial infection, a fungal infection, or a suspected fungal infection, or both). This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease.

As used herein, the term "prevent" or "preventing" refers to precluding, averting, obviating, forestalling, stopping, or hindering something from happening, especially by advance action, but which may also be encompassed by treating.

As used herein, the term "diagnosed" means having been subjected to a physical examination by a person of skill, for example, a physician, and found to have a condition that can be diagnosed or treated by the compounds, compositions, agents, or methods disclosed herein. For example, "diagnosed with a bacterial infection" means having been subjected to a physical examination by a person of skill, for example, a physician, and found to have a condition that can be diagnosed or can be treated by a disclosed compound or composition or agent that can prevent or inhibit a bacterial infection. For example, "suspected of having a bacterial infection" can mean having been subjected to a physical examination by a person of skill, for example, a physician, and found to have a condition that can be likely be diagnosed as or can likely be treated by a disclosed compound or composition or agent that can prevent or inhibit a bacterial infection, or it can mean that the subject believes that he or she has a bacterial infection. For example, "diagnosed with a fungal infection" means having been subjected to a physical examination by a person of skill, for example, a physician, and found to have a condition that can be diagnosed or can be treated by a disclosed compound or composition or agent that can prevent or inhibit a fungal infection. For example, "suspected of having a fungal infection" can mean having been subjected to a physical examination by a person of skill, for example, a physician, and found to have a condition that can be likely be diagnosed as or can likely be treated by a disclosed compound or composition or agent that can prevent or inhibit a fungal infection, or it can mean that the subject believes that he or she has a fungal infection.

As used herein, the terms "administering" and "administration" refer to any method of providing a disclosed composition, compounded composition, antimicrobial agent, or a pharmaceutical preparation to a subject. Such methods are well known to those skilled in the art and include, but are not limited to: oral administration, transdermal administration, administration by inhalation, nasal administration, topical administration, intravaginal administration, ophthalmic administration, intra-aural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a disclosed composition, compounded composition, or antimicrobial agent can be administered pharmaceutically; that is, administered to treat an existing disease or condition. In further various aspects, a disclosed composition, compounded composition, or antimicrobial agent can be administered prophylactically; that is, administered for prevention of a disease or condition. In an aspect, the skilled person can determine an efficacious dose, an efficacious schedule, and an efficacious route of administration for a disclosed composition, compounded composition, or antimicrobial agent so as to treat a subject or inhibit or prevent an inflammatory reaction. In an aspect, the skilled person can also alter, change, or modify an aspect of an administering step so as to improve efficacy of a disclosed composition, compounded composition, or antimicrobial agent. In an aspect, administering means contacting at least a portion of one foot or both feet of a subject with agitated solution comprising a disclosed composition, compounded composition, or antimicrobial agent in a footbath.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Various elements described herein have been described as alternatives or alternative combinations, e.g., in a lists of selectable actives, ingredients, or compositions. It is to be appreciated that embodiments may include one, more, or all of any such elements. Thus, this description includes embodiments of all such elements independently and embodiments including such elements in all combinations. Disclosed are the components to be used to prepare a disclosed compounded compositions as well as the disclosed compounded compositions to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity. As another example, a composition including 88% mupirocin cream or ointment includes a 88% mupirocin cream, 88% mupirocin ointment, or a combination of mupirocin cream and mupirocin ointment that together makeup 88% of the composition.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified. This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification.

Any numerical range recited herein includes all values and ranges from the lower value to the upper value. For example, if a concentration range is stated as 1% to 50%, it is intended that values such as 2% to 40%, 10% to 30%, 1% to 3%, or 2%, 25%, 39% and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" are intended to include +/−10% of the number modified.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

What is claimed is:

1. A method of treating one or both of a bacterial infection or fungal infection of a subject, the method comprising:
preparing a treatment solution comprising combining mupirocin 2% ointment comprising polyethylene glycol 400 and polyethylene glycol 3350, voriconazole, an aqueous diluent, and at least one additional antifungal drug or antibacterial drug; and topically administering the treatment solution to the subject, wherein topically administering comprises contacting a surface of a tissue of the subject to be treated with the treatment solution.

2. The method of claim 1, wherein the tissue surface comprises a nasal cavity of the subject, and wherein topically administering comprises contacting infected mucosal tissue of the nasal cavity with the treatment solution via irrigation, spray, or nasal nebulization.

3. The method of claim 1, wherein the tissue surface comprises a vagina or anus of the subject, and wherein administering comprises intravaginal or rectal administration comprising contacting infected mucosal tissue of the vagina or anus with the treatment solution.

4. The method of claim 1, wherein the tissue surface comprises a mouth of the subject, and wherein administering comprises buccal administration comprising contacting infected mucosal tissue of the mouth with the treatment solution.

5. The method of claim 1, wherein the tissue surface comprises skin of the subject, and wherein administering comprises spraying the treatment solution onto the infected skin surface, irrigating the infected skin surface with the treatment solution, or submerging the infected skin surface in the treatment solution.

6. The method of claim 1, wherein the tissue surface comprises an ear of the subject, and wherein administering comprises intra-aural administering of the treatment solution.

7. The method of claim 1, wherein preparing the treatment solution comprises adding a compounded composition to the aqueous diluent, and wherein the compounded composition comprises mupirocin 2% ointment and at least a portion of the voriconazole, at least one additional antifungal or antibacterial drug, or both.

8. The method of claim 1, wherein the at least one additional antifungal drug or antibacterial drug comprises an antibacterial drug selected from doxycycline, bacitracin, colistimethate, piperacillin-tazobactam, polymyxin B, tobramycin, or streptomycin.

9. The method of claim 8, wherein the selected antibacterial drug comprises one or more of bacitracin for injection, colistimethate sodium for injection, pentasodium colistin methanesulfonate for injection, piperacillin-tazobactam for injection, polymyxin B for injection, tobramycin sulfate for injection, or streptomycin sulfate for injection.

10. The method of claim 1, wherein the at least one additional antifungal drug or additional antibacterial drug comprises an antifungal drug comprises amphotericin B.

11. The method of claim 1, wherein the at least one additional antifungal drug or antibacterial drug comprises doxycycline, bacitracin, colistimethate, piperacillin-tazobactam, polymyxin B, streptomycin, tobramycin, or amphotericin B.

12. The method of claim 11 wherein the at least one additional antifungal drug or antibacterial drug comprises bacitracin for injection, colistimethate sodium for injection, pentasodium colistin methanesulfonate for injection, piperacillin-tazobactam for injection, polymyxin B for injection, streptomycin sulfate for injection, tobramycin sulfate for injection, or amphotericin B for injection.

13. The method of claim 1, wherein the at least one additional antifungal drug or antibacterial drug comprises doxycycline, streptomycin, and ketoconazole.

14. The method of claim 13, wherein preparing the treatment solution comprises adding the doxycycline, streptomycin, and ketoconazole to the aqueous diluent, and wherein the doxycycline, streptomycin, and ketoconazole comprise crushed doxycycline hyclate tablet, crushed ketoconazole tablet, and streptomycin sulfate for injection.

15. The method of claim 1, wherein the at least one additional antifungal drug or antibacterial drug comprises one of (i) streptomycin, (ii) streptomycin and doxycycline, or (iii) doxycycline and tobramycin.

16. The method of claim 1, wherein the aqueous diluent comprises sodium hypochlorite or Dakin's solution.

17. The method of claim 7, wherein the compounded composition comprises a compounded ointment comprising:

mupirocin 2% ointment in an amount at least 60% w/w of the compounded ointment and an antimicrobial for injection powder in an amount from about 1% to about 20% w/w of the compounded ointment, wherein the antimicrobial for injection comprises one or more of bacitracin for injection, colistimethate sodium for injection, pentasodium colistin methanesulfonate for injection, piperacillin-tazobactam for injection, polymyxin B for injection, streptomycin sulfate for injection, voriconazole for injection, tobramycin sulfate for injection, or amphotericin B for injection.

18. The method of claim 1, wherein the voriconazole is voriconazole for injection.

19. The method of claim 18, wherein preparing the treatment solution further comprises compounding the compounded ointment comprising combining mupirocin 2% ointment in an amount about 86% w/w of the compounded ointment and voriconazole for injection in an amount about 0.8% w/w of the compounded ointment.

20. The method of claim 18, wherein the antimicrobial for injection further comprises streptomycin sulfate for injection.

21. The method of claim 20, wherein preparing the treatment solution further comprises compounding the compounded ointment comprising combining mupirocin 2% ointment in an amount about 80% w/w of the compounded ointment, voriconazole for injection in an amount about 0.8% w/w of the compounded ointment, and streptomycin sulfate for injection in an amount about 5.528% w/w of the compounded ointment.

22. The method of claim 20, wherein preparing the treatment solution comprises compounding the compounded ointment comprising further combining crushed doxycycline hyclate tablet powder.

23. The method of claim 17, wherein preparing the treatment solution further comprises compounding the compounded ointment comprising combining mupirocin 2% ointment in an amount about 77.6% w/w of the compounded ointment, voriconazole for injection in an amount about 0.8% w/w of the compounded ointment, streptomycin sulfate for injection in an amount about 5.528% w/w of the compounded ointment, and a sufficient amount of crushed doxycycline hyclate tablet powder to obtain about 1% w/w doxycycline in the compounded ointment.

24. The method of claim 18, wherein the antimicrobial for injection comprises tobramycin for injection, and wherein preparing the treatment solution further comprises compounding the compounded ointment comprising combining crushed doxycycline hyclate tablet powder and mupirocin 2% ointment.

25. The method of claim 24, wherein preparing the treatment solution further comprises compounding the compounded ointment comprising combining mupirocin 2% ointment in an amount about 81.3% w/w of the compounded ointment, voriconazole for injection in an amount about 0.8% w/w of the compounded ointment, tobramycin sulfate for injection in an amount about 1.8% w/w of the compounded ointment, and a sufficient amount of crushed doxycycline hyclate tablet powder to obtain about 1% w/w doxycycline in the compounded ointment.

26. The method of claim 17, wherein the antimicrobial for injection comprises streptomycin sulfate for injection, and wherein the compounded ointment further comprises crushed doxycycline hyclate tablet powder and crushed ketoconazole tablet powder.

27. The method of claim 26, wherein preparing the treatment solution further comprises compounding the compounded ointment comprising combining mupirocin 2% ointment in an amount about 85.7% w/w of the compounded ointment, streptomycin sulfate for injection in an amount about 5.528% w/w of the compounded ointment, a sufficient amount of crushed doxycycline hyclate tablet powder to obtain about 2% w/w doxycycline in the compounded ointment, and a sufficient amount of crushed ketoconazole tablet powder to obtain about 2.5% w/w ketoconazole in the compounded ointment.

28. A method of treating one or both of a bacterial infection or fungal infection of a subject, the method comprising:
- preparing a treatment solution comprising combining mupirocin 2% cream comprising 2.15% w/w mupirocin calcium USP in an oil- and water-based emulsion, voriconazole, an aqueous diluent, and at least one additional antifungal drug or antibacterial drug
- topically administering the treatment solution to the subject, wherein topically administering comprises contacting a surface of a tissue of the subject to be treated with the treatment solution.

* * * * *